(12) United States Patent
Rothnagel et al.

(10) Patent No.: US 7,041,483 B2
(45) Date of Patent: May 9, 2006

(54) EXPRESSION MODULATING SEQUENCES

(75) Inventors: Joseph Attila Rothnagel, Kenmore (AU); Xue-Qing Wang, Kenmore (AU)

(73) Assignee: The University of Queensland, Queensland (AU)

( * ) Notice: Subject to any disclaimer, the term of this patent is extended or adjusted under 35 U.S.C. 154(b) by 88 days.

(21) Appl. No.: 09/880,253

(22) Filed: Jun. 13, 2001

(65) Prior Publication Data

US 2002/0111322 A1     Aug. 15, 2002

Related U.S. Application Data

(60) Provisional application No. 60/211,159, filed on Jun. 13, 2000.

(51) Int. Cl.
  *C12N 15/64*  (2006.01)
  *C12N 15/63*  (2006.01)
  *C12N 15/82*  (2006.01)
  *C12N 15/85*  (2006.01)

(52) U.S. Cl. ............... 435/91.41; 435/455; 435/468

(58) Field of Classification Search ............ 435/91.42, 435/91.41, 455, 468
  See application file for complete search history.

(56) References Cited

U.S. PATENT DOCUMENTS

| 5,262,316 | A | * | 11/1993 | Engler et al. | ............... | 800/294 |
| 5,648,267 | A | * | 7/1997 | Reff | ............... | 435/320.1 |
| 6,051,409 | A | * | 4/2000 | Hansen et al. | ............... | 800/278 |
| 6,306,636 | B1 | * | 10/2001 | Haselkorn et al. | ............... | 435/232 |

OTHER PUBLICATIONS

Deffaud, Clarence, et al. (2000) "Characterization of an Internal Ribosomal Entry Segment in the 5' Leader of Murine Lukemia Virus env RNA" *Journal of Virology 74* (2): 846-850.
Fiaschi, Tania, et al. (2000) "The Inhibitory Effect of the 5' Untranslated Region of Muscle Acylphosphatase mRNA on Protein Expression is Relieved During Cell Differentiation", *FEBS Letters 473*: 42-46.
Geballe, Adam P., et al. (1988) "Translational Control of Cytomegalovirus Gene Expression is Mediated by Upstream AUG Codons", *Journal of Virology 62 (9)*; 3334-3340.
Sella, Osnat et al. (1999) "Differentiation-Induced Internal Translation of c-sis mRNA: Analysis of the cis Elements and Their Differentiation-Linked Binding to the hnRNP C Protein", *Molecular and Cellular Biology 19 (8)* : 5429-5440.
Sarrazin, Sandrine, et al. (2000) "Negative and Translation Termination-Dependent Positive Control of FLI-1 Protein Synthesis by Conserved Overlapping 5' Upstream Open Reading Frames in Fli-1 m RNA", *Molecular and Cellular Biology 20 (9)* : 2959-2969.

Cazzola, Mario, et al. (2000) "Translational Pathophysiology: A Novel Molecular Mechanism of Human Disease", *Blood 95 (11)*: 3280-3288.
Rimbault, B., et al. (2000) "Identification of the Initiation Condon for the *atpB* Gene in *Chlamydomonas* Chlotoplasts Excludes Translation of a Precursor Form of the β Subunit of the ATP Synthase", *Mol Gen Genet 264*: 486-491; and.
Kozak, Marilyn (2000) "Do the 5' Untranslated Domains of Human cDNAs Challenge the Rules for Initiation of Translation (or is it Versa)?", *Genomics 70* : 396-406.
Pain, V.M. (1986), "Initiation of Protein Synthesis in Mammalian Cells", Biochem. J. 235: 625-637.
Modave, K. (1985, "Eukaryotic Protein Synthesis", Ann. Rev. Biochem. 54: 1109-1149.
Kozak, M. (1986), "Point Mutations Define a Sequence Flanking the AUG Initiator Codon that Modulates Translation by Eukaryotic Ribosomes", Cell. 44: 283-292.
Sonenberg, N. (1990), Poliovirus Translation, Curr. Top. Micro. And Imm. 161: 23-47.
Carrington, J.C. and Freed, D.D. (1990), "Cap-Independent Enhancement of Translation by a Plant Potyvirus 5' Nontranslated Region", J. of Vir. 64 : 1590-1597.
Jackson et al. (1990), "The Novel Mechanism of Initiation of Picornavirus RNA Translation", TIBS 15: 477-483.
Kinzler et al. (1987), "Identification of an Amplified, Highly Expressed Gene in a Human Glioma", Science 236: 70-73.
Roberts et al. (1989), "Amplification of the gli Gene in Childhood Sarcomas", Cancer Res. 49: 5407-5413.
Stein et al. (1999), "GLI Gene Expression in Bone and Soft Tissue Sarcomas of Adult Patients Correlates with Tumor Grade", Cancer Res. 59: 1890-1895.
Ingham, P.W. (1998), "Transducing Hedgehog: The Story so Far", EMBO J. 17: 3505:3511.

(Continued)

*Primary Examiner*—Terry McKelvey
(74) *Attorney, Agent, or Firm*—Scully, Scott, Murphy & Presser

(57) ABSTRACT

The present invention provides a method for modulating expression of a genetic sequence by introducing, creating or deleting one or more pseudo-translation initiation sites in the nucleotide sequence of an mRNA, upstream of the authentic translation initiation site of an open reading frame. Expression of the genetic sequence can be further modulated by introducing, creating or removing Kozac or Kozac-like sequences proximal to the pseudo-translation initiation site(s). Moreover, expression can be manipulated by the introduction, creation or removal of a termination signal prior to the authentic translation initiation site or after this site but in a different reading frame relative to the reading frame determined by the authentic translation initiation site. Nucleic acid molecules useful for practicing the present methods are also provided. The present invention further provides a method for detecting a disease condition associated with a particular level of expression of a gene or other genetic sequence.

22 Claims, 23 Drawing Sheets

OTHER PUBLICATIONS

Johnson, R.L. and Scott, M.P. (1998), "New Players and Puzzles in the Hedgehog Signaling Pathway", Curr. Opin. Genet. Dev. 8: 450-456.

Ruiz T. Altraba, A. (1999), "The Works of GLI and the Power of Hedgehog", Nature Cell Biol. 1: 147-148.

Kinzler et al. (1998), The GLI Gene is a Member of the Kruppel Family of Zinc Finger Proteins, Nature 332: 371-374.

Ruppert et al. (1988), "The GLI-Kruppel Family of Human Genes", Mol. Cell. Biol. 8: 3104-3113.

Walterhouse et al. (1993) "gli, a Zinc Finger Transceiption Factor and Oncogene, is Expressed During Normal Mouse Development", Dev. Dyn. 196: 91-102.

Hui et al. (1994), "Expression of three Mouse Homologs of the Drosophila Sengment Polarity Gene cubitus interruptis, Gli, Gli-2 and Gli-3, in Ectoderm- and Mesoderm-Derived Tissues Suggests Multiple Roles during Postimplantation Development", Dev. Biol. 162: 402-413.

Marigo et al. (1996), "Sonic Hedgehog Differentially Regulates Expression of GLI and GLI3 during Limb Development", Dev. Biol. 180: 273-283.

Lee et al. (1997), "Gli1 is a Target of Sonic Hedgehog that Induces Ventral Neural Tube Development", Development 124: 2537-2552.

St-Jacques et al. (1998), "Sonic Hedgego Signaling is Essential for hair Development", Curr. Biol. 8: 1058-1068.

Chiang et al. (1999), "Essential Role for Sonic hedgehog during Hair Follicle Morphogenesis", Dev. Biol. 205: 1-9.

Gailani et al. (1996), The Role of the Human Homologue of Drosophila Patched in Sporadic Basal Cell Carcinomas, Nat. Genet. 14: 78-81.

Hahn et al. (1996) "Mutations of the Human Homolog of Drosophila Patched in the Nevoid Basal Cell Carcinoma Syndrome", Cel 85: 841-851.

Johnson et al. (1996), "Human Homolog of patched. a candidate Gene for the Basal Cell Nevus Syndrome", Science 272: 1668-1671.

Fan et al. (1997), "Induction of Basal Cell Carcinoma Features in Transgenic Human Skin Expressing Sonic Hedgehog", Nat. Med. 3: 788-792.

Oro et al. (1997), " Basal Cell Carcinomas in Mice Overexpressing Sonic Hedgehog"; Science 276: 817-821.

Xie et al. (1998), "Activating Smoothened Mutations in Sporadic Basal Cell-Cacinoma"; Nature 391 90-92.

Dahmane et al. (1997), "Activation of the Transcription Factor Gli1 and the Sonic Hedgehog Signalling Pathway in Skin Tumours", Nature 389: 876-881.

Ruppert et al. (1991 "The Zinc Finger Protein GLI Transforms Primary Cells in Cooperation with Adenovirus E1A", Mol. Cell. Biol., 11: 1724-1728.

Reifenberger et al. (1998), "Missense Mutations in SMOH in Sporadic Basal Cell Carcinomas of the Skin and Primitive Neuroectodermal Tumors of the Central Nervoius System", Cancer Res. 58: 1798-1803.

Gnali, et al. (1999), "Gli1 Protein is Expressed in Basal Cell Carcinomas Outer Root Sheath Keratinocytes and a Subpopulation of Mesenchymal Cells in Normal Human Skin", Invest. Dermatol 113: 595-599.

Motoyama, et al. (1998) "Essential Function of Gli2 and Gli3 in the Formation of Lung, Tachea and Oesophagus", Nat. Genet., 20: 54-47.

Dai, et al. (1999), "Sonic Hedgehog-induced Activation of the Gli1 Promoter Is Mediated by GLI3", J. Biol. Chem. 274: 8143-8152.

Ruiz I. Altaba, A. (1999), "Gli Proteins Encode Context-Dependent Positive and Negative Functions" Implications for Development and Disease, Development 126: 3205-3216.

Sasaki, et al. (1999), "Regulation of Gli2 and Gli3 Activates by Amino-Terminal Repression Domain: Implication of Gli2 and Gli3 as Primary Mediators of Shh Signalling", Development 126: 3915-3924.

Altschul et al. (1997), "Gapped BLAST and PSI-BLAST: A New Generation of Protein Database Search Programs", Nucl. Acids Res. 25: 3389.

Ausubel et al. "Current Protocols in Molecular Biology", John Wiley & Sons, Inc., 1994-1998, "The Polymerase Chain Reaction", Chapter 15.

Boukamp, et al., (1988), "Normal Keratinization in a Spontaneously Immortalized Aneuploid Human Keratinocyte Cell Line", L. Cell. Biol. 106: 761-771.

Gluzman, Y. (1981), "SV40-Transformed Simian Cells Support the Replication of Early SV40 Mutants", Cell 23: 175-182.

Liu, et al. (1998) "Characterization of the Promotor Region and Genomic Organization of GLI, a Member of the Sonic Hedgehog-Patched Signling Pathway", Gene 209:1-11.

Janssen and Gardner (1989), "Localized Transient Expression of GUS in Leaf Discs Folloeing Cocultivation with Agrobacterium", Plant Mol. Biol. 14: 61-72.

Hood et al. (1986) "The Hypervirulence of Agrobacterium Tumefaciens A281 is Encoded in a Region of pTIB0542 Outside of T-DNA", J. Bacterol. 168: 1291-1301.

Hoekema et al. (1983), "A Binary Plant Vector Strategy Based on Separation of Vir- and T-region of the Agrobacterium Tumefaciens Ti-plasmid", Nature 303: 179-180.

Konez and Schell, (1986) "The Promotor of $_L$-DNA Gene 5 Controls the Issue-Specific Expression of Chimaeric Genes Carried by a Novel Type of Agrobacterium Binary Vector", Mol. Genet. 204: 383-396.

Potrykus et al. (1985) "Direct Gene Transfer to Cells of a Graminaceiuos Monocot", Mol. Gen.Genet. 199:183.

Stalker et al. (1988), "Herbicide Resistance in Transgenic Plants Expressing a Bacterial Detoxification Gene", Science 242: 419.

Thillet al. (1998), "Site-directed Mutagenesis of Mouse Dihydrofolate Reductase", J. Biol. Chem. 263: 12500.

Prasher et al. (1985), "Cloning and Expression of the CDNA Coding for Aeguorin, a Bioluminescent Calcium-Binding Protein", Biochem. Biophys. Res. Comm. 126: 1259.

Niedz et al. (1995) "Green Fluorescent Protein: An In vivo Reporter of Plant Gene Expression", Plant Cell Reports 14: 403.

Ow et al. (1986), "Transient and Stable Expression of the Firefly Luciferase Gene in Plant Cells and Transgenic Plants", Science 234: 856.

Katz et al. (1983), "Cloning and Expression of the Tyrosinase Gene from Streptomyces Antibioticus in Streptomyces Lividans", J. Gen. Microbiol. 129: 2703.

Zukowsky et al, (1983), "Chromogenic Identification of Genetic Regulatory Signals in *Bacillus subtilis* Based on Expression of a Cloned Pseudomonas Gene", Proc. Natl. Acad. Sci. USA 80: 1101.

Bonner and Laskey (1974), "A Film Detection Method forTritium-Labelled Porteins and Nucleic Acids in Polyacrylamide Gels", Eur. J. Biochem. 46: 83.

Marmur and Doty (1962), "Determination of the Base Composition of Deoxyribonucleic Acid from its Thermal Denaturation Temperature", J. Mol. Biol. 5: 109.

Ferrari M. (1962), "Polyoma Transformation of Hamster Cell Clones—an Investigation of Genetic Factors Affecting Cell Competence", Virology 16: 147-151.

Zuker, M. (1989), "On Finding All Suboptimal Foldings of an RNA Molecule", Science 244: 48-52.

Heyden, et al. (1994) "Application of Cantharidin or 12-O-Tetradecanoylphorbol-13-Acetate on Mouse Epidermis Induces a Cell Population Shift that Causes Altered Keratin Distribution", Differentiation 57: 187-193.

Lazo et al. (1991), "A DNA Transformation-Competent Arabidopsis Genomic Library in Agrobacterium", Biotechnology 9: 963-967.

Hinchee et al. (1998), "Production of Transgenic Soybean Plants Using Agrobacterium-Mediated DNA Transfer", Biotech 6: 915.

Sutcliffe, (1978), "Nucleotide Sequences of the Ampicillin Resistance Gene of *Escherichia coli* Plasmid pBR322", Proc. Natl. Acad. Sci. USA 75: 3737.

Dellaporta et al. (1988), "Chromosome Structure and Function", pp. 263-282.

Ikuta et al. (1990), "The α-Amylase Gene as a Marker for Gene Cloning: Direct Screening of Recombinant Clones", Biotech 8: 241.

Sambrook et al. (1982) Molecular Cloning: A Laboratory Manual, Cold Spring Harbor, NY, USA.

* cited by examiner

|          | 1 |
|----------|---|
| α-UTR | agtttccagccctggaccacgcatcccgagcaccgcgccccgacggaggtctctttgtcc |
| β-UTR | agtttccagccctggaccacgcatcccgagcaccgcgccccgacggaggtctctttgtcc |
| γ-UTR | agtttccagccctggaccacgcatcccgagcaccgcgccccgacggag------------ |

|          | 1a |
|----------|----|
| α-UTR | gcgcctctcccacatactagaaatctctccctttcttgaggttgggatgaagaagcagtt |
| β-UTR | gcgcctctcccacatactagaaatctctccctttcttgaggttgggatgaagaagcagtt |
| γ-UTR | ------------------------------------------------------------ |

| α-UTR | gggacggccagctggaggtctgcgtggtagagggaactccagagactgtggatccccaag |
|-------|---|
| β-UTR | gggacggccagctggaggtctgcgtggtagagggaactccag------------------ |
| γ-UTR | ------------------------------------------------------------ |

|          | 1b |
|----------|----|
| α-UTR | actgaacggctgcttctgcccactctttgggatgtttcttcttaaggaagctgaaaaacg |
| β-UTR | ------------------------------------------------------------ |
| γ-UTR | ------------------------------------------------------------ |

| α-UTR | ttattgatttccatgaccagtttctgagatgagggttagaggtcccctcatccttccctg |
|-------|---|
| β-UTR | -------------------------------gtccctcatccttccctg |
| γ-UTR | -------------------------------gtccctcatccttccctg |

|          | 2 |
|----------|---|
| α-UTR | agacgccATGTTCAATCCAATGACTCCGCC |
| β-UTR | agacgccATGTTCAATCCAATGACTCCGCC |
| γ-UTR | agacgccATGTTCAATCCAATGACTCCGCC |

Figure 1A

```
Human  tctgtgtatctctgtctcagggaaccgtgtgggtctttgtctccgcctctcccatatattag
Mouse  ------------------------gt--ctctttgtccgcgcctcctcccacatactag
                               *  *    ******** ******** ****** *** ***  ***
```

```
Human  aaatatcttactttcatgcggttaagttgagagaggctggaggatggctagctggatgtc
Mouse  aaatctctcccttctttgaggttgggatgggatgaagaagcagttgggatggccagctggaggtc
       ****  ** * ** *** ****   * *        ** **   *** ****   ******** *
```

```
Human  tgcgttgtagagaggtaacccccag
Mouse  tgcgtggtagag-gg-aactccag
       *****  ***** **   ** ****
```

Figure 4C

EXPRESSION MODULATING SEQUENCES

CROSS REFERENCE TO RELATED APPLICATION

This application claims priority from U.S. Provisional Application No. 60/211,159 filed on Jun. 13, 2000.

FIELD OF THE INVENTION

The present invention relates generally to a method for modulating expression of a genetic sequence and to agents useful for same. More particularly, the present invention provides a means for modulating expression of a genetic sequence by introducing, creating or deleting one or more pseudo-translation initiation sites in the nucleotide sequence of an mRNA, upstream, i.e. 5', of the authentic translation initiation site of an open reading frame. The present invention provides further modulation of expression by introducing, creating or removing Kozac or Kozac-like sequences genetically proximal to the pseudo-translation initiation site(s). Modulation of expression is further manipulated by the introduction, creation or removal of a termination signal prior to the authentic translation initiation site or after this site but in a different reading frame relative to the reading frame determined by the authentic translation initiation site. The present invention further provides genetic agents including a plurality of nucleic acid molecules each with a predetermined number of pseudo-translation initiation sites and/or pseudo-open reading frames (ORFs) wherein each sequence influences or otherwise contributes to a particular level of expression for genetic sequences operably linked or associated to the 3' end of said nucleic acid molecules. The level of expression of the genetic sequences is commensurate with a selected nucleic acid molecule which becomes a 5' untranslated or leader region (5'UTR) of said genetic sequence. The present invention still further contemplates a method for detecting a disease condition such as cancer or a proliferative disorder wherein the disease condition is associated with a particular level of expression of a gene or other genetic sequence. Such a method is predicated in part on identifying a particular 5'UTR or 5'UTR-encoding sequence or the level of pseudo-translation initiation sits therein alone or in combination with pseudo-ORFs which provides an indication as to the likely level of expression of said gene or genetic sequences. The ability to modulate the level of expression of a genetic sequence is useful, inter alia, for gene therapy applications and for expressing traits at selective levels in plants. Such traits include herbicide and pesticide resistance.

BACKGROUND OF THE INVENTION

Bibliographic details of the publications numerically referred to in this specification are collected at the end of the description.

Reference to any prior art in this specification is not, and should not be taken as, an acknowledgment or any form of suggestion that this prior art forms part of the common general knowledge in Australia or any other country.

For most eukaryotic mRNAs, translation initiates with the binding of the cap binding protein to the mRNA cap structure. This is then followed by the binding of several other translation factors, as well as the 43S ribosome pre-initiation complex. This complex travels down the 5' region of the mRNA molecule while scanning for an initiation codon in an appropriate sequence context. Once the initiation codon has been found and with the addition of the 60S ribosomal subunit, the complete 80S initiation complex initiates protein translation (1,2,3). A second class of mRNAs have been identified which possess translation initiation features different from those described above. Translation from these mRNAs initiates in a cap-independent manner and is believed to initiate with the ribosome binding to internal portions of the leader sequence (4,5,6,7). Most 5' untranslated leader sequences are very A,U rich and are predicted to lack any significant secondary structure. One of the early steps in translation initiation is the relaxing or unwinding of the secondary mRNA structure (6). Messenger RNA leader sequences with negligible secondary structure may not require this additional unwinding step and may, therefore, be more accessible to the translation initiation components. The ability of a leader sequence to interact with translational components may play a key role in affecting levels of subsequent gene expression.

In work leading up to the present invention, the inventors sought to identify 5' leader sequences which might be responsible for the regulation of gene expression. The gene initially chosen for investigation was the GLI1 gene.

The gene GLI1 was originally isolated as a highly amplified gene in a malignant glioma (8) and subsequently implicated in the development of other tumor types, including liposarcoma, rhabdomyosarcoma, osteosarcoma and astrocytoma (9,10). It has been shown that GLI1 encodes a transcription factor which is a downstream nuclear component of the Sonic Hedgehog/Patched (SHH/PTC) signalling pathway (11,12,13). This pathway is evolutionarily conserved and found to operate in a number of tissues during vertebrate development and especially in regions involving mesoderm-ectoderm interactions (14,15,16,17). Intercellular signalling by this pathway is initiated when SHH (a secreted protein) binds to PTC (a cell-surface transmembrane protein), resulting in the activation of GLI1 in the nucleus and subsequent expression of target genes. Over-expression of SHH has been shown to upregulate GLI1 in the chick limb buds and in the epidermal ectoderm of frog embryos (18,19) whereas, GLI1 expression is undetectable in SHH null embryos (20,21), confirming that SHH signalling regulates GLI1 expression.

The discovery of PTC mutations in familial and sporadic forms of basal cell carcinoma (BCC), the most common skin cancer, has associated aberrant signalling of the SHH/PTC pathway with the formation of these tumors (22,23,24). The genetic data are supported by experimental evidence showing that over-expression of SHH and other components of this pathway results in the induction of BCCs in transgenic mice and transgenic human skin (25,26,27). Over-expression of GLI1 produces BCC-like lesions in transgenic tadpoles (28) and transforms rodent epithelial cells in cooperation with adenovirus EIA (29) indicating that unregulated expression of GLI1 is oncogenic. Studies have shown that GLI1 expression is greatly increased in BCCs but not in the surrounding normal tissue consistent with a central role in tumor formation (28,30,31).

In addition to GLI1, two other isoforms have been identified in vertebrates (termed •GLI2• and •GLI3•), each encoded by a separate gene (15,17). The GLI genes are highly expressed during development and their expression profiles correlate with organogenesis but show only low level expression in most adult tissues (14,16,17). In the skin, GLI1 expression is readily observed in the epidermal compartment of the developing hair follicle whereas GLI2 and GLI3 transcripts were detected in the surrounding mesenchyme (17,28,31). The role of each GLI in mediating the SHH signal is not yet clear but recent gene ablation studies on GLI2 and GLI3 have shown overlapping roles and indicated some functional redundancy (32). A number of studies have indicated that GLI1 encodes a transcriptional activator, whereas GLI2 and GLI3 encode factors which can act as both an activator or a repressor depending on specific post-translational modifications (33,34,35). Interestingly, GLI2 and GLI3 are now thought to regulate GLI1 transcription directly by binding to the GLI1 promoter (33,35).

In accordance with the present invention, the subject inventors have now identified alternative 5'UTRs of GLI1 transcripts in mammalian tissues which are generated by exon skipping and which confer marked differences in translation efficiency. The inventors• results indicate that post-transcriptional regulation of GLI1 is mediated by the 5'UTR generated through exon skipping and show an association of the most efficiently translated 5'UTR transcript with BCC and cellular proliferation.

More particularly, the inventors surprisingly determined that by altering the number of sequence elements corresponding to pseudo-translation initiation sites, i.e. RUG or RTG triplets (where R is A or G), within the leader sequence of a nucleic acid molecule and prior to the authentic translation initiation site alone or in combination with termination signals in the 5' UTR or in a different reading frame within the coding sequence and/or in the 3' UTR, it is possible to modulate gene expression. In a further determination, the present inventors identified that altering nucleotide sequences proximal to the RUG or RTG triplets within a leader sequence also permitted the regulation of gene expression. Thus, the subject inventors have developed a method for the regulation of gene expression in eukaryotic cells including animal cells and plant cells. Furthermore, the identification of expression modulating sequences enables determination to be made as to expected levels of gene expression such as in certain disease conditions or to express traits at selective levels in animal and plant cells.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims. The present invention is predicated in part on the proposition that the level of expression of a genetic sequence is proportional or otherwise dependent or influenced by the number of pseudo-translation sites in the 5' leader sequence upstream of the authentic translation initiation site alone or in combination with pseudo-open reading frames (pseudo-ORFs) in or beginning in the 5' leader sequence. A pseudo-ORF is also known as an upstream ORF (uORF). The authentic translation initiation site is regarded as the RTG or RUG triplet, where R is A or G, at the beginning of an open reading frame or coding sequence. A pseudo-translation initiation site is regarded as an RTG or RUG located in the 5' nucleotide sequence upstream of the authentic translation initiation site. The term "pseudo" is used to distinguish these sites or triplets from the authentic RTG or RUG triplet. In accordance with the present invention, it is proposed that elevated expression of a genetic sequence, which comprises an open reading frame and an authentic translation initiation site and a leader sequence upstream of said authentic translation initiation site, occurs when RTG/RUG triplets are removed or destroyed in the upstream sequence. Conversely, expression is reduced by introducing or creating pseudo-translation initiation sites. Furthermore, pseudo-ORFs may be present or created or removed by the introduction of one or more termination signals within the 5' leader sequence or in a different reading frame within the coding sequence or within the 3'UTR.

One of the many implications of the present invention is the ability to design genetic elements which permit the controlled expression of a genetic sequence, to which they are operably connected or associated, to expected levels in animal, mammalian (including human) and plant cells. For example, a plurality of genetic elements are produced each with a different number of pseudo-translation initiation triplets, i.e. RTG or RUG where R is A or G. Where high expression of a genetic sequence is required, a genetic element is selected with no or few pseudo-translation initiation sites and this is fused to the 5' end of the genetic sequence or inserted into a 5' leader sequence associated with said genetic sequence. When the resulting construct is operably linked to a promoter, higher expression of the genetic sequence is expected relative to a genetic element comprising a greater number of pseudo-translation initiation sites. Modulation of expression further comprises the introduction or removal of termination signals to create pseudo-ORFs in or beginning in the 5' leader sequence and terminating in the 5' leader sequence, within the main ORF (authentic ORF) but in a different reading frame and/or in a 3'UTR.

A plurality of genetic constructs may also be generated each comprising a genetic element having a predetermined number of pseudo-translation initiation sites. When expression of a genetic sequence is required, the genetic sequence is ligated into the construct downstream of the genetic element.

The identification of genetic markers of expression, i.e. the number of pseudo-translation initiation sites and optionally pseudo-ORFs, further enables the determination of the likely level of expression of a gene under investigation such as a gene involved in disease including cancer or a proliferative disorder. Furthermore, various traits may be expressed at selective levels in animal and plant cells The present invention provides, therefore, a method for diagnosing or predicting the likely level of expression of a target gene based on the number of pseudo-translation initiation triplets in its 5' sequence, upstream of the authentic translation initiation site and/or the number of pseudo-ORFs in the target gene in animal and plant cells.

Accordingly, the present invention contemplates for modulating the expression of a genetic sequence wherein said sequence comprises an ORF having an RTG or RUG wherein R is A or G corresponding to an authentic translation site of said ORF and a nucleotide sequence 5' of said authentic translation start site, said method comprising introducing or removing one or more RTG or RUG triplets in said 5' nucleotide sequence upstream of said authentic translation initiation site such that upon expression of said genetic sequence, there is a respective decrease or increase in the level of expression.

The modulation of expression of a subject genetic sequence may also involve manipulating nucleotide sequences proximal to a pseudo-translation initiation site to introduce, create or remove Kozac or Kozac-like sequences and/or introducing or removing termination signals to create or destroy pseudo-ORFs in the nucleotide sequence. The presence of such a sequence is proposed to enhance the function of a pseudo-translation initiation site thereby further decreasing expression of a downstream genetic sequence.

Another aspect of the present invention contemplates a method for modulating the expression of a genetic sequence wherein said sequence comprises an ORF having an RTG corresponding to an authentic translation initiation site of said ORF where R is A or G and a nucleotide sequence 5' of said authentic translation initiation site, said method comprising introducing or removing one or more RTG triplets in said 5' nucleotide sequence upstream of said authentic translation initiation site such that upon expression of said genetic sequence, there is a respective decrease or increase in the level of expression.

Yet another aspect of the present invention further contemplates a method for modulating the expression of a genetic sequence wherein said sequence comprises an ORF having an RUG corresponding to a translation initiation site of said ORF where R is A or G and a nucleotide sequence 5' of said translation start site, said method comprising introducing or removing one or more RUG triplets in said 5' nucleotide sequence upstream of said authentic translation initiation site such that upon expression of said genetic sequence, there is a respective decrease or increase in the level of expression.

Still another aspect of the present invention contemplates, therefore, a method for facilitating increased or elevated expression of a genetic sequence wherein said sequence comprises an ORF having an RTG or RUG wherein R is A or G corresponding to an authentic translation initiation site of said ORF and a nucleotide sequence 5' of said authentic translation initiation site, said method comprising removing one or more RTG or RUG triplets in said 5' nucleotide sequence upstream of said authentic translation initiation site such that upon expression of said genetic sequence, there is an increase in the level of expression relative to expression of the genetic sequence in the absence of removal of any RTG or RUG triplet.

Still yet another aspect of the present invention provides a method for facilitating increased or elevated expression of a genetic sequence wherein said sequence comprises an ORF having an RTG wherein R is A or G corresponding to an authentic translation initiation site of said ORF and a nucleotide sequence 5' of said authentic translation initiation site, said method comprising removing one or more RTG triplets in said 5' nucleotide sequence upstream of said authentic translation initiation site such that upon expression of said genetic sequence, there is an increase in the level of expression relative to expression of the genetic sequence in the absence of removal of any RTG triplet.

Even yet another aspect of the present invention relates to a method for facilitating increased or elevated expression of a genetic sequence wherein said sequence comprises an ORF having an RUG wherein R is A or G corresponding to an authentic translation initiation site of said ORF and a nucleotide sequence 5' of said authentic translation initiation site, said method comprising removing one or more RUG triplets in said 5' nucleotide sequence upstream of said authentic translation initiation site such that upon expression of said genetic sequence, there is an increase in the level of expression relative to expression of the genetic sequence in the absence of removal of any RUG triplet.

A further aspect of the present invention contemplates a method for facilitating decreased or reduced expression of a genetic sequence wherein said sequence comprises an ORF having an RTG or RUG where R is A or G corresponding to an authentic translation initiation site of said ORF and a nucleotide sequence 5' of said authentic translation initiation site, said method comprising introducing or creating one or more RTG or RUG triplets in said 5' nucleotide sequence upstream of said authentic translation initiation site such that upon expression of said genetic sequence there is a decrease in the level of expression relative to expression of the genetic sequence in the absence of introducing or removing any RTG or RUG triplets.

Another aspect of the present invention contemplates, therefore, a method for modulating the expression of a genetic sequence wherein said sequence comprises an ORF having an RTG or RUG corresponding to an authentic translation initiation site and a nucleotide sequence 5' of said authentic translation start site comprising the sequence:

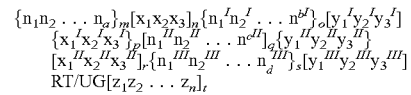

RT/UG$[z_1 z_2 \ldots z_n]_t$ wherein:

RT/UG is the authentic translation initiation site and R is A or G;

n, $n^I$, $n^{II}$ and $n^{III}$ are nucleotides selected from A, T or U, C or G or I;

$\{n_1 n_2 \ldots n_a\}_m$, $\{n_1^I n_2^I \ldots n_b^I\}_o$, $\{n_1^{II} n_2^{II} \ldots n_c^{II}\}_p$ and $\{n_1^{III} n_2^{III} \ldots n_d^{III}\}_s$ represent nucleotide sequences of a, b, c or d nucleotides in length and where each of n, $n^I$, $n^{II}$ and $n^{III}$ may be the same or different and its position is indicated by the subscript numeral $_1, _2, \ldots$;

$[z_1 z_2 \ldots z_n]$ represents a translation termination signal within an authentic ORF but not in the same reading frame as said authentic ORF;

each of m, n, o, p, q, r or s may be the same or different and each is 0 or 1 or if there is a repeat or multiple repeats, from about 2 or about 10;

t is 0, 1 or >1;

each of $[x_1 x_2 x_3]_n$, $[x_1^I x_2^I x_3^I]_p$ and $[x_1^{II} x_2^{II} x_3^{II}]_r$ is selected from the triplet RTG, RUG, RYG, $RTY^I$, $RY^{II}G$, $RUY^{III}$, ATG, GTG, AUG and GUG where R is A or G, and each of Y, $Y^I$, $Y^{II}$ and $Y^{III}$ may be the same or different and each is a nucleotide with the proviso that Y is not T, $Y^I$ is not G, $Y^{II}$ is not U and $Y^{III}$ is not G;

each of $[y_1^I y_2^I y_3^I]$, $[y_1^{II} y_2^{II} y_3^{II}]$ and $[y_1^{III} y_2^{III} y_3^{III}]$ represents a translation termination signal; and said method comprising altering the nucleotide triplets $[x_1 x_2 x_3]_n$, $[x_1^I x_2^I x_3^I]_p$ and/or $[x_1^{II} x_2^{II} x_3^{II}]_r$ to introduce or remove an RTG or RUG to thereby respectively decrease or increase the level of expression of said genetic sequence.

Yet another aspect of the present invention provides a nucleotide sequence for use in modulating the expression of a genetic sequence wherein said genetic sequence comprises a coding region comprising a translation initiation site and optionally a 5' leader sequence such that said nucleotide sequence comprising a predetermined number of RTG or RUG triplets such that upon operable linkage to the 5' end of the genetic sequence, the level of expression of said genetic sequence is determined by the number of RTG/RUG triplets.

Still another aspect of the present invention further provides a plurality of nucleotide sequences each comprising a predetermined number of RTG or RUG triplets wherein R is A or G wherein said predetermined number is from 0 to about 100 and preferably from about 0 to about 50 and even more preferably from about 0 to about 15 such that to facilitate expression of a genetic sequence to a particular level, a particular nucleotide sequence is selected and inserted or placed between a promoter and said genetic sequence such that the promoter is operably linked to said genetic sequence and wherein the level of expression is inversely functionally associated with the number of RTG or RUG triplets.

Still yet another aspect of the present invention is directed to an isolated nucleic acid molecule comprising a nucleotide sequence encoding a 5' mRNA sequence, said mRNA sequence selected from SEQ ID NO:1 to SEQ ID NO:5 or a nucleotide sequence having at least 60% similarity to one or more of SEQ ID NO:1 to SEQ ID NO:5 or a nucleotide sequence capable of hybridizing to one or more of SEQ ID NO:1 to SEQ ID NO:5 or a complementary form thereof under low stringency conditions wherein said nucleotide sequence is capable of influencing the level of expression of a genetic sequence operably linked to said nucleotide sequence.

Even yet another aspect of the present invention provides an isolated nucleic acid molecule comprising a nucleotide sequence encoding a non-translated mRNA sequence, said nucleotide sequence selected from SEQ ID NO:33 to SEQ ID NO:36 or a nucleotide sequence having at least 60% similarity to one or more of SEQ ID NO:33 to SEQ ID NO:36 or a nucleotide sequence capable of hybridizing to one or more of SEQ ID NO:33 to SEQ ID NO:36 or complementary forms thereof under low stringency conditions wherein said nucleotide sequence is capable of influencing the level of expression of a genetic sequence operably linked to said nucleotide sequence.

A further aspect of the present invention contemplates a genetic construct comprising a promoter linked to a genetic element and one or more restriction endonuclease sites to facilitate insertion of a nucleotide sequence to be expressed by said promoter wherein said genetic element comprises a predetermined number of pseudo-translation initiation RTG/RUG triplets wherein R is A or G such that the level of expression of said nucleotide sequence by said promoter is inversely functionally associated with the number of RTG/RUG triplets in said genetic element.

Another aspect of the present invention contemplates a method for modulating expression of a genetic sequence, wherein said genetic sequence comprises an ORF with an authentic translation initiation site and further comprising a sequence upstream of said authentication translation initiation site where said method comprises introducing, creating or removing one or more pseudo-translation initiation triplets having the structure RWG wherein R is A or G and W is T or U in combination with introducing, creating or removing a Kozac or Kozac-like sequence proximal to said RWG such that the number of RWG triplets and Kozac or Kozac-like sequences is inversely functionally associated with expression of said genetic sequence.

In all the above aspects, the genetic sequence may be further manipulated to introduce or remove termination signals thereby creating or destroying pseudo-ORFs within the genetic sequence.

Another aspect of the present invention provides an isolated nucleic acid molecule comprising a nucleotide sequence encoding a non-translated mRNA sequence, said nucleotide sequence selected from SEQ ID NO:59 or 60 or a nucleotide sequence having at least 60% similarity to one or more of SEQ ID NO:59 or 60 or a nucleotide sequence capable of hybridizing to one or more of SEQ ID NO:59 or 60 or complementary forms thereof under low stringency conditions wherein said nucleotide sequence is capable of influencing the level of expression of a genetic sequence operably linked to said nucleotide sequence.

A summary of sequence identifiers used throughout the subject specification is provided below.

SUMMARY OF SEQUENCE IDENTIFIERS

| SEQUENCE ID NO: | DESCRIPTION |
|---|---|
| 1 | Mα-UTR mRNA |
| 2 | Mβ-UTR mRNA |
| 3 | Mγ-UTR mRNA |
| 4 | Hβ-UTR mRNA |
| 5 | Hγ-UTR mRNA |
| 6 | Synthetic |
| 7 | Synthetic |
| 8 | Synthetic |
| 9 | Synthetic |
| 10 | Synthetic |
| 11 | Synthetic |
| 12 | DNA Primer for mouse GLI exon 1 |
| 13 | DNA Primer for mouse GLI exon 2 |
| 14 | DNA Primer for mouse GLI exon 1 with restriction site for NheI |
| 15 | DNA Primer for mouse GLI exon 2 with restriction site for AgeI |
| 16 | DNA primer for mouse RACE1 exon 4 |
| 17 | DNA primer for mouse RACE2 exon 2/3 |
| 18 | DNA primer for mGliF1a exon 1a |
| 19 | DNA primer for mGliMF1 |
| 20 | DNA primer for mGliMF2 |
| 21 | DNA primer for mGliMF3 |
| 22 | DNA primer for mGliMF4 |
| 23 | DNA primer for mGliMR1 |
| 24 | DNA primer for mGliMR2 |
| 25 | DNA primer for mGliMR3 |
| 26 | DNA primer for mGliMR4 |
| 27 | DNA primer for mGliF1$^{Bam}$ |
| 28 | DNA primer for mGliR2$^{Bgl}$ |
| 29 | DNA primer for mGliF1$^{Nhe}$ |
| 30 | DNA primer for mGliR2$^{Age}$ |
| 31 | DNA Primer for human GLI exon 1 |
| 32 | DNA Primer for human GLI exon 2 |
| 33 | DNA Mouse GLI UTR partial genomic sequence |
| 34 | DNA Mouse GLI UTR partial genomic sequence |
| 35 | DNA Human GLI UTR partial genomic sequence |
| 36 | DNA Human GLI UTR partial genomic sequence |
| 37 | DNA primer for GLI1 5'-SacI |
| 38 | DNA primer for GLI 3'-NcoI |
| 39 | Primer |
| 40 | Primer |
| 41 | Mα-UTR |
| 42 | Mα-UTR + 1 AUG |
| 43 | Mα-UTR + 2 AUG |
| 44 | Mα-UTR + 3 AUG |
| 45 | Mα-UTR + 4 AUG |
| 46 | Mα-UTR + 5 AUG |
| 47 | Mβ UTR + 1 AUG |
| 48 | Mβ UTR + 2 AUG |
| 49 | Mβ UTR + 3 AUG |
| 50 | Mγ UTR + 1 AUG |
| 51 | Mγ UTR + 2 AUG |
| 52 | Mγ UTR + 3 AUG |
| 53 | Hβ UTR + 1 AUG |
| 54 | Hβ UTR + 2 AUG |
| 55 | Hβ UTR + 3 AUG |
| 56 | Hγ UTR + 1 AUG |
| 57 | Hγ UTR + 2 AUG |
| 58 | Hγ UTR + 3 AUG |
| 59 | Mouse GLI1 genomic sequence (exons in bold) |
| 60 | Human GLI1 genomic sequence (exons in bold) |

DETAILED DESCRIPTION OF THE PREFERRED EMBODIMENTS

Figure 1B:
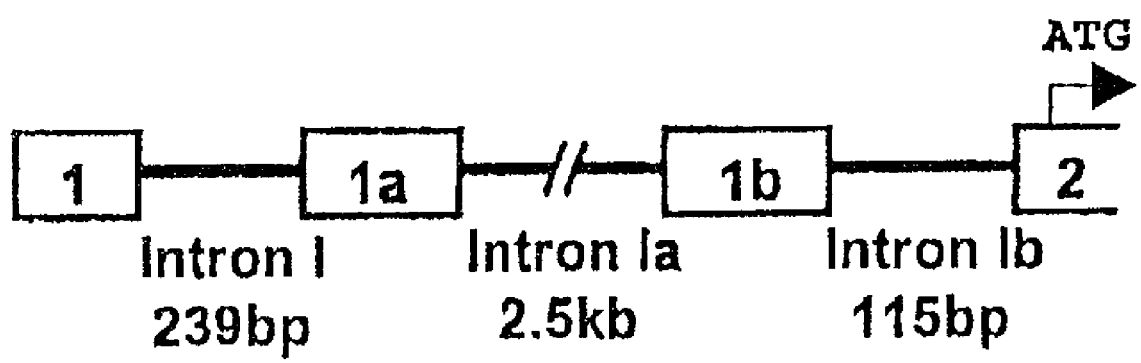
FIG. 1 is a representation of the sequence, exon composition and pre-mRNA structure of the alternative 5'UTRs of mouse GLI1. Panel A, sequence alignment of the three alternative GLI1 5'UTR variants (denoted α-UTR (SEQ ID NO: 61), β-UTR (SEQ ID NO: 62) and γ-UTR (SEQ ID NO: 63)) expressed in mouse. The novel 119 bp sequence of exon 1a is shown in bold lowercase lettering. The ATG codons denoting the beginning of uORFs are underlined and the main ORF encoding GLI1 is shown bold uppercase lettering. The intron/exon boundaries are indicated by arrows. Panel B, schematic showing the exon composition of the alternative 5'UTRs and the organization of the pre-mRNA from which they are derived. Exons are denoted by open boxes and introns by solid lines with intron size shown. The translation start site (ATG) of the main ORF is located in exon 2 and indicated by a bent arrow.
Figure 1B:
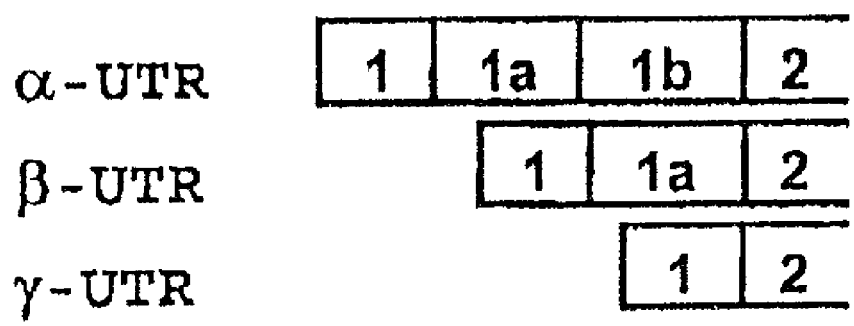

The present invention is predicated in part on the elucidation that the level of expression of a genetic sequence is related to the presence and/or number of pseudo-translation initiation sites located 5', i.e. upstream, of an authentic translation initiation start site of an open reading frame (ORF) or coding sequence and the presence or absence of a Kozac or Kozac-like sequence genetically proximal to RTG triplets in DNA or RUG in RNA where R is adenine (A) or guanine (G). Manipulation of the nucleotide sequence 5' of the authentic translation initiation site to introduce, create or remove RTG/RUG triplets and/or to introduce Kozac or Kozac-like sequences provides a means of reducing or elevating, i.e. modulating, the level of expression of a transcript of the DNA in an eukaryotic cell such as an animal (e.g. insect, fish, amphibian), mammalian (e.g. human, primate, livestock animal or laboratory test animal) or lower eukaryotic cell. The genetic sequence may be further manipulated to introduce or remove termination signals to create or destroy pseudo-ORFs within the genetic sequence. A pseudo-ORF may be located entirely within a 5'UTR or may extend into the coding region, referred to herein as the "authentic ORF" or "main ORF". In the case of the latter, there would necessarily be a stop codon not in the same reading frame as the authentic ORF. The pseudo-ORF may even extend into the 3'UTR.

The term "expression" in this context particularly encompasses translation into a translation product and in particular a polymer of two or more amino acids. The presence or absence of RTG/RUG sites and/or Kozac or Kozac-like sequences also has diagnostic value in the prediction of the likely level of expression of a particular target gene. Furthermore, a plurality of genetic elements in the form of nucleic acid molecules may be produced each with differing levels of RTG/RUG triplets and genetically proximal Kozac or Kozac-like sequences and used to generate genetic constructs conferring defined levels or predetermined expectations of levels of expression of nucleotide sequences operably linked or fused to each of the nucleic acid molecules.

Accordingly, the present invention contemplates a method for modulating the expression of a genetic sequence wherein said sequence comprises an ORF having an RTG or RUG wherein R is A or G corresponding to an authentic translation site of said ORF and a nucleotide sequence 5' of said authentic translation start site, said method comprising introducing or removing one or more RTG or RUG triplets in said 5' nucleotide sequence upstream of said authentic translation initiation site such that upon expression of said genetic sequence, there is a respective decrease or increase in the level of expression.

Reference herein to "modulating" means increasing or decreasing the level of expression of a genetic sequence. Generally, expression of a DNA sequence includes transcription to an mRNA sequence and optionally also translation of the transcript to a translation product, generally a polymer of two or more amino acids such as a peptide, polypeptide or protein. Expression of an RNA and in particular an mRNA sequence generally means translation into a translation product. Accordingly, expression covers transcription and/or translation and events including post-transcriptional and post-translational events. In a particularly preferred embodiment, expression is determined at the level of translation of an mRNA molecule.

The term "authentic" translation initiation site is used to distinguish between an RTG or RUG, where R is A or G at the beginning of the authentic (i.e. main) ORF and RTG/RUG triplets upstream of the authentic site. The upstream RTG/RUG triplets are referred to herein as "pseudo-translation initiation sites" as they may have some role in ribosome binding at that site but this is not the correct site for translation of the authentic ORF. The term "pseudo-open reading frame" or "pseudo-ORF" means a translatable region between initiation and termination signals within the 5' leader sequence or beginning in the leader sequence but terminating within the coding region downstream of the authentic translation initiation site or in the 3' region. A termination signal in the main ORF would be in a different reading frame.

The term "genetic sequence" includes a DNA or RNA and comprises an ORF having an RTG or RUG translation initiation site where R is A or G. This is regarded as the authentic translation initiation site. The genetic sequence further comprises a nucleotide sequence 5' of the authentic translation initiation site. The 5' sequence may also be referred to as a "leader sequence", "upstream sequence", "5' non-coding sequence" or 5'UTR. The genetic sequence provides information necessary to direct the transcription of a DNA molecule or the translation of an mRNA molecule. The term "genetic sequence" includes nucleotide sequences defining exons, introns, terminators, promoters including enhancers and silencers and the coding and non-coding regions of an ORF or gene. Reference herein to an "mRNA" or "messenger RNA" refers to a ribonucleic acid molecule which is generated by the transcription of a DNA sequence.

In one embodiment, the genetic sequence is DNA.

Accordingly to this embodiment, the present invention contemplates a method for modulating the expression of a genetic sequence wherein said sequence comprises an ORF having an RTG corresponding to an authentic translation initiation site of said ORF where R is A or G and a nucleotide sequence 5' of said authentic translation initiation site, said method comprising introducing or removing one or more RTG triplets in said 5' nucleotide sequence upstream of said authentic translation initiation site such that upon expression of said genetic sequence, there is a respective decrease or increase in the level of expression.

In another embodiment, the genetic sequence is RNA.

Accordingly, the present invention further contemplates a method for modulating the expression of a genetic sequence wherein said sequence comprises an ORF having an RUG corresponding to a translation initiation site of said ORF where R is A or G and a nucleotide sequence 5' of said translation start site, said method comprising introducing or removing one or more RUG triplets in said 5' nucleotide sequence upstream of said authentic translation initiation site such that upon expression of said genetic sequence, there is a respective decrease or increase in the level of expression.

The term "translation initiation site" or "initiation codon" refers to the RTG/RUG (R=A or G) that is selected as the initiating RTG/RUG for the translation of an RNA sequence comprising a translatable ORF. It is generally understood that genetic elements including nucleotides proximal to the translation initiation RTG or RUG provide part of the initiation information. Although the present invention extends to an RTG/RUG where R is A or G, the preferred R nucleotide is A. The translation initiation site may be "authentic", i.e. the correct start site of an ORF or it may be "pseudo" if located upstream of the authentic start site.

The term "open reading frame" or "ORF" refers to a sequence of nucleotide triplets between start and stop codons, uninterrupted by internal stop codons. A "triplet" refers to a series of three nucleotides. Generally, an ORF encodes a peptide, polypeptide or protein. A genetic sequence to be expressed, in accordance with the present invention, is proposed to comprise an ORF and an upstream nucleotide sequence. The level of expression is proposed to be determined by the number of RTG/RUG triplets in this upstream sequence. Furthermore, the level of expression is proposed to be influenced by the number of pseudo-ORFs within the genetic sequence. These can be created or destroyed by introducing termination signals in the 5' leader sequence or, in a different reading frame, in the coding sequence downstream of the authentic translation initiation site or in the 3' region.

As stated above, reference herein to a "5' nucleotide sequence" refers generally to a 5' leader sequence, an upstream sequence (i.e. upstream of an ORF or authentic translation initiation site) or a 5' untranslated region or 5'UTR. The term "untranslated region" or "UTR" is a term of art referring to the particular location of a genetic sequence relative to the translation initiation site. However, the use of these terms is not to exclude the possibility that some partial translation may occur in this region. The 5' leader sequence is, therefore, a genetic element located 5' to the coding region of an mRNA transcript and provides the information necessary for correct translation initiation (i.e. the selection of a translation initiation site). The 5' leader sequence is further defined as that portion of an mRNA molecule which extends from the 5' cap site to the RUG translation initiation codon. The term "cap" refers to the 7-methyl guanosine nucleotide structure present at the very 5' end of the mRNA transcript.

The term "translation" refers to the multi-step biochemical pathway of translation. The regulation of translation and protein synthesis is the basis of cellular growth and differentiation. The term "translation" further relates to cap-dependent initiation and ribosome shunting cap. Dependent translation initiation is the major translation initiation pathway in eukaryotic cells. In this process, dissociated 40S ribosomal subunits "scan" an mRNA to identify and locate the start or initiation codon. Once an initiation complex has been formed between the 40S subunit and the 5' leader sequence of the mRNA, the 60S ribosomal subunit joins the initiation complex to form the 80S ribosome. This complex is then competent to initiate translation. Ribosome shunting is another pathway of translation initiation in which ribosomes bind to the mRNA in a cap-dependant manner, however, they are capable of "jumping" over large regions of the mRNA containing RNA secondary structure, upstream RUGs and upstream (uORFs) to a specific initiator RUG. The term "translation" encompasses all such mechanisms.

Reference herein to "RTG" or "RUG" refers to a nucleotide triplet composed of deoxyribonucleotides and ribonucleotides, respectively. The symbol R referred to herein refers to a purine selected from the group of G and A. As stated above, A is the preferred R nucleotide although the present invention extends to A or G.

By "DNA" or "RNA" is meant a sequence of two or more naturally occurring deoxyribonucleotides or ribonucleotides that are covalently bonded together. The deoxyribonucleotides or ribonucleotides may be naturally occurring (i.e. A, C, T, U, G) or non-naturally occurring including modified forms of the ribonucleotides. One example of a modified RNA included within this term is phosphorothioate RNA. The term "RNA" also encompasses RNA molecules comprising a series or mixture of modified nucleotide analogues. Such modified RNA molecules provide more stable substrates for translation when introduced in to a host cell. As used herein "oligonucleotide" or "oligomer" is generic to polydeoxyribonucleotides (containing 2'-deoxy-D-ribose or modified forms thereof), i.e. DNA, to polyribonucleotides (containing D-ribose or modified forms thereof), i.e. RNA, and to any other type of polynucleotide which is an N-glycoside or C-glycoside of a purine or pyrimidine base, or modified purine or pyrimidine base. The present invention further contemplates DNA/RNA hybrids which may be transcribed by a DNA or RNA polymerase.

The present invention provides, therefore, chemically modified nucleic acid molecules including nucleic acid molecules with chemically modified bases and/or inter-base linkages which may be introduced directly into a cell, such as by way of a linear strand or strands of nucleic acid molecules and then transcribed or translated by a cell's transcription/translation machinery. Alternatively, such nucleic acid molecules may be introduced via viral constructs. Such modified forms of nucleic acid molecules may be more stable especially to exonuclease or ribonuclease digestion notwithstanding a possible decrease in transcription or translation efficiency.

In one embodiment, the modulation results in an increase or elevation in the levels of expression of a genetic sequence. This occurs by removing RTG or RUG sites in the 5' leader region of the genetic sequence.

Reference in this case to a 5' leader sequence "of the genetic sequence" includes the leader sequence naturally associated with the genetic sequence or a 5' sequence ligated to the 5' end of a genetic sequence. The genetic sequence may be considered, therefore, as comprising a heterologous 5' leader sequence or homologous 5' leader sequence depending on whether the 5' leader sequence is naturally associated with a genetic sequence (i.e. homologous) or is introduced (i.e. heterologous).

Another aspect of the present invention contemplates, therefore, a method for facilitating increased or elevated expression of a genetic sequence wherein said sequence comprises an ORF having an RTG or RUG wherein R is A or G corresponding to an authentic translation initiation site of said ORF and a nucleotide sequence 5' of said authentic translation initiation site, said method comprising removing one or more RTG or RUG triplets in said 5' nucleotide sequence upstream of said authentic translation initiation site such that upon expression of said genetic sequence, there is an increase in the level of expression relative to expression of the genetic sequence in the absence of removal of any RTG or RUG triplet.

The term "authentic" is not to necessarily imply a naturally occurring start site although this is encompassed by the present invention. An authentic start site may be introduced but nevertheless is the translation start site for an ORF. Reference to "removing" one or more RTG or RUG triplets includes changing a single base to destroy a RTG/RUG triplet or deleting the triplet altogether or deleting a nucleotide sequence comprising or particularly containing the RTG/RUG triplet. Furthermore, an RTG/RUG triplet may be disrupted or removed by inserting a nucleotide sequence between an RT or RU or between TG or UG.

In one embodiment, the genetic sequence is DNA.

Accordingly, the present invention provides a method for facilitating increased or elevated expression of a genetic sequence wherein said sequence comprises an ORF having an RTG wherein R is A or G corresponding to an authentic translation initiation site of said ORF and a nucleotide sequence 5' of said authentic translation initiation site, said method comprising removing one or more RTG triplets in said 5' nucleotide sequence upstream of said authentic translation initiation site such that upon expression of said genetic sequence, there is an increase in the level of expression relative to expression of the genetic sequence in the absence of removal of any RTG triplet.

Removal of an RTG site is as defined above for the removal of an RTG or RUG. In both cases, the preferred R is A.

In another embodiment, the genetic sequence is RNA.

Accordingly, the present invention relates to a method for facilitating increased or elevated expression of a genetic sequence wherein said sequence comprises an ORF having an RUG wherein R is A or G corresponding to an authentic translation initiation site of said ORF and a nucleotide sequence 5' of said authentic translation initiation site, said method comprising removing one or more RUG triplets in said 5' nucleotide sequence upstream of said authentic translation initiation site such that upon expression of said genetic sequence, there is an increase in the level of expression relative to expression of the genetic sequence in the absence of removal of any RUG triplet.

In another preferred embodiment, the modulation results in a decrease or reduction in the levels of expression. This occurs by introducing or creating RUG or RTG triplets in the 5' leader sequence region.

Accordingly, the present invention contemplates a method for facilitating decreased or reduced expression of a genetic sequence wherein said sequence comprises an ORF having an RTG or RUG where R is A or G corresponding to an authentic translation initiation site of said ORF and a nucleotide sequence 5' of said authentic translation initiation site, said method comprising introducing or creating one or more RTG or RUG triplets in said 5' nucleotide sequence upstream of said authentic translation initiation site such that upon expression of said genetic sequence there is a decrease in the level of expression relative to expression of the genetic sequence in the absence of introducing or removing any RTG or RUG triplets.

Again, the genetic sequence may be DNA or RNA.

In the case of DNA, the present invention provides a method for facilitating decreased or reduced expression of a genetic sequence wherein said sequence comprises an ORF having an RTG where R is A or G corresponding to an authentic translation initiation site of said ORF and a nucleotide sequence 5' of said authentic translation initiation site, said method comprising introducing or creating one or more RTG triplets in said 5' nucleotide sequence upstream of said authentic translation initiation site such that upon expression of said genetic sequence there is a decrease in the level of expression relative to expression of the genetic sequence in the absence of introducing or removing any RTG triplets.

In the case that the genetic sequence is RNA, the present invention is directed to a method for facilitating decreased or reduced expression of a genetic sequence wherein said sequence comprises an ORF having an RUG where R is A or G corresponding to an authentic translation initiation site and a nucleotide sequence 5' of said authentic translation initiation site of said ORF, said method comprising introducing or creating one or more RUG triplets in said 5' nucleotide sequence upstream of said authentic translation initiation site such that upon expression of said genetic sequence there is a decrease in the level of expression relative to expression of the genetic sequence in the absence of introducing or removing any RUG triplets.

The introduction, creation or removal of an RUG or RTG triplet where R is A or G may be accomplished in any number of ways including site directed mutagenesis, homologous recombination or chemical or physical mutagenesis and may involve amplification reactions such a polymerase chain reactions with selected primers. For example, an RUG or RTG site may be created from an XUG or XTG triplet where X is neither A nor G by site directed mutagenesis to induce a substitution of X to an A or G. Similarly, mutagenesis may be used to convert RXG to RTG or RUG, RUX to RUG or RTX to RTG. Alternatively, short nucleotide sequences may be inserted or deleted to introduce or remove RTG or RUG triplets. Reference to removing an RTG or RUG triplet is not to be taken as necessarily deleting the three bases since nucleotide substitutions, deletions and/or additions may be induced to create or destroy a particular sequence.

Again, these embodiments include the manipulation of termination signals to create or destroy pseudo-ORFs within the leader sequence or beginning in the leader sequence and ending in the coding sequence or in the 3' region after the coding sequence. The present invention extends, therefore, to introducing or removing pseudo-ORFs within the 5' leader sequence and/or authentic ORF and/or the 3'UTR.

Site directed mutagenesis of a 5' leader sequence is one particularly useful method for the production of a variant having an RTG/RUG triplet created or removed. Site-directed mutagenesis of DNA is a method of altering a nucleotide sequence at one or more desired positions. Site-directed (i.e. site-specific) mutagenesis allows the production of sequence variants through the use of oligonucleotide sequences that encode a complementary DNA sequence comprising the desired mutation, as well as a sufficient number of adjacent nucleotides to provide a primer sequence of sufficient size and sequence complexity to form a stable duplex on both sides of the proposed mutation. Typically, a primer of about 20 to 25 nucleotides in length is preferred, with about 5 to 10 residues on both sides of the proposed mutation of the sequence being altered. In general, the techniques of site-specific mutagenesis are well known in the art. As will be appreciated, the site-specific mutagenesis technique typically employs a phage vector that exists in both a single-stranded and double-stranded form. Typical vectors useful in site-directed mutagenesis include vectors such as the M13 phage, for example, or other phage vectors which are commercially available. Their use is well known to those skilled in the art. Plasmid vectors which contain a single-stranded phage origin of replication may be employed to obtain single-stranded DNA. Alternatively, nucleotide substitutions are introduced by synthesizing the appropriate DNA fragment in vitro and amplifying it by PCR procedures known in the art.

A mutagenic PCR technique may also be used in creating 5' leader sequence variants. In a specific example of PCR mutagenesis, template plasmid DNA comprising a 5' leader sequence is linearized by digestion with a restriction endonuclease which has a unique recognition site in the plasmid DNA outside of the region to be amplified. Of this material, an aliquot is added to a PCR mixture containing PCR buffer, which contains the four deoxyribonucleotide triphosphates and is included in the GeneAmp (trade mark) kits (obtained from Perkin-Elmer Cetus, Norwalk, Conn. and Emeryville, Calif.), and each oligonucleotide primer. The PCR buffer contains divalent manganese ions which acts to increase the frequency at which the thermostable polymerase incorporates an incorrect nucleotide. This molecule then directs synthesis of a copy of itself in a subsequent round of PCR. As the reaction proceeds, a plurality of mutant sequences derived from the template 5' leader sequence accumulate in the reaction. The reaction mixture is then overlayered with mineral oil. The reaction is denatured for at, for example, 100° C., and placed briefly on ice and then Thermus aquaticus (Taq) DNA polymerase, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus). The Cycler may be programmed as appropriate to the conditions. One suitable programme is 2 min at 55° C., 30 sec at 72° C., then 19 cycles of the following: 30 sec at 94° C., 30 sec at 55° C. and 30 sec at 72° C. At the end of the program, the reaction tube is removed from the thermal cycler and the aqueous phase transferred to a new tube, extracted with phenol/chloroform (50:50 vol), and ethanol precipitated, and the DNA is recovered by standard procedures. This material is subsequently subjected to appropriate treatments for insertion into a vector. Individual clones arising from the PCR mutagenesis reaction can be sequenced to isolate individual nucleic acid molecules that contain the desired mutations.

Random mutagenesis of 5' leader nucleotide sequences may also be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

As stated above, expression of a genetic sequence is modulated by introducing or creating or removing particular pseudo-translation initiation sites. This may be visualized by using a schematic representation of an upstream, i.e. 5', nucleotide sequence. One such schematic representation is provided below.

The present invention contemplates, therefore, a method for modulating the expression of a genetic sequence wherein said sequence comprises an ORF having an RTG or RUG corresponding to an authentic translation initiation site and a nucleotide sequence 5' of said authentic translation start site comprising the sequence:

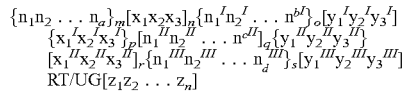

wherein:
RT/UG is the authentic translation initiation site and R is A or G;
n, $n^I$, $n^{II}$ and $n^{III}$ are nucleotides selected from A, T or U, C or G or I;
$\{n_1 n_2 \ldots n_a\}_m$, $\{n_1^I n_2^I \ldots n_b^I\}_o$, $\{n_1^{II} n_2^{II} \ldots n_c^{II}\}_q$ and $\{n_1^{III} n_2^{III} \ldots n_d^{III}\}_s$ represent nucleotide sequences of a, b, c or d nucleotides in length and where each of n, $n^I$, $n^{II}$ and $n^{III}$ may be the same or different and its position is indicated by the subscript numeral $_{1, 2, \ldots}$;
$[z_1 z_2 \ldots z_n]$ represents a translation termination signal within an authentic ORF but not in the same reading frame as said authentic ORF;
each of m, n, o, p, q, r, s or c may be the same or different and each is 0 or 1 or if there is a repeat or multiple repeats, from about 2 or about 10;
t is 0, 1 or >1;
each of $[x_1 x_2 x_3]_n$, $[x_1^I x_2^I x_3^I]_p$ and $[x_1^{II} x_2^{II} x_3^{II}]_r$ is selected from the triplet RTG, RUG, RYG, $RTY^I$, $RY^{II}G$, $RUY^{III}$, ATG, GTG, AUG and GUG where R is A or G, and each of Y, $Y^I$, $Y^{II}$ and $Y^{III}$ may be the same or different and each is a nucleotide with the proviso that Y is not T, $Y^I$ is not G, $Y^{II}$ is not U and $Y^{III}$ is not G;
each of $[y_1^I y_2^I y_3^I]$, $[y_1^{II} y_2^{II} y_3^{II}]$ and $[y_1^{III} y_2^{III} y_3^{III}]$ represents a translation termination signal; and
said method comprising altering the nucleotide triplets $[x_1 x_2 x_3]_n$, $[x_1^I x_2^I x_3^I]_p$ and/or $[x_1^{II} x_2^{II} x_3^{II}]_r$ to introduce or remove an RTG or RUG to thereby respectively decrease or increase the level of expression of said genetic sequence.

Preferred termination signals are selected from but are not limited to TGA, TAA, TAG, UGA, UAA and UAG.

When the genetic sequence is a DNA, the modulation involves introducing or removing an RTG.

When the genetic sequence is RNA, the modulation involves introducing or removing an RUG.

In this method, the $[x_1 x_2 x_3]_n$, $[x_1^I x_2^I x_3^I]_p$ and $[x_1^{II} x_2^{II} x_3^{II}]_r$ triplets are mutagenized by a nucleotide substitution, deletion and/or addition or is chemically or physically mutagenized to introduce or create or remove an RTG or RUG site where R is A or G. Preferably, R is A.

One skilled in the art will appreciate that the 5' nucleotide sequence may be longer or shorter than represented above and may include more potential pseudo-translation initiation sites than represented above. The 5' sequence as represented serves as a guide to the general structure. The essence of this aspect of the present invention is the manipulation of the 5' sequence to introduce, create or remove RTG or RUG triplets wherein R is A or G.

An RTG/RUG triplet in the 5' leader sequence is regarded as a pseudo-translation initiation site. The nucleotide sequence between an upstream RTG/RUG triplet and a termination signal is regarded as a pseudo-ORF (also referred to as an upstream ORF [uORF]).

The essence of this aspect of the present invention is the manipulation of the number of pseudo-translation initiation sites and optionally pseudo-ORFs. Although the effects on expression is difficult to quantify given the inherent variabilities of a biological system, semi-quantification is possible and provides useful input data for an algorithm or other data processing means.

Conveniently, the invention may be represented as a nucleotide sequence having the sequence:

$$n_x n_{x+i} \ldots n_{x+z}$$

wherein:
$n_x$ is the first nucleotide in a leader sequence;
x is 1 or >1 (e.g. 100, 1000, 10,000 or greater);
$i$ is 1;
$z$ is an integer from 1 to 10;
$n_{x+z}$ is the last nucleotide of the 5' leader sequence prior to the authentic translation initiation site;

wherein each n may be the same or different and each is A, C, G, U, T or I;

wherein a numerical value ($N_V$) is assigned to a genetic element such that if:
$n_{x+i}$=n, as defined above;
$n_{x+i+1}$=A;
$n_{x+i+2}$=T or U; and
$n_{x+i+3}$=G then the $N_V$ is 1;

when
$n_{x+i}$=n, as defined above;
$n_{x+i+1}$=G;
$n_{x+i+2}$=T or U; and
$n_{x+i+3}$=G then the $N_V$ is 0.3;

and when:
$n_{x+i}$=n as defined above;
$n_{x+i+1}$=C or G;
$n_{x+i+2}$=T or C or G; and
$n_{x+i+3}$=A, T or C then the $N_V$ is 0;

such that the level of expression ($E_L$) of a nucleotide sequence operably linked at its 5' end to $n_x n_{x+1} \ldots n_{x+z}$ is inversely functionally associated (*) to the sum of $N_V$ determined from the nucleotide sequence $n_x n_{x+1} \ldots n_{x+z}$ such that $$E_L * \frac{1}{\sum N_V}$$

In this case, the sum is calculated from nucleotide $_x$ to nucleotide $_{x+z}$. The present invention provides data processing means, therefore, to establish a pattern of likelihood of expression of a genetic sequence based on the RTG/RUG content of the 5' sequence upstream of an authentic translation initiation site.

In one particularly useful embodiment, the 5' leader sequence is derived from a GLI1 gene leader sequence. For example, SEQ ID NO:1 comprises the sequence of the 5' leader sequence from murine GLI1 and is termed Mα-UTR. This sequence comprises five ATG sites interspersed in a sequence of nucleotides prior to the authentic ATG site. Two splice variants, Mβ-UTR and Mγ-UTR (SEQ ID NOS:2 and 3, respectively) carry two and one ATG sites, respectively.

The level of expression directed by these three UTRs, as defined by the expression $$E_L * \frac{1}{\sum N_V},$$

Mα-UTR has an $\sum N_V$ of 5.6, Mβ-UTR is 2.3 and Mγ-UTR is 0.3. Hence, the $\Sigma_V$ is expected to be Mα-UTR>Mβ-UTR>Mγ-UTR. This correlates well with the experimental results obtained on the levels of translation products.

Similarly, human GLI1 comprises two 5'UTRs, namely Hβ-UTR (SEQ ID NO:4) and Hγ-UTR (SEQ ID NO:5) with $\sum N_V$ of 3.6 and 0, respectively. Again, the level of expression conferred by these two UTRs is defined by Hγ-UTR>Hβ-UTR and this correlates well with the experimental findings.

Consequently, deletion of part of the 5'UTR containing RTG/RUG sites results in elevated expression of the GLI1 coding region in both murine and human systems.

The γ sequence of Mγ-UTR and Hγ-UTR is particularly useful, not only for a lack of pseudo-translation inhibition sites and pseudo-ORFs but also due to inherent properties in facilitating higher level expression of authentic ORFs operably linked thereto. The present invention, in a particularly preferred embodiment, is directed to the use of Mγ-UTR or Hγ-UTR sequence to facilitate expression of an authentic nucleotide sequence attached thereto.

The present invention extends to maintaining the same length of 5' leader sequence but altering the numbers of RTGs or RUGs. Alternatively, the 5' leader sequences may be reduced in length or increased in length by deletion or insertion of particular nucleotides.

The present invention, therefore, provides nucleotide sequences comprising a predetermined number of RTG/RUG triplets for use in inserting into the 5' leader sequence of a genetic sequence or for inserting between a coding sequence and a promoter region.

Accordingly, another aspect of the present invention provides a nucleotide sequence for use in modulating the expression of a genetic sequence wherein said genetic sequence comprises a coding region comprising a translation initiation site and optionally a 5' leader sequence such that said nucleotide sequence comprising a predetermined number of RTG or RUG triplets such that upon operable linkage to the 5' end of the genetic sequence, the level of expression of said genetic sequence is determined by the number of RTG/RUG triplets.

In one form, the RTG/RUG sites in the 5' leader region are regarded as pseudo-translation initiation sites wherein the number of such triplets is inversely functionally associated to the level of expression, i.e. the higher the number of RTG/RUG triplets, the lower the level of expression.

In another form, the level of expression of a genetic sequence is determined by the number of elements defined by the sequence:

$$[nRWGn]_m$$

where:
n is any nucleotide or sequence of nucleotides and wherein the sequence is defined by $n_1 n_2 \ldots n_n n_{n+1}$ and n is from about 1 to about 1000, preferably from about 2 to about 500, more preferably from about 3 to about 100 and even more preferably from about 4 to about 50;
R is G or A;
W is T or U; and
m is from 0 to about 100, or from 0 to about 50 or from 0 to about 20 or from 0 to about 10 and represents the polydispersion of the nRWGn sequence throughout the 5' leader sequence.

In a similar embodiment, a decrease in the level of expression may occur when a 5' leader sequence which comprises the sequence:

$$[nX_1X_2X_3n]_m$$

wherein:
n and m are as defined above and the triplet $X_1X_2X_3$ is selected from $Rn_1^I G$, $n_2^I TG$, $n_3^I UG$, $RTn_4^I$, $RUn_5^I$ where R is A or G and $n^I$ is any nucleotide with the proviso that $n_1^I$ is not T or U, $n_2^I$ or $n_3^I$ is not A and $n_4^I$ and $n_5^I$ is not G; and
wherein said sequence is mutated to cause a substitution or other mutation in n to change same to provide the triplet RTG or RUG where R is as defined above.

The present invention further provides a plurality of nucleotide sequences each comprising a predetermined number of RTG or RUG triplets wherein R is A or G wherein said predetermined number is from 0 to about 100 and preferably from about 0 to about 50 and even more preferably from about 0 to about 15 such that to facilitate expression of a genetic sequence to a particular level, a particular nucleotide sequence is selected and inserted or placed between a promoter and said genetic sequence such that the promoter is operably linked to said genetic sequence and wherein the level of expression is inversely functionally associated with the number of RTG or RUG triplets upstream of the authentic translation initiation site.

Such nucleotide sequences include one or more oligonucleotide sequences such as an oligonucleotide sequence with a predetermined number of pseudo-translation initiation sites and optionally pseudo-ORFs.

In a specific embodiment, the plurality of nucleotide sequences is selected from a 5' leader sequence from the GLI1 gene.

Accordingly, another aspect of the present invention is directed to an isolated nucleic acid molecule comprising a nucleotide sequence encoding a 5' mRNA sequence, said mRNA sequence selected from SEQ ID NO:1 to SEQ ID NO:5 or a nucleotide sequence having at least 60% similarity to one or more of SEQ ID NO:1 to SEQ ID NO:5 or a nucleotide sequence capable of hybridizing to one or more of SEQ ID NO:1 to SEQ ID NO:5 or a complementary form thereof under low stringency conditions wherein said nucleotide sequence is capable of influencing the level of expression of a genetic sequence operably linked to said nucleotide sequence.

As stated above, SEQ ID NOS:1 to 3 correspond to Mα-UTR, Mβ-UTR and Mγ-UTR, respectively. SEQ ID NOS:4 and 5 correspond to Hβ-UTR and Hγ-UTR, respectively. Partial genomic sequences corresponding to M-UTR are shown in SEQ ID NOS:33 and 34. Partial genomic sequences corresponding to H-UTR are shown in SEQ ID NOS:35 and 36. Complete genomic sequences for M-UTR and H-UTR are shown in SEQ ID NOS: 59 and 60, respectively.

Accordingly, the present invention provides an isolated nucleic acid molecule comprising a nucleotide sequence encoding a non-translated mRNA sequence, said nucleotide sequence selected from SEQ ID NO:33 to SEQ ID NO:36 or a nucleotide sequence having at least 60% similarity to one or more of SEQ ID NO:33 to SEQ ID NO:36 or a nucleotide sequence capable of hybridizing to one or more of SEQ ID NO:33 to SEQ ID NO:36 or complementary forms thereof under low stringency conditions wherein said nucleotide sequence is capable of influencing the level of expression of a genetic sequence operably linked to said nucleotide sequence.

Another aspect of the present invention provides an isolated nucleic acid molecule comprising a nucleotide sequence encoding a non-translated mRNA sequence, said nucleotide sequence selected from SEQ ID NO:59 or 60 or a nucleotide sequence having at least 60% similarity to one or more of SEQ ID NO:59 or 60 or a nucleotide sequence capable of hybridizing to one or more of SEQ ID NO:59 or 60 or complementary forms thereof under low stringency conditions wherein said nucleotide sequence is capable of influencing the level of expression of a genetic sequence operably linked to said nucleotide sequence.

The term "influencing" includes increasing or decreasing (i.e. modulating) the level of expression depending on which 5'UTR is employed. The Mγ-UTR and Hγ-UTR are particularly useful in facilitating expression of genetic sequences as attached thereto.

The term "similarity" as used herein includes exact identity between compared sequences at the nucleotide level. Where there is non-identity at the nucleotide level, "similarity" includes differences between sequences which result in different amino acids that are nevertheless related to each other at the structural, functional, biochemical and/or conformational levels. In a particularly preferred embodiment, nucleotide sequence comparisons are made at the level of identity rather than similarity.

Terms used to describe sequence relationships between two or more polynucleotides include "reference sequence", "comparison window", "sequence similarity", "sequence identity", "percentage of sequence similarity", "percentage of sequence identity", "substantially similar" and "substantial identity". A "reference sequence" is at least 5 but frequently 12 to 18 and often at least 25 or above, such as 30 monomer units, inclusive, of nucleotides. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 5 nucleotides that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (36). A detailed discussion of sequence analysis can be found in Unit 19.3 of Ausubel et al. (37).

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, is calculated by comparing two optimally aligned sequences over the window of comparison, determining the number of positions at which the identical nucleic acid base (e.g. A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25–30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (38). However, the $T_m$ of a duplex DNA decreases by 1° C. with every increase of 1% in the number of mismatch base pairs (39). Formamide is optional in these hybridization conditions. Accordingly, particularly preferred levels of stringency are defined as follows: low stringency is 6×SSC buffer, 0.1% w/v SDS at 25–42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The present invention further provides a genetic construct comprising a genetic element having a predetermined number of pseudo-translation initiation sites, i.e. RTG/RUG triplets. Generally, the genetic element is in a vector construct operably linked at its 5' end to a promoter and comprising one or more unique or semi-unique restriction endonuclease sites within a nucleotide which is part of or linked to the genetic element. These sites are used to insert a nucleotide sequence to be expressed.

The present invention extends to a plurality of genetic constructs each with a genetic element within a predetermined number of pseudo-translation sites or a plurality of genetic elements for use in insertion into a genetic construct.

Accordingly, another aspect of the present invention contemplates a genetic construct comprising a promoter linked to a genetic element and one or more restriction endonuclease sites to facilitate insertion of a nucleotide sequence to be expressed by said promoter wherein said genetic element comprises a predetermined number of pseudo-translation initiation RTG/RUG triplets wherein R is A or G such that the level of expression of said nucleotide sequence by said promoter is inversely functionally associated with the number of RTG/RUG triplets in said genetic element.

The genetic construct may be a plasmid, vector, viral construct, linear or covalently closed circular molecule.

The nucleotide sequence to be expressed is also referred to as a coding sequence or ORF.

As used herein, a "construct" is a nucleic acid molecule into which a desired nucleotide sequence may be inserted by restriction and ligation. Such construct is useful for transport between different genetic environments or for expression in a host cell. Constructs are typically composed of DNA although RNA constructs are also available. The constructs of the present invention are generally for eukaryotic cells such as animal, mammalian and plant cells. Constructs include, but are not limited to, plasmids, vectors and phagemids. A cloning construct is one which is able to replicate in a host cell, and which is further characterized by one or more endonuclease restriction sites at which the construct may be cleaned in a determinable fashion and into which a desired nucleotide sequence may be ligated generally so that the new recombinant construct retains its ability to replicate in a host cell. In the case of plasmids, replication of the desired sequence may occur many times as the plasmid increases in copy number within a host bacterium or just a single time per host before the host reproduces by mitosis. In the case of phage, replication may occur actively during a lytic phase or passively during a lysogenic phase. An expression vector or construct is one into which a desired nucleotide sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase or alkaline phosphatase) and genes which visibly affect the phenotype of transformed or transfected cells, colonies or plaques. Preferred vectors are those capable of autonomous replication and expression of the structural gene products present in the DNA segments to which they are operably joined.

As used herein, a coding sequence and regulatory sequences are said to be "operably" joined or linked when they are covalently linked in such a way as to place the expression or transcription of the coding sequence under the influence or control of the regulatory sequences. If it is desired that the coding sequences be translated into a functional protein, two nucleotide sequences are said to be operably joined if induction of a promoter in the 5' regulatory sequences results in the transcription of the coding sequence and if the nature of the linkage between the two nucleotide sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired polypeptide or protein.

The precise nature of the regulatory sequences needed for gene expression may vary between species or cell types, but shall in general include, as necessary, 5', i.e. 5' non-coding and 5'UTR non-transcribing and 5' non-translating sequences involved with the initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene that comprises a 5' untranslated leader sequence. Regulatory sequences may also include enhancer sequences or upstream activator sequences as desired.

The constructs of the present invention are directed to providing a means of tailoring the expression of a nucleic acid molecule. Accordingly, the present invention contemplates a construct which contains one or more suitable restriction sites for insertion of a particular 5' leader or signal sequence or 5' UTR which contains none or one or more pseudo-translation initiation sites each of which may or may not be proximal to a Kozac sequence or a Kozac-like sequence. The choice and design of an appropriate construct is within the ability and discretion of one of ordinary skill in the art. Vector construction is well-known to those skilled in the art. For instance, the DNA manifestation of an RNA virus, such as HIV, is cleaved using restriction enzymes to excise HIV encoding sequences from within the gag coding region, following the nef gene. A cloning cassette comprised of a polylinker containing multiple restriction sites is inserted into the region of the deletion prior to ligation to provide convenient restriction sites for cloning into the vector. A DNA fragment containing the 5' leader sequence containing the number of pseudo-translation initiation sites is then sub-cloned into one of these sites. Subsequently, an ORF may be inserted down stream of the polylinker. It is envisaged that suitable restriction enzyme sites for the cloning of an ORF and simultaneous construction of a translation initiation RTG would be NcoI or NdeI. However, other restriction enzymes sites are also contemplated. The resultant vector will transcribe an mRNA with a 5' untranslated leader sequence capable of regulating the expression of the open reading frame to which the 5' leader sequence is operably linked. The level of expression will be is inversely functionally associated with the number of pseudo-translation initiation sites present in the 5' untranslated leader sequence.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney Virus, ALV, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine and human metallothionein.

Promoter elements contemplated herein include but are not limited to MM_INA2, MM_INA4, MM_INA5, MM_INA6, MM_INA7, HS_INA1, HS_INA6, HS_INA5, HS_INAD, HS_INAF, HS_INA4, HS_INAG, HS_INA7, HS_INB, MM_INB, HS_INA5, HCMV_IEI, MCMV_VIEI, HCMV_UL37, HCMV_US3, HSV1_ICPO, HSV1_IE63, HSV2_IE63, HSV1_ICP4, HSV2_IE3, HSV1_E68, HSV2_IE45, HCMV_POLB, HCMV_B22, HCMV_B27, HSV1_EXON, HSV1_UL49, HSV1_DUT, HSV1_B33, HSV1_B21, HSV1_RIR1, HSV1_RIR2, HSV2_RIR2, HSV1_KITH, HSV2_KITH, HSV1_DNBI, HSV1_VGLB, HSV1_VGLD, HSV2_VGLI, HSV1_VGLE HSV1_PRTP, HSV1_VGLG, HSV1_TEGP, HSV1_VCAP, HSV1_UL11, HSV1_ATIN, HSV1_ATI2, HCMV_UL36, HCMV_GP65, HCMV_GP71 and HCMV_G150, HSV1_G5, HSV_VGLC, HSV2_VGLC, HSV1_VGLH, HSV1_G42, HSV1_ORIS, HSV1_UL45, HSV2_UL45, EBV_BAM, EBV_VP14, EBV_BCRF, EBV_BHL1, EBV_UL34, EBV_VP26, EBV_BFL2, EBV_UL73, EBV_YLR2, EBV_VGP3, EBV_YLR3, EBV_DUT, EBV_VGLL, EBV_13KB, EBV_HL1, EBV_CL1, EBV_DR1, EBV_DL2, EBV_DL1A, HSV_TYSY, EBV_EBNA_1, EBV_EBNA_2, EBV_DL1, HS_PGK1, HS_CCEM, HS_CGM6, HIV1_LTR, HIV2_LTR, SRV1_LTR, SIV_LTR, SV40_TA_1, JCV_TL, POLY_COAT_1, SV40_TA_2, BKV_TA, POLY_TA_2, SV40_COAL, POLY_COAL, HBV_CORA_, GSHV_35KB_1, HBV_CORA_2, GSHV_35KB_2, DHBV_33KB, HBV_22_1, GSHV_23_1, HBV_22_2, GSHV_23_2, DHBV_18KB, BPV1_PL_1, BPV1_PL_2, BPV1_P79_1, HP18_VE6_1, BPV1_P89_2, HP16_VE, HP18_VE6_2, BPV1_P24, BPV1_P30, AD2_E1A, AD5_E1A, AD7_E1A, AD12_E1A_1, AD12_E1A_2, SA7P_E1A, AD2_E1B, AD5_E1B, AD7_E1B, AD12_E1B, AD2_V33P AD2_E3, AD5_E312, AD2_E411, AD2_PIV2, AD5_PIV2, AD7_4A2, AD2_9, AD5_9, AD7_HEX9, AD2_DNBI, AD5_DPOL, AD7_Y1, AD12_ML, AD2_L2A, MMLV_LTR, FMCF_LTR, MLVA_AKV, MLV_XENO, MMSV_LTR, GALV_LTR, SSV_LTR, GAFE_LTR, MMTV_PR73, BLV_LTR, HTV1_LTR, HTL2_LTR, RSV_LTR, ALV_LTR, RAV2_LTR, GG_EV1, SNV_LTR, AAV2_VNCA, AAV2_19, AAV2_COA3, H1_VNCS, H1_COAT and B19_06.

Examples of polyadenylation signals useful to practice the present invention, especially in the production of a genetic vaccine for humans, include but are not limited to, SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to human actin, human myosin, human hemoglobulin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen, (San Diego, Calif.) contain the Epstein Barr virus origin of replication and nuclear antigen EBNA-1 coding region which produces high copy episomal replication without integration.

The genetic construct may be administered with or without the use of microprojectiles. It is preferred that the genetic constructs of the present invention may be delivered to the cells of an individual free of solid particles. As used herein, the phrase "free of solid particles" is meant to refer to a liquid that does not contain any solid microprojectiles used as a means to perforate, puncture or otherwise pierce the cell membrane of a cell in order to create a port of entry for genetic material into the cell.

The genetic constructs of the present invention may be used to administer an individual where it may be necessary to modulate the expression of, for example, of a particular antigen. This may be useful in inducing immunization conditions. In particular, modulated expression may be appropriate when delivering genetic sequences capable of expressing antigens derived from pathogens such as viruses, prokaryotes and pathogenic eukaryotic organisms such as unicellular pathogenic organisms and multi-cellular parasites. The present invention is particularly useful to regulate the immune response when over-expression of antigens may lead to an inappropriate immune response such as in an inappropriate histamine release or anaphylactic shock. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least of its reproductive or life cycle, exists within a host cell and therein produces or causes to be produced, pathogen proteins.

The present invention also contemplates the use of a 5' leader sequence to regulate the expression of genetic sequences which encode therapeutic agents including peptides, polypeptides or proteins including, as stated above, genetic material which encodes peptides, polypeptides or protein that are antigens for immunization. Nucleic acid molecules of the present invention are introduced into the cells of an animal. In this aspect, the present invention may require that the high level of uptake and function of the nucleic acid molecules. The method of the present invention further comprises the steps of administering nucleic acid molecules, preferably free of viral particles, particularly retroviral particles, to the cell of an individual. Administration may also be in conjunction with a genetic vaccine facilitator agent. The genetic vaccine facilitator agent is selected from the group consisting of anionic lipids, extracellular matrix-active enzymes, saponins, lectins, estrogenic compounds and steroidal hormones, hydroxylated lower alkyls, dimethyl sulfoxide (DMSO) and urea. The genetic vaccine facilitator agent preferably enhances the inflammatory response and/or enhances expression of the nucleic acid molecule in the tissue and/or facilitates the uptake of the nucleic acid molecule by the cell.

When taken up by a cell, the genetic construct which includes the nucleotide sequence encoding the desired protein operably linked to the regulatory elements herein described may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful in promoting integration may also be included in the DNA molecule. Alternatively, RNA may be administered to the cell. It is also contemplated to provide the genetic construct as a linear minichromosome including a centromere, telomeres and an origin of replication.

The present invention is particularly useful for the generation of genetically modified plants. Plants may be monocotyledonous or dicotyledonous.

Suitable methods for introduction of genetic material into cells include transformation using $CaCl_2$ and variations thereof, direct DNA uptake into protoplasts, PEG-mediated uptake to protoplasts, microparticle bombardment, electroporation, microinjection of DNA, microparticle bombardment of tissue explants or cells, vacuum-infiltration of tissue with nucleic acid and T-DNA-mediated transfer from *Agrobacterium* to the plant tissue.

*Agrobacterium*-mediated transformation of suitable plants may be effected by co-cultivating an explant to be transfected with *Agrobacterium* species having a T-DNA or T-DNA region comprising the genetic material to be transformed into the plant cells, for a time and under conditions sufficient for the genetic material to transfer into the plant cells. The *Agrobacterium* species may be either high or low virulent strain. A particularly useful *Agrobacterium* species is *Agrobacterium tumefaciens* strain AGL0 (45), AGL1 (45), strain ICMP 8317 (46), strain EHA101 (47), strain LBA4404 (48) and strain C58 (49).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 0.1 to 10 µm and more particularly 10.5 to 5 µm tungsten or gold spheres. The genetic construct may be deposited on the microparticle by any suitable technique, such as by precipitation.

The genetic transformation and regeneration methods of the present invention may be employed to confer on a plant cell specifically-desired traits such as, for example, resistance to attack by disease-causing pathogenic agents, modified fatty-acid content, improved quality and the capability to synthesize novel, high value and value-added products and to induce different levels of resistance to herbicides and pesticides.

Expression of genetic sequences in plants may also be required to be tissue or developmentally specific. Suitable promoters or other regulatory sequences may be selected to ensure tissue or developmental specificity.

In accordance with one particularly preferred embodiment of the present invention, a genetic construct comprising a desired trait may be incorporated into a plasmid capable of replicating in a plant cell, coated onto gold or tungsten microparticles by, for example, precipitation and bombarded into embryogenic callus to produce transformed callus cells, capable of being regenerated into transgenic plantlets. The transformed embryogenic callus cells of the present invention are selected under any one of a number of suitable selective agents well known to those skilled in the art. Alternatively, the gold or tungsten microparticles may be bombarded into immature embryos from which selected transformed embryogenic callus, capable of being regenerated into transgenic plantlets, is induced to form.

To facilitate identification of transformed cells, the embryogenic callus is bombarded with a further genetic construct, comprising a selectable or screenable marker gene. The actual choice of a marker is not crucial as long as it is functional (i.e. selective) in combination with the plant cells of choice. The marker gene and the gene of interest do not have to be linked, since co-transformation of unlinked genes as, for example, described in U.S. Pat. No. 4,399,216 is also an efficient process in plant transformation.

Included within the terms "selectable or screenable marker genes" are genes that encode a "secretable marker" whose secretion can be detected as a means of identifying or selecting for transformed cells. Examples include markers that encode a secretable antigen that can be identified by antibody interaction or secretable enzymes that can be detected by their catalytic activity. Secretable proteins include, but are not restricted to, proteins that are inserted or trapped in the cell wall (e.g. proteins that include a leader sequence such as that found in the expression unit of extensin or tobacco PR-S); small, diffusible proteins detectable, for example, by ELISA; and small active enzymes detectable in extracellular solution such as, for example, α-amylase, β-lactamase, phosphinothricin acetyltransferase).

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (neo) gene conferring resistance to kanamycin, paromomycin, G418 and the like as, for example, described by Potrykus et al. (50); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al. (51), a bar gene conferring resistance against bialaphos as, for example, described in WO91/02071; a nitrilase gene such as bxn from *Klebsiella ozaenae* which confers resistance to bromoxynil (52); a dihydrofolate reductase (DHFR) gene conferring resistance to methotrexate (53); a mutant acetolactate synthase gene (ALS), which confers resistance to imidazolinone, sulfonylurea or other ALS-inhibiting chemicals (EP-A-0 154 204); or a mutated anthranilate synthase gene that confers resistance to 5-methyl tryptophan.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (54), which may be employed in calcium-sensitive bioluminescence detection; a green fluorescent protein gene (55); a luciferase (luc) gene (56), which allows for bioluminescence detection; a β-lactamase gene (57), which encodes an enzyme for which various chromogenic substrates are known (e.g. PADAC, a chromogenic cephalosporin); an R-locus gene, encoding a product that regulates the production of anthocyanin pigments (red colour) in plant tissues (58); an α-amylase gene (59); a tyrosinase gene (60) which encodes an enzyme capable of oxidizing tyrosine to dopa and dopaquinone which in turn condenses to form the easily detectable compound melanin; or a xylE gene (61), which encodes a catechol dioxygenase that can convert chromogenic catechols.

As will also be appreciated by a person skilled in the relevant art, media components suitable for effecting the formation of transformed polyembryogenic callus from transformed embryogenic callus are many and varied. Such components may include but are not limited to sugars, amino acid and vitamin supplements, and growth promoting hormones such as auxins and cytokines. Sometimes, an improvement in the speed or efficacy of the desired outcome may be achieved by manipulation of these components and the concentrations at which they are present. In accordance with the present invention, preferred components have been found to include an auxin, such as naphthalene acetic acid, indole acetic acid or indole butyric acid.

In one embodiment, the auxin is indole butyric acid. In a particular embodiment, indole butyric acid is present in the medium at a concentration in the range 1–10 μM, preferably 3–8 μM and even more preferably 4–6 μM. Those skilled in the art will appreciate that the concentration may be varied somewhat and still be effective for the desired purpose.

The method of the present invention is initiated by obtaining an explant from a plant, generally in the form of leaf or root tissue or an immature embryo. After sterilization, the explant is transferred to callus induction medium, comprising for example, MS salts and $Y_3$ vitamins, supplemented appropriately, and incubated at 28° C. in the dark. For leaf and root explants, supplements include myo-Inositol, L-glutamine, sucrose, activated charcoal, agar and an auxin, such as for example, 4-dichlorophenoxy-acetic acid (2,4-D). For immature embryo explants, supplements include myo-Inositol, L-glutamine, sucrose, NaFeEDTA and, preferably, thiamine or coconut water. Coconut water, at a concentration of 50–150 ml/l and more preferably 100 ml/l, is a particularly-preferred supplement.

For leaf and root explants, incubation continues for a period of about 6–8 weeks or until the beginning of production of embryogenic calli, following which the cultures are sub-cultured every 12 weeks. In the case of immature embryo explants, incubation continues with sub-culturing every 3–4 weeks, for up to 12 weeks or until embryogenic calli were produced.

Embryogenic calli are maintained on embryogenic medium, comprising, for example, MS salts, macro- and micro-nutrients and $Y_3$ vitamins supplemented with myo-Inositol, L-glutamine, L-asparagine, sucrose and auxins, such as for example, 10 μM 2,4-D and 5 μM naphthalene acetic acid (NAA), and are incubated at 28° C. in the dark. Embryogenic calli are sub-cultured every 30 days into fresh nutrient medium. During maintenance of said embryogenic callus cultures, distinct morphological Types (I, II and III) of embryogenic callus are obtained.

Type I, Type II or Type III embryogenic callus, and preferably Type II embryogenic callus, is subjected to transformation via microparticle bombardment of gold particles, having diameter of preferably 0.1–3.0 microns, more preferably 0.5–2.0 microns and still more preferably 0.8–1.2 microns, onto which has been precipitated a desired-DNA-containing genetic construct. Gold particles are bombarded into preferably 0.1–2.0 grams wet weight of embryogenic callus, more preferably 0.3–1.0 gram wet weight of embryogenic callus, and still more preferably 0.5–0.7 gram wet weight of embryogenic callus.

The putatively-transformed embryogenic callus cultures are then subjected to selection under an appropriate selection environment. For example, selection of transformed cells may be achieved using a variety of chemical agents, such as antibiotics (e.g. hygromycin and/or geneticin (G418)) or herbicides (e.g. BASTA (trademark)). Use of these agents may require the inclusion of a selectable marker gene, such as but not limited to the hph gene for hygromycin resistance or the nptII gene for geneticin or kanamycin resistance, and the bar gene for BASTA (trademark) resistance. These genes render the transformed cells resistant to the selection agent.

One particularly useful selection medium comprises BASTA (13.5% PPT) at concentrations of about 35–45 ppm, and preferably 40 ppm, to about 75–85 ppm and preferably 80 ppm, or at gradually increasing concentrations of from about 5–15 ppm, and preferably 10 ppm, to about 15–25 ppm, and preferably 20 ppm, and finally to about 35–45 ppm, and preferably 40 ppm at 3 weeks post-bombardment.

Following selection, transformed embryogenic callus cultures are generally transferred to polyembryogenic-inducing medium, comprising for example, MS salts, macro- and micro-nutrients and $Y_3$ vitamins supplemented with myo-Inositol, L-glutamine, L-asparagine, L-arginine, sucrose and agar, and an auxin, such as for example, 5 μM indole butyric acid (IBA), in which they are cultured for generally at least about 3–6 months, more usually at least about 3–4 months and preferably at least 4 months, with sub-culturing into fresh medium generally every 20–40 days, more particularly every 25–35 days and preferably about every 30 days, until the formation of green-coloured polyembryogenic cultures.

Transformed polyembryogenic cultures are finally transferred to cells an appropriate shoot-inducing medium, such as, for example, MS salts, macro- and micro-nutrients and $Y_3$ vitamins, supplemented with myo-inositol, L-glutamine, L-asparagine, L-arginine, sucrose and agar, and an auxin such as for example 0.1 μM NAA. Normally, shoot induction requires at least about 2–4 months, and more usually at least about 3 months. Propagation of shoots generally requires an auxin, such as NAA. Production of roots generally requires a further auxin, such as for example 2, 4-D, in addition to NAA. Other possibly suitable auxins include indole acetic acid (IAA) and IBA. Accordingly, roots are induced in medium supplemented as above, but with the addition of 10 μM 2,4-D, 70 μM NAA, and activated charcoal. After incubation at 28° C. for at least about 2 months, the plantlets are then transferred to soil.

The present invention provides, therefore, a genetically modified plant cell or genetically-modified and regenerated multicellular plant or progeny thereof or parts of said transgenic plant exhibiting altered levels of expression of a target gene.

The method of the present invention is also particularly useful for up-regulating or down-regulating the function of a promoter. In some circumstances, a promoter may be too active. The introduction of pseudo-translation initiation sites or pseudo-ORFs between the promoter and the authentic translation initiation site is a useful mechanism for reducing expression.

The effects of introducing or creating pseudo-translation initiation sites and in particular RTG/RUG triplets may be enhanced or otherwise modulated by creating or removing or modifying Kozac or Kozac-like sequences. A Kozac-like sequence includes a modified Kozac sequence. A modified Kozac sequence includes a weak or strong Kozac sequence. A Kozac sequence comprises the nucleotides:

```
RnCCRWGn                                    [SEQ ID NO:6]
``` wherein:
  R is A or G;
  n is any nucleotide; and
  W is U or T.
An example of a strong Kozac sequence is:

```
GCCRCCRWGG [SEQ ID NO:7]
``` whereas an example of a weak Kozac sequence is represented as:

```
ATTTCCRWGn [SEQ ID NO:8].
```

Accordingly, an existing RWG site where R is A or G and W is T or U may be made more efficient is a pseudo-translation initiation site by manipulating Kozac or Kozac-like sequences proximal to said pseudo-translation initiation triplet to either create or destroy a Kozac or Kozac-like sequence or to change from a weak to strong or strong to weak Kozac sequence.

For example, 5' leader sequence may include the nucleotides:

```
ATTTCCTTGA [SEQ ID NO:9].
```

A first manipulation is to create an ATG site resulting in the sequence:

```
ATTTCCATGA [SEQ ID NO:10].
```

The ATG site is located within a weak Kozac sequence. This sequence may be manipulated to render it a strong Kozac sequence such as by substituting "ATTT" with "GCCA/G", to create the sequence:

```
GCCA/GCCATGA [SEQ ID NO:11].
```

The first A after the ATG may also be changed to a G.

The effect of such a modification is to enhance the pseudo-translation initiation activity of the introduction ATG triplet thereby increasing the down-regulating effects of the introduction of the pseudo-translation inhibiting triplet.

Accordingly, another aspect of the present invention contemplates a method for modulating expression of a genetic sequence, wherein said genetic sequence comprises an ORF with an authentic translation initiation site and further comprising a sequence upstream of said authentication translation initiation site where said method comprises introducing, creating or removing one or more pseudo-translation initiation triplets having the structure RWG wherein R is A or G and W is T or U in combination with introducing, creating or removing a Kozac or Kozac-like sequence proximal to said RWG such that the number of RWG triplets and Kozac or Kozac-like sequences is inversely functionally associated with expression of said genetic sequence.

Preferably, in one embodiment, the manipulation results in a sequence comprising:

```
RnCCRWGn
``` wherein:
  R is A or G;
  n is any nucleotide; and
  W is T or U.

The present invention is further described by the following non-limiting Examples.

EXAMPLE 1

Reverse Transcriptase-PCR (RT-PCR), 5' RACE and PCR

Skin, brain, heart, kidney, liver, lung, muscle, stomach, spleen, testis and tongue were obtained from various strains of neonatal, juvenile and adult mice. Total RNA was isolated from these tissues using TRI Reagent (Molecular Research Center). First-strand cDNA was synthesized from 5 µg of total RNA primed with oligo(dT)$_{16}$ (Perkin Elmer) or random hexamers (Clontech) using superscript (trade mark) II Reverse Transcriptase (Life Technologies) in a total volume of 20 µl. One-tenth by volume of the cDNA was used as the template for subsequent PCR reactions. Primer pairs (listed in Table 1) for mouse GLI1 corresponding to sequences within exon 1 (mGliF1) and exon 2 (mGliR2) and for human GLI1 corresponding to exon 1 (hGliF1) and exon 2 (hGliR2) sequences were used. Each PCR reaction was repeated at least three times with different RNA preparations and included negative controls for each set of reactions. For 5' RACE, the inventors used a cDNA template that was generated using the primer RACE1 and C-tailed using terminal transferase according to the manufacturer's protocol (Life Technologies). PCR was performed using the RACE anchor and adapter primers (Life Technologies) and the GLI1-specific nested primer RACE2. Mouse genomic DNA was amplified using primers derived from exon 1a (mGliF1a) and exon 2 (mGliR2) sequences. All PCR products were separated on 0.8–2% w/v agarose gels and visualized with ethidium bromide. Separated fragments were purified using QIAEX (registered trade mark) II (QIAGEN) and sequenced directly using the Big Dye-termination Kit and automated fluorescent sequencing on an ABI-Prism 377 DNA Sequencer (Perkin Elmer).

EXAMPLE 2

TPA Treatment of Mouse Skin

Neonatal and 7 day old mice (Swiss outbred) were treated with 20–50 µl of 100 µg/ml 12-O-tetradecanoylphorbol 13-acetate (TPA) (Sigma) topically applied to back skin. Mice were sacrificed at different time points (0 hr, 3 hr, 8 hr and 24 hr) post-application and total skin RNA prepared for RT-PCR as described above.

EXAMPLE 3

5'-UTR-GFP Constructs and Functional Analysis of 5'UTRs

Each of the three alternative 5'UTRs of mouse GLI1 were generated by RT-PCR using primers mGliF1$^{Nhe}$ and mGliQR2$^{Age}$ (Table 2) that contain NheI and AgeI restriction sites, respectively. PCR products were gel-purified and cloned into the pGEM-T Easy Vector (Promega). The four ATG codons of the αUTR were mutated sequentially using the QuikChange (trade mark) Site-Directed Mutagenesis kit (Stratagene) and complementary primers mGliMf1–4 [SEQ ID NOS:19–22] and mGli1Mr1–4 [SEQ ID NOS:23–26] (Table 2). The γUTR sequence was multimerized using primers mGliF1$^{Bam}$ [SEQ ID NO:27] and mGLiR$^{Bgl}$ [SEQ ID NO:28] that contain BamHi and BglII sites. The amplified fragment was cloned into pGEM-T Easy, sequence and the insert released by digestion with BamHI and BglII. The purified fragment was ligated in the presence of both restriction enzymes to form similarly oriented concatomers that were then used as templates for PCR amplification using mGLiF1$^{Nhe}$ [SEQ ID NO:29] and mGliR2$^{Age}$ [SEQ ID NO:30]. The products of this reaction were sized on an agarose gel and the band corresponding to four copies of the γUTR cloned into the pGEM-T Easy Vector. All inserts were verified by sequence analysis, released from the pGEM-T Easy Vector by restriction digestion with NheI and AgeI and subcloned into the corresponding sites of the Green Fluorescence Protein (GFP) expression vector, pEGFP-N1 (Clontech).

HaCaT, a human heratinocyte cell line (33), Cos-1 (40) and BHK-21 (41) cells were cultured in Dulbecco's modified Eagle's medium (DMEM) supplemented with 10% v/v fetal calf serum, ampicillin and streptomycin (Life Technologies). Primary mouse skin fibroblasts were obtained from newborn Swiss mice using an established protocol. Briefly, skin was removed, washed in PBS and incubated in 2.5% w/v dispase (Life Technologies) for 24 hr at 4° C. The dermis was separated from the epidermis and incubated in 0.2% w/v collagenase (Sigma) at 37° C. for one hr. Cells were then pelleted and washed in PBS and cultured in DMEM media as described above. Primary fibroblasts were used within the first two weeks of culturing.

Transient transfection of GFP constructs was performed using LipofectAMINE PLUS Reagent (Life Technologies) according to the manufacturer's instruction. Cells were seeded on round, glass coverslips in 24-well (fluorescence microscope study) or 6-well plates (flow cytometry study) 24 hr prior to transfection and incubated at 37° C. to a density of about 50–70% confluence. Cultures were washed twice in serum-free media and then incubated in DNA-PLUS-LipofectAMINE complexes in OPTI-MEM (Life Technologies) for three hr at 37° C. DMEM media containing serum was then added to the culture. One day later, cells were fixed for microscopy or harvested flow cytometry analysis. Twenty thousand cells per sample were analyzed on a FACSCalibur (Becton Dickinson) cell sorter, using CELLQuest software (Becton Dickinson).

EXAMPLE 4

Identification of Alternative Mouse GLI1 5'UTRs

In order to identify the transcriptional start site of the mouse GLI1 gene, 5'RACE was performed on total skin RNA from a BALB/c mouse and the resulting PCR product directly sequenced. This analysis showed that sequences around the translation start codon and at the beginning of the transcript were identical to the published mouse GLI1 sequence obtained from F9 cells (42). However, the RACE product also contained an additional 119 bp, not present in the published sequence, located at the splice junction between exon II and exon III as numbered by Liu et al. (42). The inventors named this new 5'UTR variant,α-UTR and the published sequence as β-UTR (FIG. 1A). To search for other possible splicing variants, RT-PCR was conducted using a forward primer located at exon I and a reverse primer that hybridizes immediately 5' of the GLI1 ATG codon (Table 1). This PCR revealed a much smaller product which was sequenced directly and found to consist of only one 5' non-coding exon. This alternative mouse GLI1 variant corresponds in both size and sequence to the published human transcript obtained from a glioma cell line (13,42) and was denoted the γ-UTR variant (FIG. 1A).

In order to determine how these alternative transcripts were generated, the inventors characterized the genomic organization of this region. Mouse genomic DNA was amplified using the primer pair mGliF1a [SEQ ID NO:18] and mGliR2 [SEQ ID NO:13] (Table 1). Sequence analysis of the 2.8 kb product identified the novel 119 nucleotide sequence within the α-UTR variant as an authentic exon (which the inventors denoted as exon 1b) that is flanked by 2.5 kb (intron 1a) and 115 bases (intron 1b) of intervening sequences (FIG. 1B). The identification of this additional non-coding exon required a change in the nomenclature used by the earlier study of Liu et al. (42), with exon II becoming exon 1a and exon III (which encodes the translation start site) renumbered as exon 2 (see FIG. 1B).

EXAMPLE 5

Expression of Mouse GLI1 5'UTRs

Figure 2A:
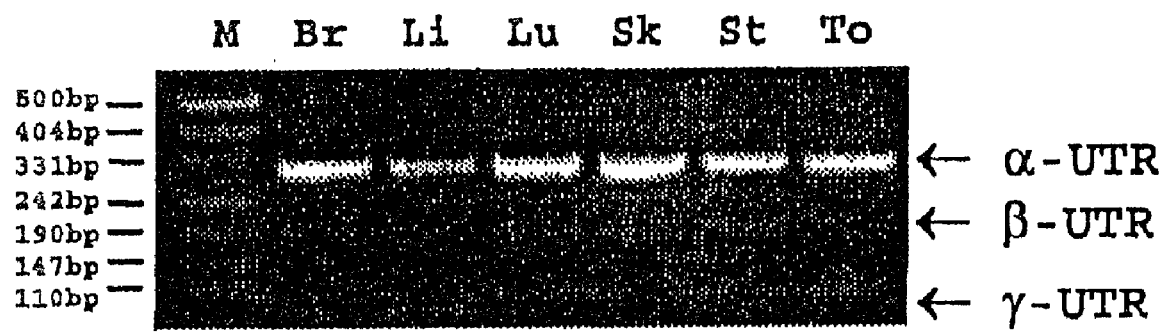
FIG. 2 is a photographic representation showing that expression of alternative GLI1 5'UTRs is not tissue specific but does show strain variation. RT-PCR was performed on mRNA isolated from brain (Br.), liver (Li.), Lung (Lu.), skin (Sk.), stomach (St.) and tongue (To.) tissues of a postnatal mouse (panel A). A signal for the β-UTR and γ-UTR variants is also present in all tissues examined but barely discernible. Panel B, in BALB/c, DBA and C57B1/6 strains, the α-UTR variant is the major transcript (BALB/c is shown in lane 1), whereas the β-UTR variant is the dominant transcript in CD-1 and SV129 strains (CD-1 is shown in lane 2)The DNA marker (M) is also indicated.
Figure 2B:
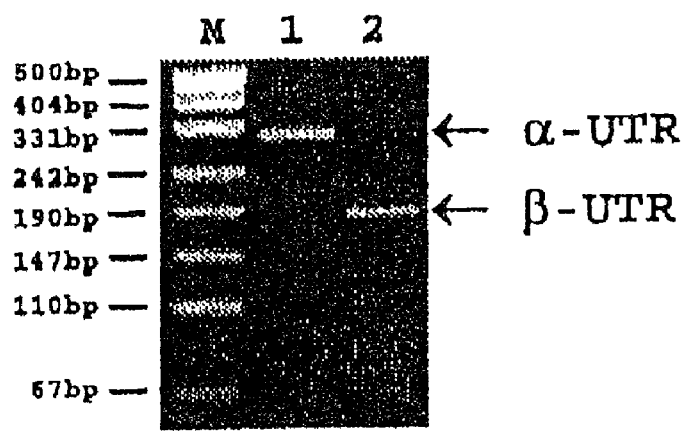

The expression of the alternative 5'UTR variants was determined in neonatal, juvenile and adult tissues from various mouse strains by RT-PCR (FIG. 2). This analysis revealed that the UTR variants had no particular tissue-specific expression pattern, but did show marked strain-specific differences. In all tissues examined, the larger UTR forms (α and β-UTR) predominate while the γ-UTR appears as a minor amplified product (FIG. 2A). In some strains, such as BALB/c, DBA and C57BL/6, the α-UTR variant was the major form, whereas in CD1 and SV129 strains, the β-UTR form was the predominant transcript (FIG. 2B). In Swiss outbred mice, expression of the α-UTR and β-UTR was heterogeneous with some animals expressing both forms and others expressing only one. In a given individual, the expression profile of the two larger transcripts was identical in all tissues examined irrespective of the strain used (FIG. 2A). The inventors also followed the expression of the UTR variants in postnatal skin development and found that the apparent levels of all GLI1 transcripts were reduced with increasing age and that the γ-UTR transcript was not detected at all in adult skin.

Figure 3:
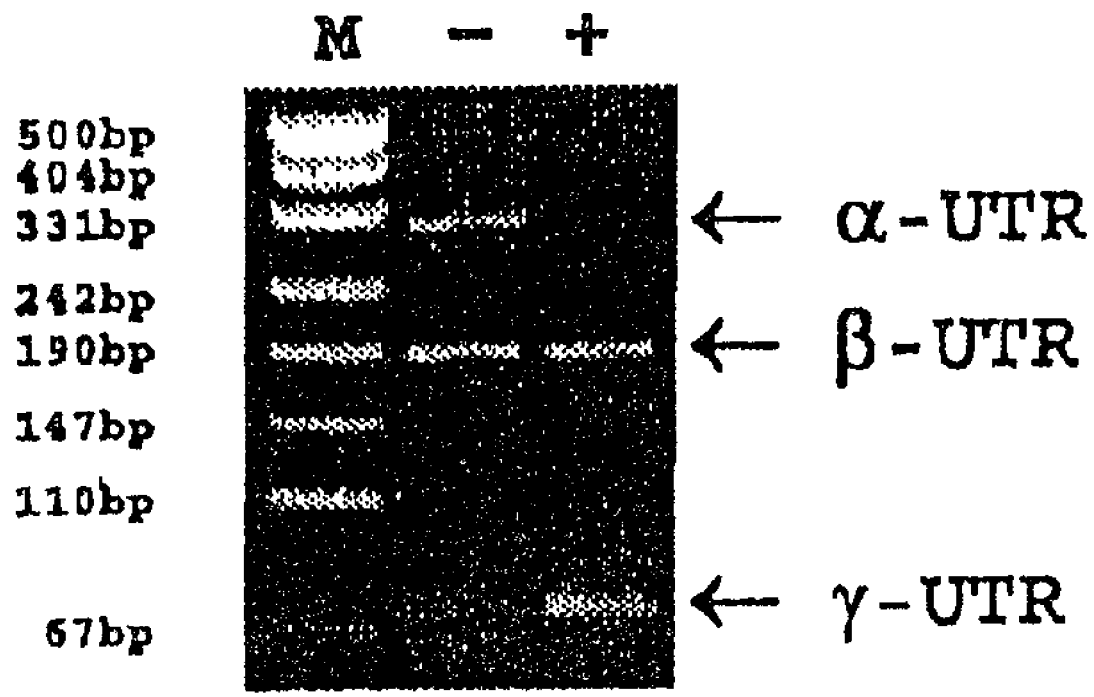
FIG. 3 is a photographic representation showing that expression of the GLI1 5'UTR variants is altered by TPA treatment. The expression of the γ-UTR transcript is increased, whereas expression of the α-UTR is reduced, in TPA treated skin (+) relative to control skin (−). The DNA size marker is indicated (M).

To evaluate whether the expression of these 5'UTR variants correlated with proliferative status, newborn and 7 day old animals were treated with TPA topically applied to back skin. These experiments revealed that expression of the larger UTR transcripts was maximally reduced at 3 hr post-application, whereas expression of the γ-form was increased (FIG. 3). Reduced expression of the α- and β-UTRs was still evident, albeit not as marked, 24 hr post-application). Since acute TPA treatment results in increased mitotic activity of the basal layer keratinocytes (44), these data indicate an association of the γ-UTR transcript with proliferation and the α- and β-UTRs with differentiation.

EXAMPLE 6

Identification of Alternative Human GLI1 5'UTRs

Figure 4A:
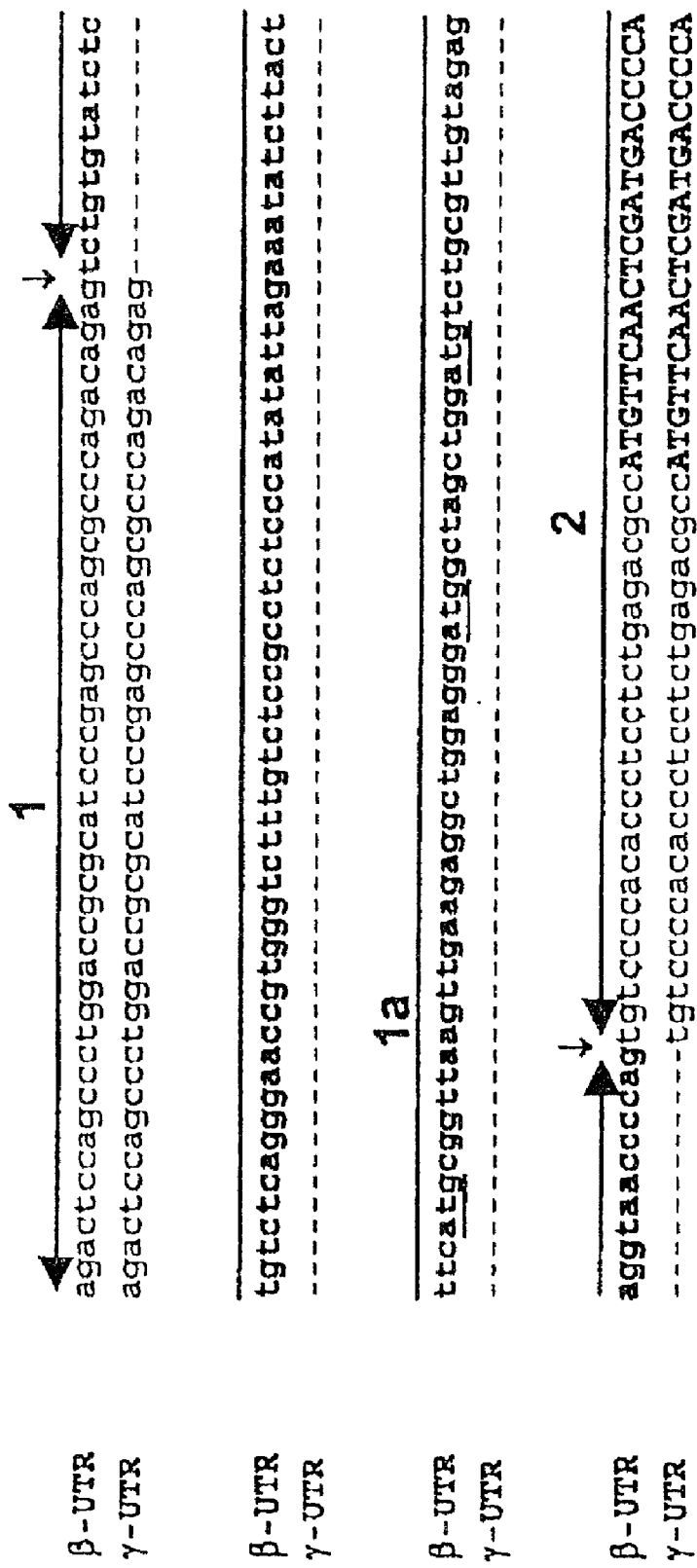
FIG. 4 is a representation of the sequence, exon composition and pre-mRNA structure of alternative human GLI1 5'UTRs, Panel A, sequence alignment of the alternative GLI1 5'UTR variants identified in human tissues (denoted β-UTR (SEQ ID NO: 64) and γ-UTR (SEQ ID NO: 65)). The novel 144 bp sequence of exon 1a is shown in bold lowercase lettering. The ATG codons denoting the beginning of uORFs are underlined and the main ORF encoding GLI1 is shown in bold uppercase lettering. The intron/exon boundaries are indicated by arrows. Panel B, schematic showing the exon composition of the alternative 5'UTRs and the organization of the pre-mRNA from which they are derived. Exons are denoted by open boxes and introns by solid lines with intron size shown. The translation start site (ATG) of the main ORF is located in exon 2 and indicated by a bent arrow. Panel C, comparison of human exon 1a sequences (SEQ ID NO: 66) with mouse exon 1a (SEQ ID NO: 67). Identical bases are indicated with *.
Figure 4B:
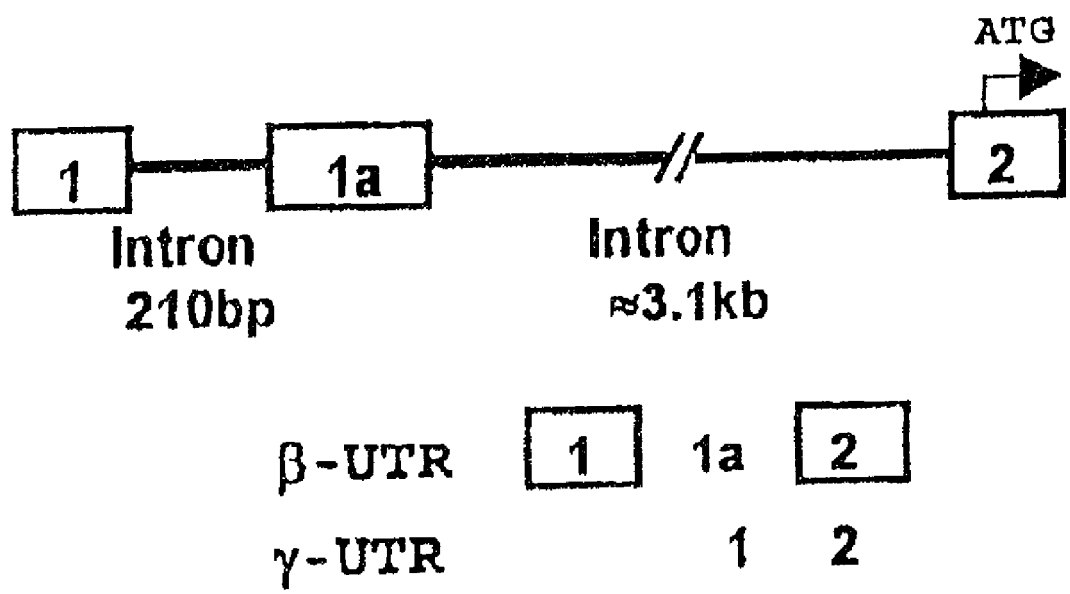

The inventors searched for alternative human GLI1 transcripts in newborn foreskin by RT-PCR with primers derived from exon 1 and exon 2 (Table 1) of the published sequence (13). Two PCR products were generated and sequenced, with the smaller fragment corresponding to the published sequence (13) and the larger containing an additional 144 bases located at the splice junction of exon 1 and exon 2 (FIG. 4A). The larger transcript was termed β-UTR and the smaller sequence as γ-UTR variant (FIGS. 4A and 4B). Notably, the novel 144 nucleotide sequence found within the human β-UTR has significant homology with mouse exon 1a, but is 30 bases larger and contains an additional two ATG codons (FIG. 4C).

Figure 5:
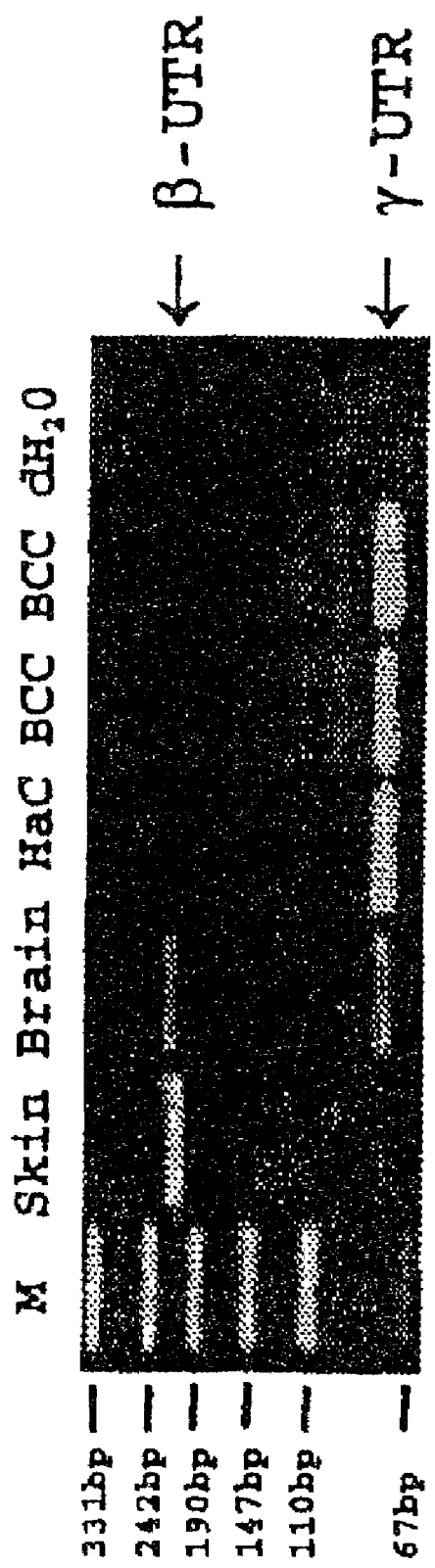
FIG. 5 is a photographic representation of the detection of human GLI1 5'UTR variants by RT-PCR. RT-PCR results from skin, brain, the HaCaT human keratinocyte cell line (HaC), two BCC biopsies and a no-RNA control (dH$_2$O) are shown. A DNA size marker (M) is also included.

The β- and γ-UTRs were also present in a brain sample and their identity was confirmed by sequence analysis (FIG. 5). The expression of the β- and γ-UTRs was further examined in HaCaT cells and seven BCC samples. The inventors found that the γ-transcript was present in proliferating cultures of HaCaT cells and all BCC samples but in contrast to foreskin keratinocytes and brain tissue, the inventors were unable to amplify the β-transcript from these mRNAs (FIG. 5). Therefore, the γ-UTR transcript may represent the major variant expressed by proliferating cells in human tissues as well.

EXAMPLE 7

Genomic Sequence of GLI1 5' UTRs

The partial mouse GLI1 UTR genomic sequence is shown in SEQ ID NOS:33 and 34 with a sequence between SEQ ID NO:33 and 34. Similarly, the partial human GLI1 UTR genomic sequence is shown in SEQ ID NOS:35 and 36, again with a sequence between SEQ ID NO:35 and 36. Complete genomic sequences for M-UTR and H-UTR are shown in SEQ ID NOS:59 and 60, respectively.

EXAMPLE 8

Functional Analysis of the GLI1 5'UTRs

The 5'UTR is known to regulate gene expression by influencing the efficiency of translation. An examination of the GLI1 5'UTR variants revealed three small upstream open reading frames (uORFs) in mouse α-UTR, two in human β-UTR, one uORF that overlaps the GLI1 ORF in mouse β-UTR and none in the γ-UTRs (Table 2). The secondary structure for each 5'UTR was analyzed using the RNA folding prediction program MFOLD (44). This program predicted extensive secondary structures in the longer UTRs, with calculated free energy values of −72.7 to −94.5 kcal/mol for the mouse α-UTR, −65 kcal/mol for the human β-UTR and −55 kcal/mol for the mouse β-UTR. The human and mouse γ-UTRs were predicted not to form stable secondary structures and to have free energy values of −12 kcal/mol (Table 2). The presence of uORFs and stable secondary structures in the larger UTRs suggest that they are less efficiently translated than the γ-variant that lacks these features.

Figure 6A:
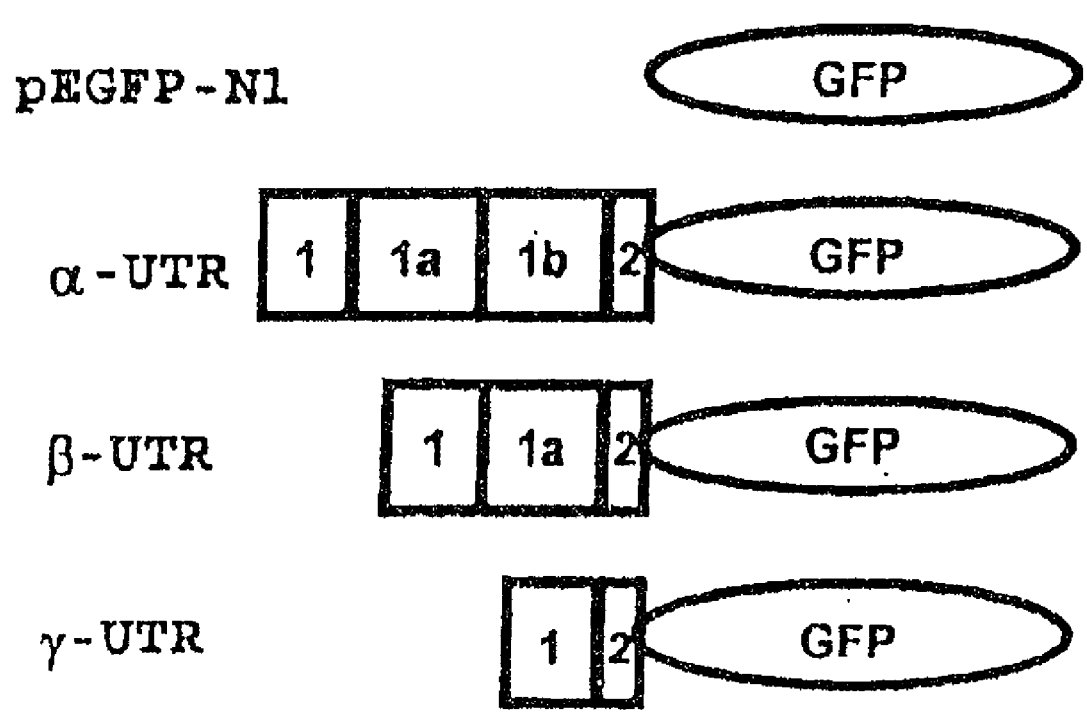
FIG. 6 is a representation of the GLI1 5'UTR variants differentially express a GFP reporter construct in transfected cells. Panel A, a diagram showing the GFP constructs used in the transfection studies. The mouse Gli1 5'UTR sequences were cloned upstream of the GFP ORF as indicated. pEGFP-N1 represents the parent GFP construct. Panel B, GFP fluorescence observed in Cos-1 cells transfected with the GFP expression vector alone (GFP), α-UTR- (α), β-UTR- (β) and γ-UTR- (γ) GFP constructs. Transfection efficiency was determined by counting GFP expressing cells, which revealed that each construct was transfected with the same efficiency (within experimental limits).
Figure 6B:
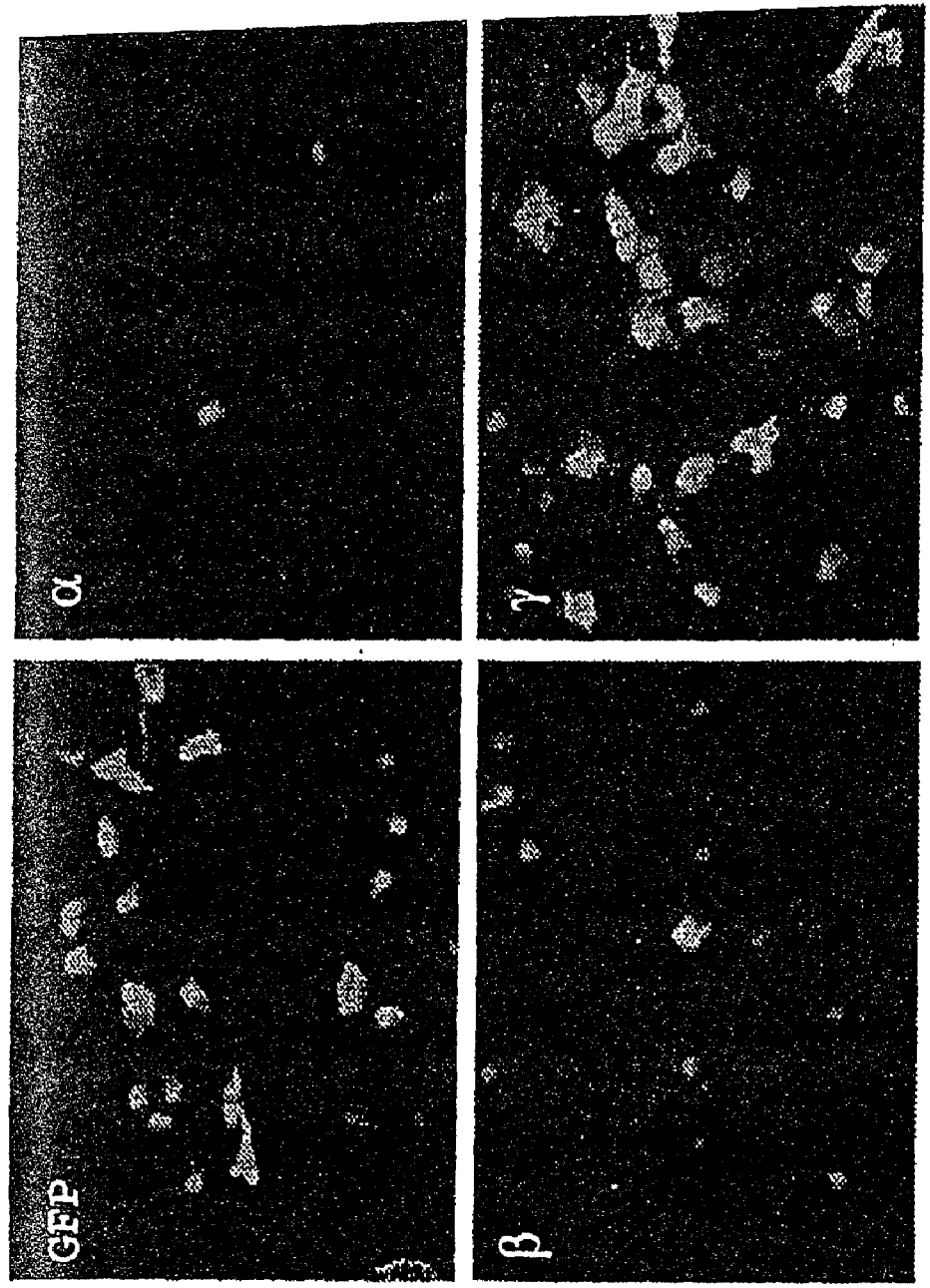

To test the above prediction in vivo, the three mouse GLI1 5'UTR fragments were cloned upstream of a GFP reporter gene (FIG. 6A) and the constructs transiently transfected into HaCaT, Cos-1 and BHK-21 mammalian cell lines and primary mouse skin fibroblasts. The difference in the levels of GFP produced by these constructs was striking (FIG. 6B), with the α-UTR construct producing the lowest fluorescence levels, the β-UTR construct producing immediate levels and the γ-variant producing the highest levels (even higher than the GFP vector control). Importantly, there was no apparent difference in the transfection efficiency of the constructs for a given cell type, showing that the increase in the number of brightly fluorescing cells transfected with the γ-form is due to an increase in GFP production.

Figure 7A:
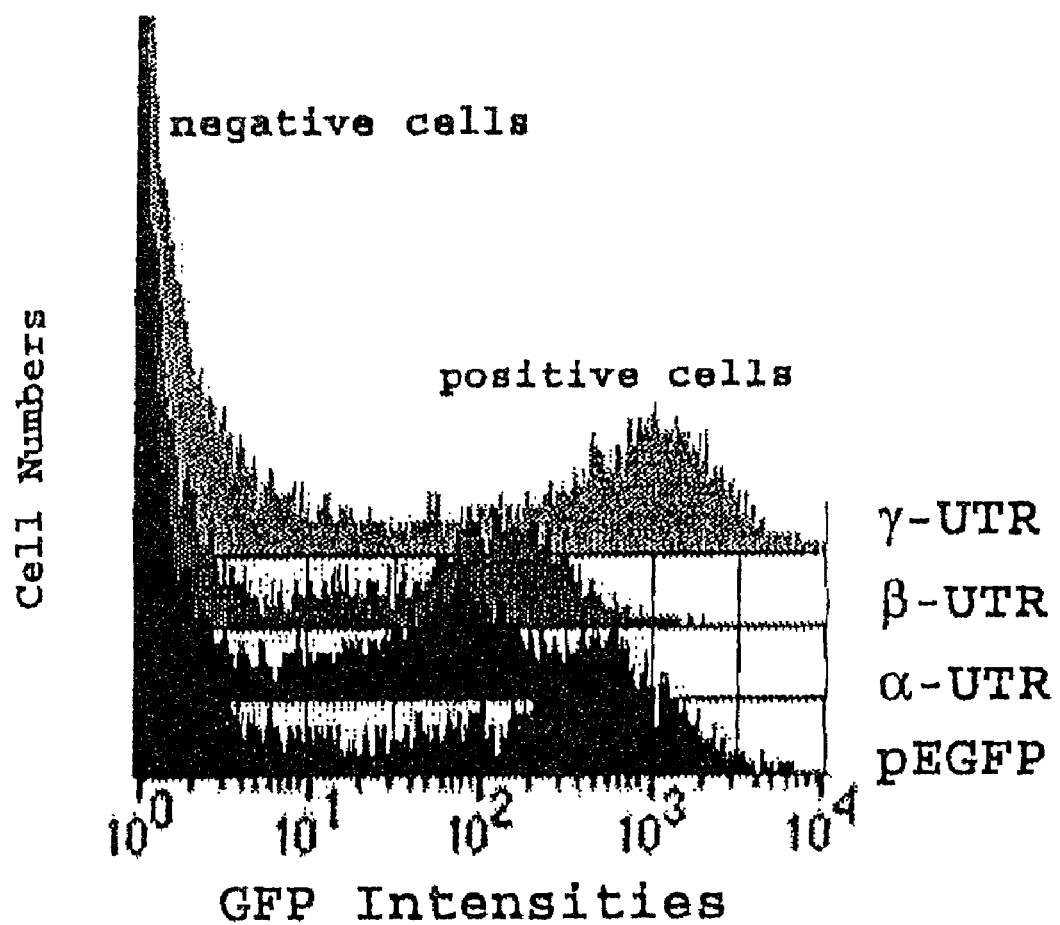
FIG. 7 is a representation of flow cytometry analysis of 5'UTR-GFP constructs in transfected cells. Panel A shows a fluorescence intensity histogram compiled from the analysis of twenty thousand cells per sample for each construct (see FIG. 6) in transfected Cos-1 cells. The peak closest to the vertical axis is due to untransfected cells (negative cells) which show low fluorescent intensities due to autofluorescence. The second peak represents fluorescence from transfected cells that express GFP. The four histograms representing each GFP construct were merged to allow direct comparison of fluorescence intensities. This analysis revealed that the γ-UTR construct produced the highest GFP intensities (mean value $1.045 \times 10^3$) and the α-UTR the lowest (mean value $6.2 \times 10^1$). Panel B, graphical representation of GFP intensities of the 5'UTR variants relative to the empty GFP vector (defined as 100) in transfected BHK-21 (BHK), Cos-1 and HaCaT cells. Panel C, graphical representation of the ratios of GFP intensities between 5'UTR variants in the cell lines indicated. The γ-UTR/α-UTR (■ γ/α) and γ-UTR/β-UTR (□ γ/β) ratios are shown for constructs transfected into BHK-21 (BHK), Cos-1, primary mouse skin fibroblasts (MSF) and HaCaT cells. The largest differences in GFP fluorescence between the γ-UTR and the α- and β-UTR variants was observed in HaCaT cells. The values shown are the averages of three independent transfection and cell sorting experiments.
Figure 7B:
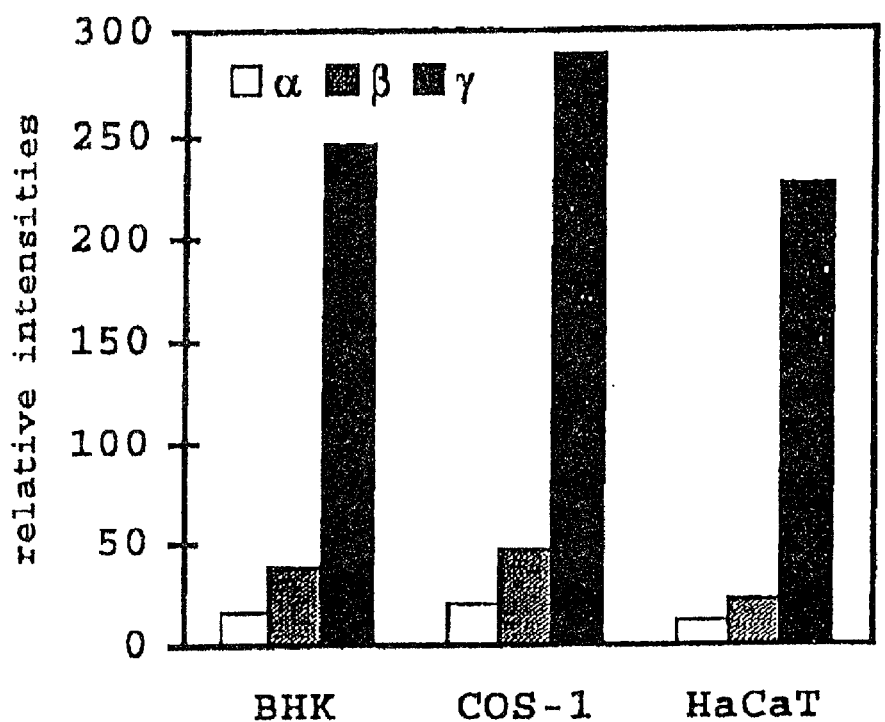
Figure 7C:
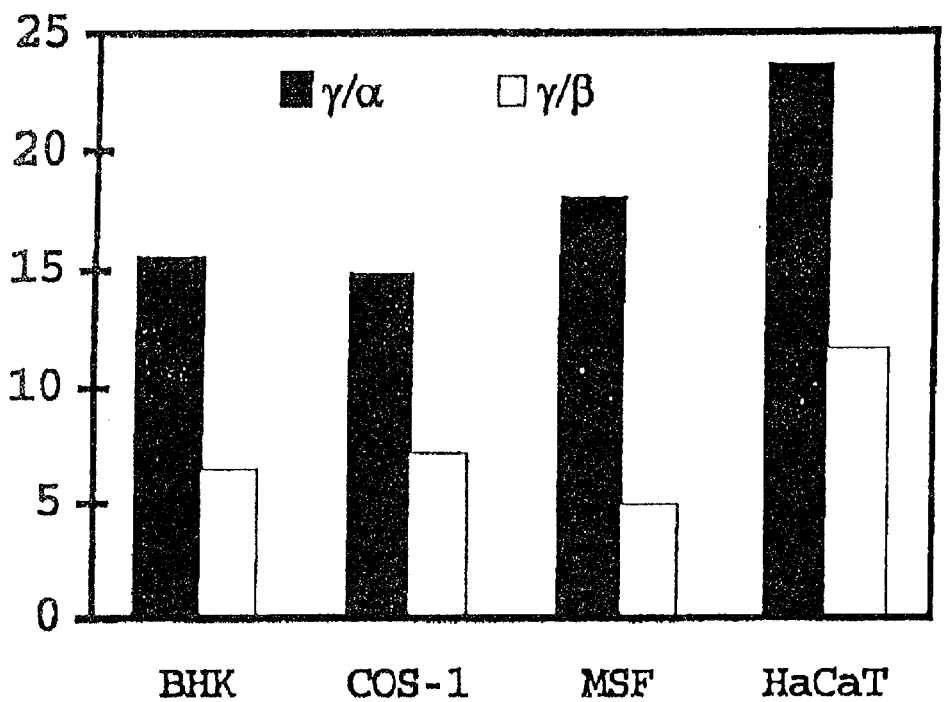

To quantify these results, cells were also subjected to flow cytometry analysis (FIG. 7A). The advantages of this technique over enzymic reporter assays are that GFP levels are determined in individual cells using a large number of cells (20,000 cells/construct) and untransfected cells are discarded from the calculations thus removing any bias due to transfection efficiencies. This analysis revealed that the α- and β-UTRs expressed the reporter 60–90% lower than the GFP vector control and whereas the γ-UTR produced 2–3 fold enhancement of expression (FIG. 7B). Comparison of expression levels between the three variants reveals a 14–23 fold increase in GFP production by the mouse γ-UTR construct over the α-UTR (γ/α) and a 5–13 fold increase over the β-UTR (γ/β) (FIG. 7C). The greatest differences in GFP intensities were seen in HaCaT cells. These data show that the γ-UTR facilitates expression of a heterologous protein whereas the α- and β-UTRs significantly suppress protein production.

Figure 8:
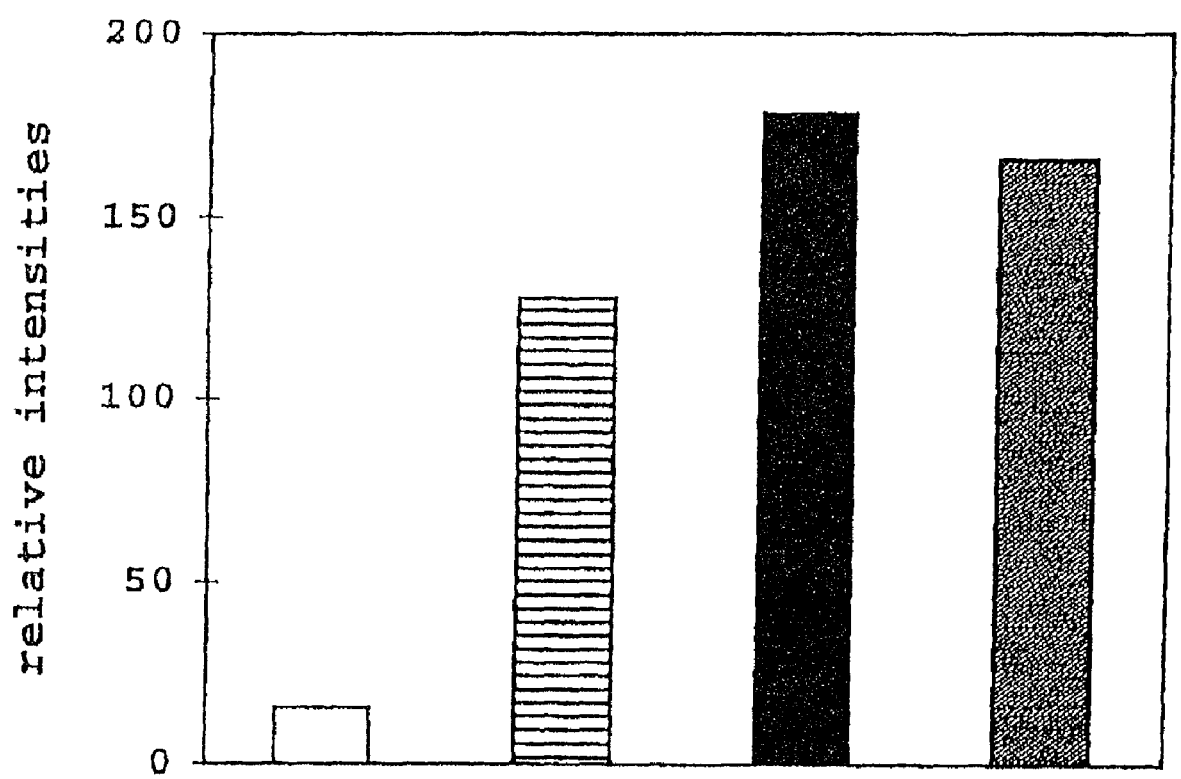
FIG. 8 is a graphical representation showing flow cytometry analysis of mutant 5'UTR-GFP constructs in transfected cells. A graphical representation of GFP intensities of wild-type α-UTR (α), mutant α-UTR ($α^{mut}$), wild-type γ-UTR (γ) and the 4mer γ-UTR ($γ^{x4}$) constructs relative to the empty GFP vector in Cos-1 cells. The values shown are the averages of three independent transfection and cell sorting experiments.
Figure 9:
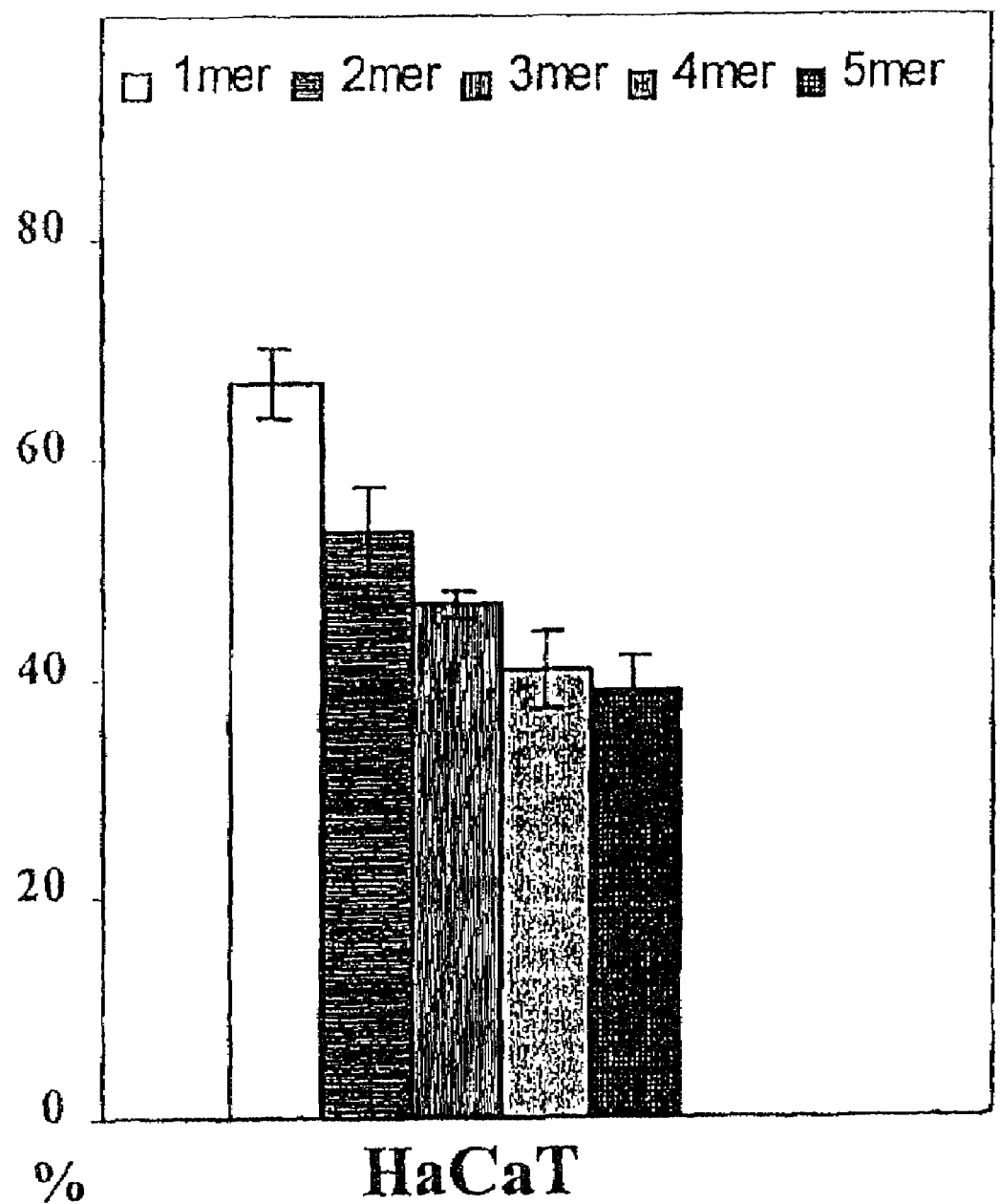
FIG. 9 is a representation showing that increasing numbers of uORFs in a 5' leader sequence prior to a reporter gene decreased the level of expression represented as a percentage.

In order to determine whether this suppression is due to the presence of uORFs or some other property of the longer UTRs, such as increased secondary structure, two additional constructs were made. The uORFs of the α-UTR variant were removed by mutating all four upstream ATG codons to TTG. Significantly, the mutant α-UTR construct expressed the reporter at levels that approached that of the γ-UTR construct (FIG. 8). To ascertain whether the length of UTR sequence could influence expression levels, the inventors produced a γ-UTR multimer containing four copies of this sequence in the same orientation. The γ-UTR multimer, which contained 314 bp compared to the 307 bp of the α-variant, produced GFP levels that were only marginally lower than a single copy of the γ-UTR (FIG. 8). Taken together these data show that the uORFs of the Gli1 UTRs play a major role in the suppression of protein production.

In the following Examples, genetically modified plants were generated to show the effects of the GLI1 leader sequences on gene expression.

EXAMPLE 9

Plant Material and General Growth Conditions

Wild-type tobacco (*Nicotiana tobaccum*) line D38 was grown in the glasshouse to produce leaves for the transient assays with a GUS reporter gene carrying the various GLI 5' UTRs.

Wild-type *Arabidopsis thaliana* (C24) was used in stable transformation experiments. Seeds were sprinkled over moist, sterilised potting mix and covered with a thin layer of finely ground vermiculite. To synchronize germination, seeds were stratified by placing pots at 4° C. for 3–5 days. Plants were then transferred to a growth cabinet and grown at 20° C. under long days (16 hr photoperiod) to induce flowering. The soil was watered daily. Growth conditions for selection of transgenic *Arabidopsis* are given below.

EXAMPLE 10

General Cloning Techniques

Below is a summary of the cloning techniques used to generate the constructs.

Restriction Enzyme Digests

All restriction enzymes used in the construction of the vectors were provided by New England Biolabs and digests were carried out in the appropriate buffers as specified by the manufacturer. In general, three to five times the recommended dosage of enzyme was used. Digestions were carried out at 37° C. for a minimum of 3 hr to ensure complete digestion.

Agarose Gel Electrophoresis and DNA Fragment Purification

Agarose gels were prepared using analytical grade agarose (Progen, Australia) dissolved in 1× Tris borate EDTA (TBE). DNA samples were combined with gel loading buffer (62) and electrophoresed at 6V/cm. Following electrophoresis, gels were stained in ethidium bromide (0.5 μg/mL) and photographed on a UV transilluminator. DNA fragments were purified from agarose gels using Qiagen's QIAquick Gel Extraction Kit, following the manufacturer's instructions.

Ligation of Plasmid DNA

All ligations except for those involving pGemT-easy were conducted using New England Biolabs T4 DNA ligase and the appropriate buffer in a volume of 10 or 20 μL at 16° C. for 16 hr. A molar ratio of 1:3 (vector to insert) was most commonly used for intermolecular ligations, with a reaction containing either 100 ng for smaller *E. coli* cloning vectors or 300 ng for larger binary vectors.

Transformation of DH5α Competent Cells

50 μL of DH5α competent cells were thawed on ice for approximately 10 min. The ligation reactions were then added to the cells, and incubated on ice for 30 min. The cells were then heat-shocked for 30 sec at 42° C. and immediately placed back on ice for 5 min. An 800 μL aliquot of SOC media (62) was added and the cells were then incubated at 37° C. for 1 hr. Either 50 or 100 μL of the solution was then spread onto LB plates containing the appropriate antibiotic and the plates incubated overnight at 37° C.

Screening Colonies for Ligation Products

For initial cloning into pGEMT-easy, the selection was based on blue white selection (62). For other cloning experiments, colonies were selected at random (due to the lack of blue white selection) and sampled with a sterile pipette tip. The tip was then dipped into a 20 μL diagnostic PCR containing 0.2 μM of each diagnostic oligonucleotide primer (which varied depending on the ligation), 200 μM dNTPs, in a buffer containing 10 mM Tris (pH 8.3), 50 mM KCl, 1.5 mM MgCl$_2$, 0.001% w/v gelatin, and 0.5 U of Taq DNA polymerase. The pipette tip was then used to inoculate a 5 mL LB culture (containing the appropriate antibiotic), which was then incubated at 37° C. with shaking (100 rpm) for 16 hr. Diagnostic primers were chosen to identify plasmids containing the appropriate insert. The PCR reactions were loaded into a PTC™-100 Thermal Controller and after a 5 min 94° C. hot start, were cycled as follows: 10 cycles at 94° C. (15 sec), 60° C. (15 sec), 72° C. (45–180 sec depending on product size), then 25 cycles at 94° C. (15 sec), 57° C. (15 sec), 72° C. (45–180 sec). PCR products were then run on an agarose gel and visualized to identify recombinant plasmids.

Plasmid Purification

Cultures identified by PCR as containing the desired recombinant plasmids were subsequently minipreped using the BRESAspin™ (Geneworks) plasmid Mini-Kit following manufacturer's protocols. Diagnostic restriction enzyme digests were then performed to confirm the orientation or presence of the desired insert. If large quantities of the plasmid were required (e.g. for low copy number binary vectors), a larger volume (up to 400 mL) of LB containing the appropriate antibiotic was inoculated with a fresh colony containing the plasmid of interest and grown at 37° C. with shaking (100 rpm) for 16 hr. The plasmid was then extracted using either the BRESApure™ (Geneworks) plasmid Midi-Kit or Maxi-kit (depending on culture volume), according to the manufacturer's instructions.

EXAMPLE 11

Amplification of GLI Sequences for Dimming Constructs

The template for the PCR was 1 ng of pGEMT-easy (Promega, USA) containing the respective α, β or γ sequences from murine GLI1. The 5' oligonucleotide primer used to amplify all sequences in the PCR was designated GLI5'-SacI and its sequence was: 5'-TT GAGCTCAGTTCCAGCCCTGG-3 [SEQ ID NO:37]. A SacI site (underlined) was incorporated at the 5' end to facilitate later cloning steps. The 3' oligonucleotide primer designed to amplify all sequences was designated GLI3'-NcoI and its sequence was: 5'-AA CCATGGCGTCTCAGGGAA-3 [SEQ ID NO:38] and contained an NcoI (underlined) site.

The PCR was carried out on 1 ng of template in a total volume of 20 μL in the presence of 0.1 μM of the primers, 200 μM of dNTPs, 1.25 units of PFU DNA polymerase in the recommended buffer (Stratagene, USA). The samples were loaded into a PTC™-100 Thermal Controller (MJ Research, Inc., MA, USA) pre-heated to 85° C. The PCR started with 10 cycles at 94° C. (15 sec), 58° C. (15 sec), 72° C. (30 sec) followed by 25 cycles at 94° C. (15 sec), 55° C. (15 sec), 72° C. (30 sec). The total PCR reactions were electrophoresed on a 2% w/v agarose gel and the products purified using the Qiagen QIAquick Gel extraction kit. The purified DNA fragments were cloned into pGEMT-easy (Promega, USA) following the manufacturer's recommendations. The plasmid containing the α clone was called UQC1421, the plasmid containing the β fragment was designated UQC1431, and the plasmid containing the γ fragment was called pUQC1441. These fragments were subsequently authenticated by sequencing and comparison to the known sequences. Sequencing reactions were prepared using a PRISM Ready Reaction Bigdyedeoxy terminator kit (Applied Biosystems). The 20 μL reaction volumes contained 8 μL of reaction mix, 0.32 μM M13 F (5'-GGTTTCCCAGTCACCGAC-3' [SEQ ID NO:39]) or M13 R (5'-ACACAGGAAACAGCTATGACC-3' [SEQ ID NO:40]) and 500 ng of template plasmid. Twenty-five cycles of PCR were run at 94° C. for 10 sec, 50° C. for 5 sec and 60° C. for 4 min. Excess dye terminators were removed from the reaction mixture by a sodium acetate/ethanol precipitation, according to the manufacturer's instructions. The reactions were run on an Applied Biosystem 377 DNA sequencer. These α, β and γ fragments were used to make the dimming constructs described below.

EXAMPLE 12

Construction of Dimming Plasmids

Figure 10A:
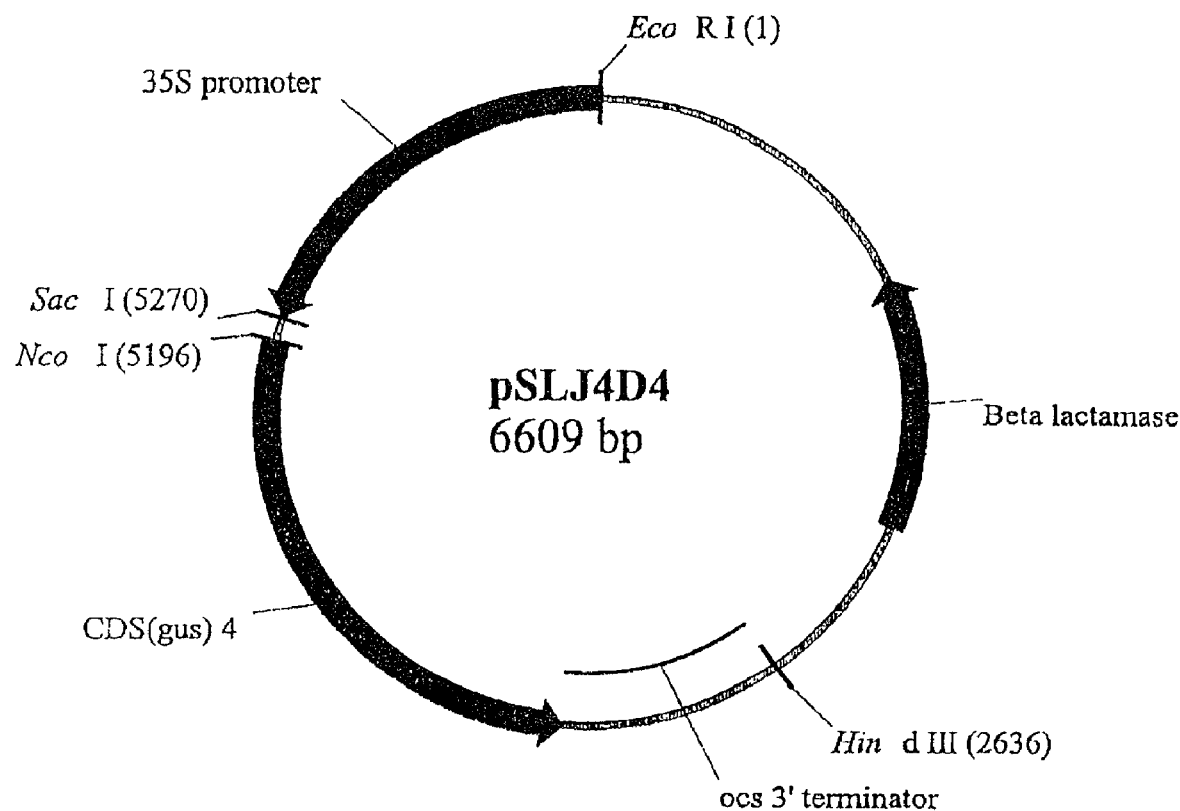
FIG. 10 is a diagrammatic representation of plasmid constructs (A) pSLJ4D4 and (B) pUQC1411.
Figure 10B:
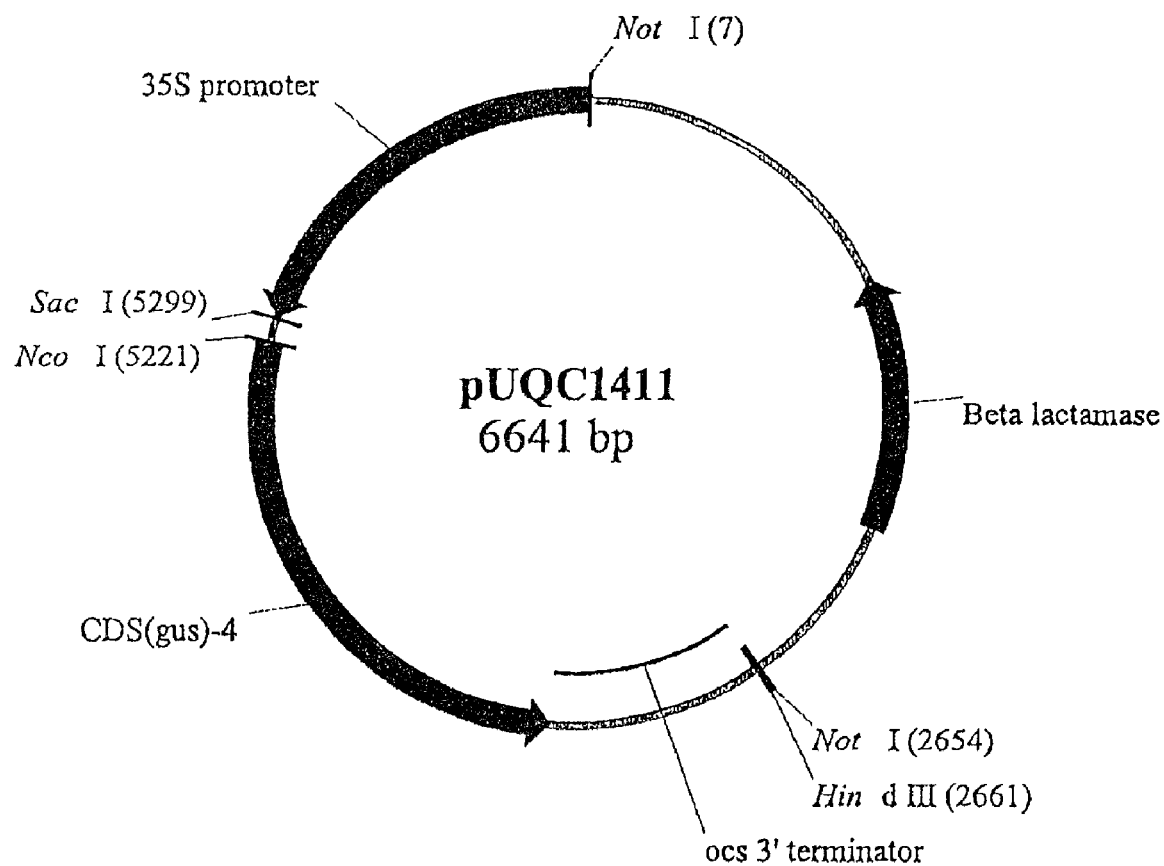

Two Not I sites were created to facilitate the cloning of the 35S:gli:GUS:ocs transgene into the binary vector pUQC477. To achieve this, SLJ4D4 (FIG. 10A) was digested with EcoRI, and ligated to a linker containing a NotI site. The resulting construct, designated pUQC1401, was then used in an additional ligation step to introduce a second NotI. This was done by digesting pUQC1401 with HindIII and ligating to a linker containing another NotI site. The resulting plasmid was named pUQC1411 (FIG. 10B).

Figure 11A:
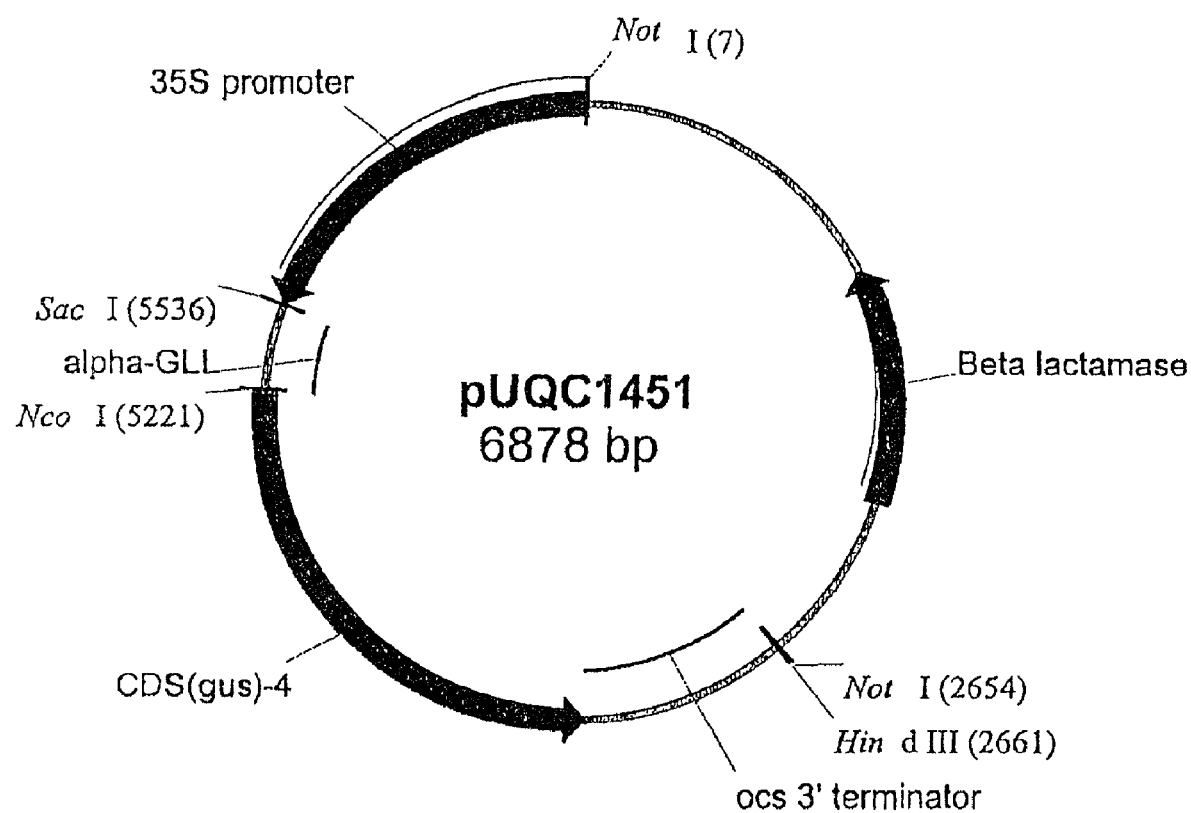
FIG. 11 is a diagrammatic representation of plasmid constructs (A) pUQC1451, (B) pUQC1461 and (C) pUQC1471.
Figure 11B:
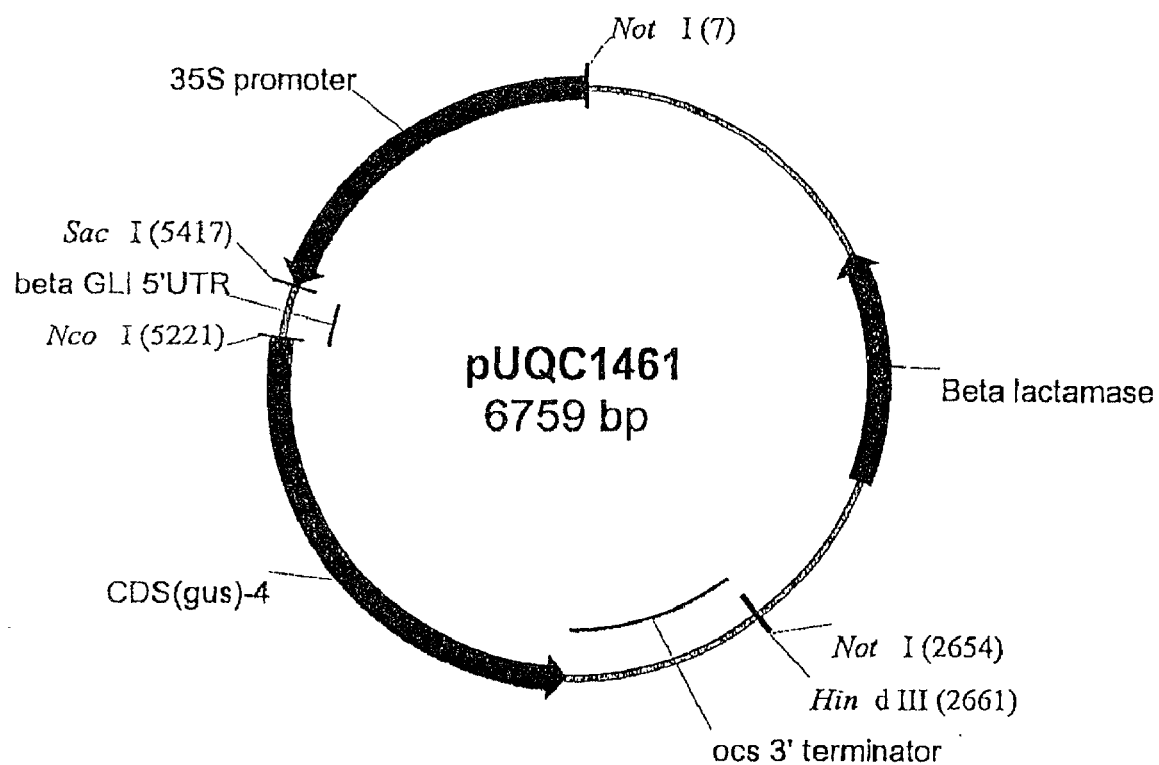
Figure 11C:
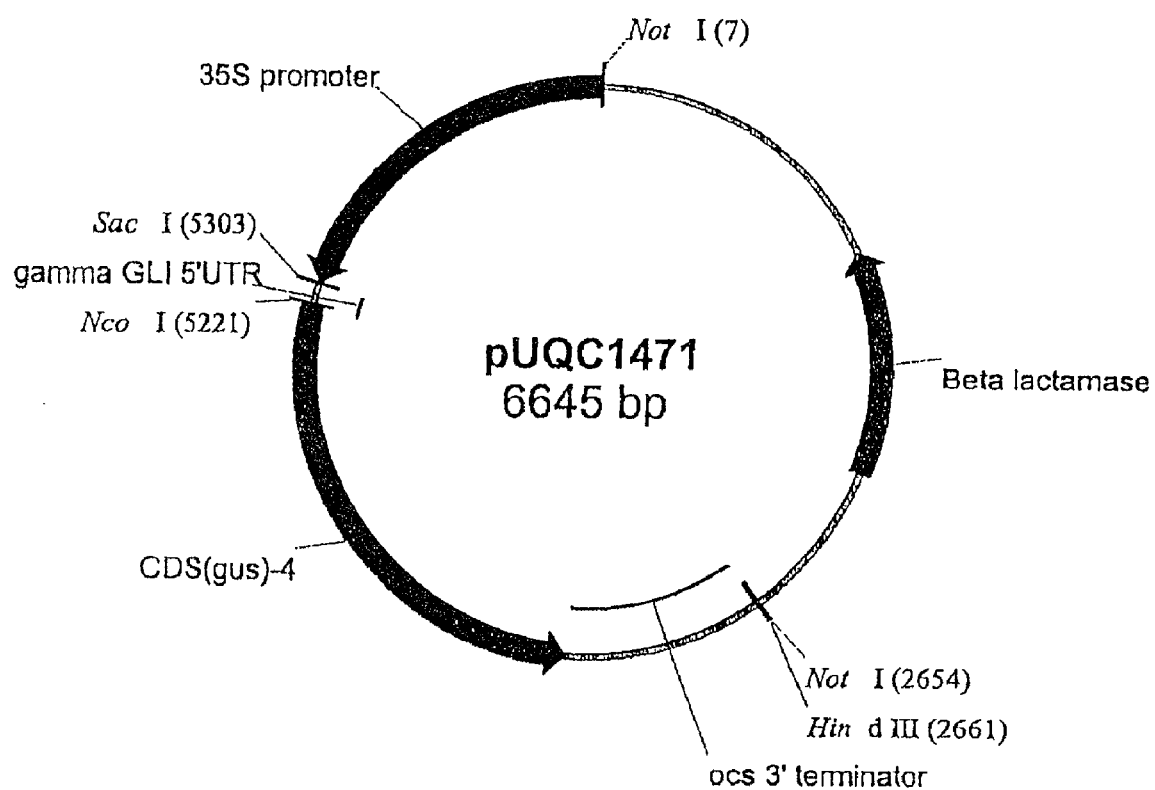

The following procedures were used to make the murine GLI1 α, β and γ dimming constructs. The dimming sequences were excised from pUQC1421 (α), pUQC1431 (β) and pUQC1441 (γ) with SacI and NcoI, and ligated into the corresponding sites between the 35S promoter and GUS coding sequence of pUQC1411. The resulting plasmids were designated pUQC1451 (α-GUS) [FIG. 11A), pUQC1461 (β-GUS) [FIG. 11B) and pUQC1471 (γ-GUS) [FIG. 11C). These plasmids as well as the unmodified pUQC1411 (Ω GUS) were used in the transient assays as well as further cloning steps.

Figure 12A:
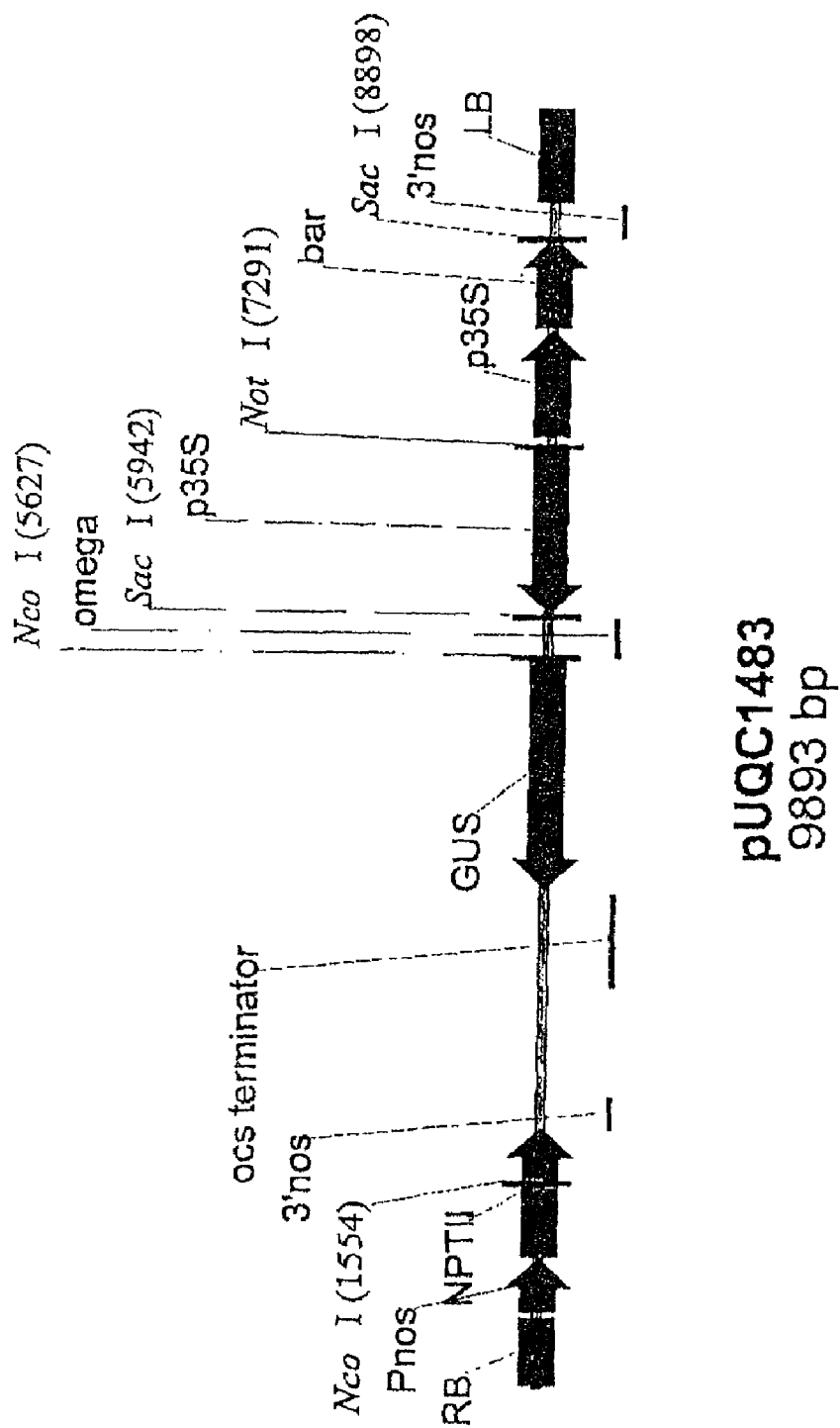
FIG. 12 is a diagrammatic representation of plasmid constructs (A) pUQC1483, (B) pUQC1495, (C) pUQC1501 and (D) pUQC1511.
Figure 12B:
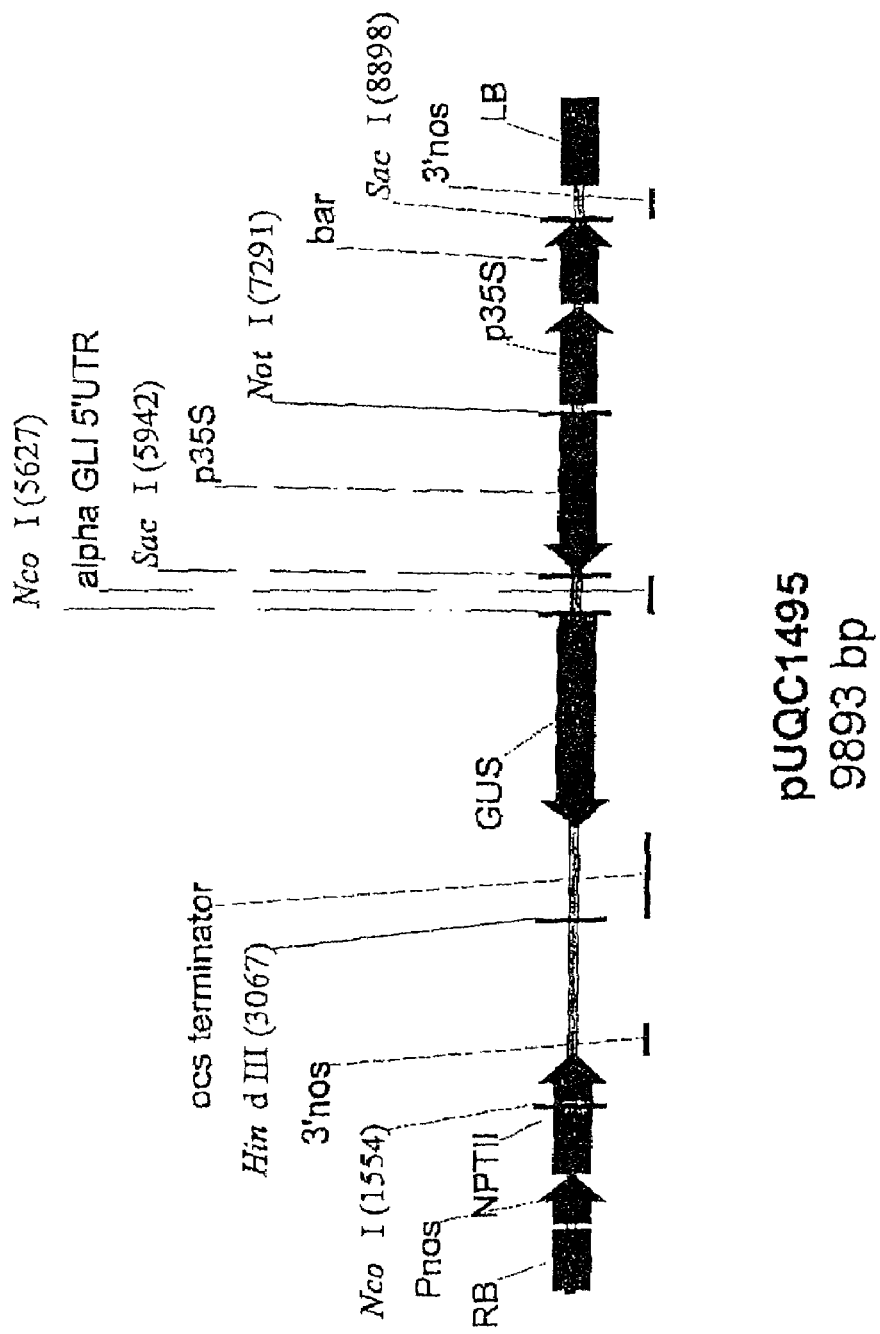
Figure 12C:
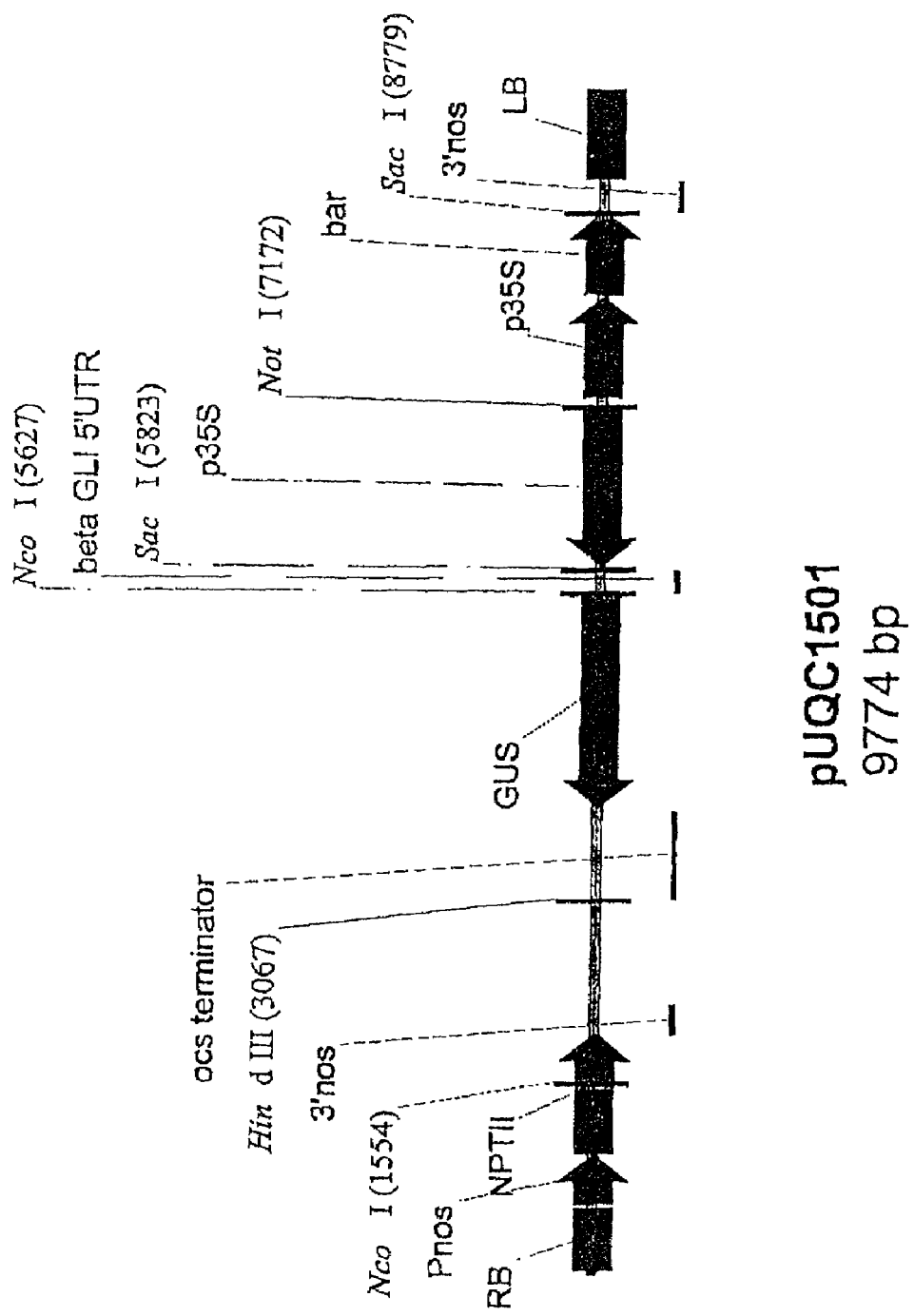
Figure 12D:
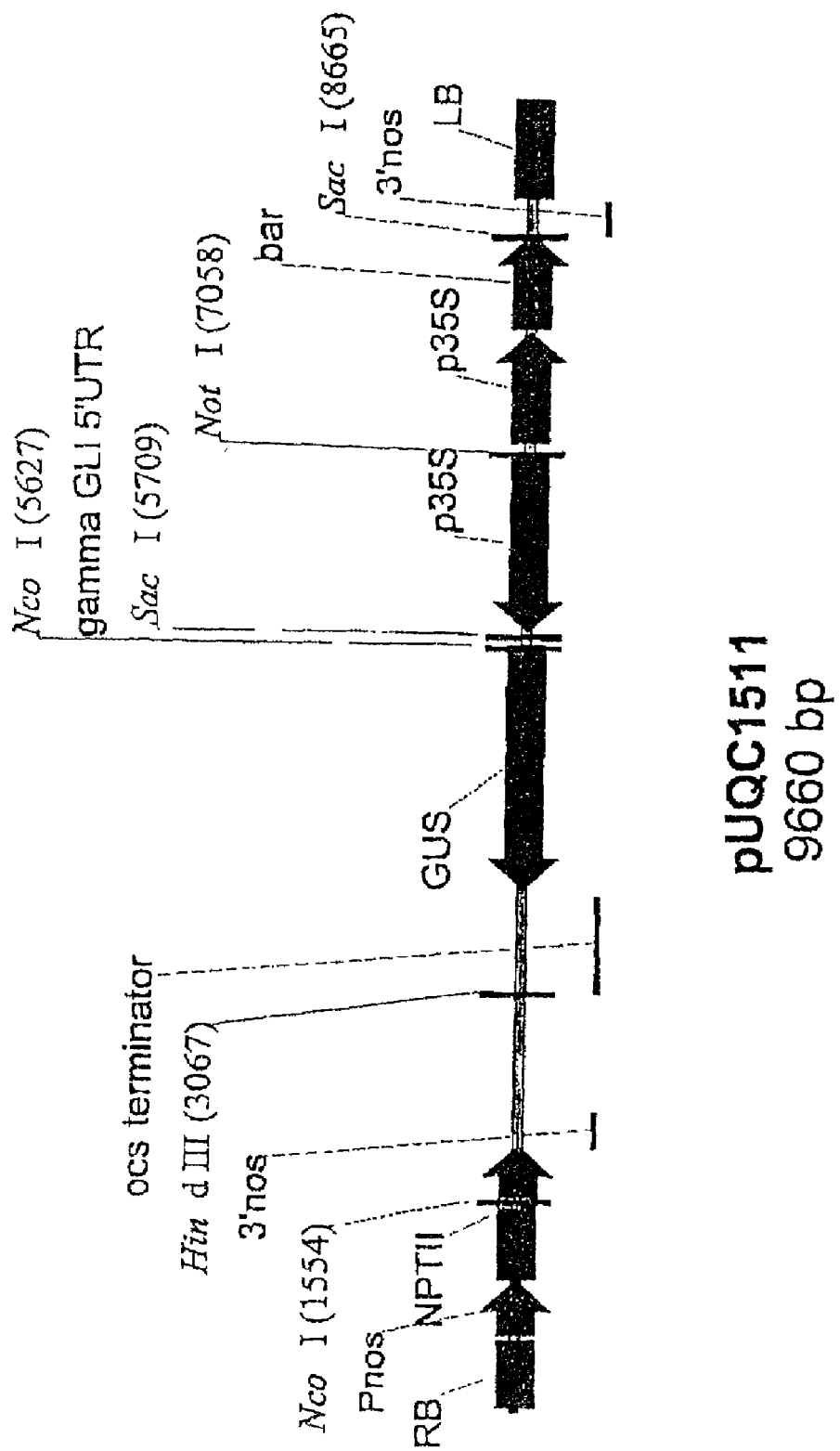

The binary vector used for *Arabidopsis* transformation was called UQC477 and was a modified version of the vector pNB96. pNB96 was digested with HindIII to remove a superfluous 1 kb insert. This vector was ligated to an oligonucleotide containing a NotI site that restored the HindIII site on one side of the ligation but not the other. The resulting construct (UQC477) contained a NotI site to facilitate cloning of the GUS transgene inserts and HindIII site on one side to facilitate future cloning. Three binary constructs were created using UQC477 as a backbone. The plasmids pUQC1411 (Ω GUS transgene), UQC1451 (α GUS transgene), pUQC1461 (β GUS transgene), pUQC1471 (γ GUS transgene) all contained NotI sites flanking the respective GUS transgene. The NotI sites were used to excise the transgenes and insert them into the NotI site of the binary vector UQC477. The inserts were orientated such that the 35S promoter of the GUS transgene was adjacent to, but in the opposite direction to the truncated 35S promoter controlling the BAR gene of the binary vector. The resulting binary vectors were called pUQC1481 (Ω GUS transgene) [FIG. 12A], pUQC1495 (α GUS transgene) [FIG. 12B], pUQC1501 (β GUS transgene) [FIG. 12C] and pUQC1511 (γ GUS transgene) [FIG. 12D).

EXAMPLE 13

Transient GUS Assays in Tobacco Leaves

Transient assays were performed using tungsten particle bombardment on tobacco leaves using a particle inflow gun. Tissue cultured tobacco leaves were cut into small pieces (approximately 0.5 cm$^2$) and placed on damp Wattman paper inside a sterile petri dish. The tungsten particle/plasmid DNA suspension was prepared by mixing, 25 µl of sterile tungsten particles (100 ng/µl), 5 µl plasmid DNA (1 µg/µl), 25 µl CaCl$_2$ (2.5 M) and 10 µl spermidine 0.1 M) in a sterile Eppindorf. The mixture was incubated at 4° C. for 5 minutes upon which 50 µl of the supernatant was removed and the remaining particles resuspended. 5 µl of the tungsten particle/DNA suspension was placed in the center of a screen in a syringe filter unit. The leaf pieces were placed 17 cm from the screen and protected by a baffle made of 500 mm nylon mesh. A vacuum of about 300 mm Hg was applied and the tungsten particles were discharged when helium at 80 PSI released. The leaf pieces were then incubated at 37° C. over night and subsequently stained for GUS activity for 16 hr using a staining buffer consisting of 50 mM NaPO$_4$ (pH 7.0), 5 mM K ferricyanide, 5 mM K ferrocyanide, 0.3% Triton X-100 and 5 mg X-Gluc (per 10 ml) in a 2 ml Eppindorf. Leaf pieces were then cleared of chlorophyll using 70% v/v EtOH and viewed for GUS expression.

EXAMPLE 14

Transformation of *Arabidopsis thaliana*

*Arabidopsis thaliana* was transformed using *Agrobacterium tumefaciens* via the floral dip method as described. The four constructs (pUQC1481, pUQC1495, pUQ1501 and pUQC1511) described below were transformed using the following summary of the floral dip.

Conjugation of Binary Constructs into *Agrobacterium tumefaciens*

Binary vectors were conjugated into *A. tumefaciens* by a tri-parental mating method. *Agrobacterium* was grown in a 10 mL LB culture containing 50 µg/mL rifampicin for 36 hr at 28° C. Ten milliliter cultures containing 50 µg/mL of both a helper *E. coli* strain (pRK2013) and *E. coli* containing the binary vector of interest were grown for 12 hr at 37° C. Each culture was spun down at 3000 rpm for 10 min and the pellet resuspended in 1 mL of LB. On an LB plate free of selection, 30 µL of each suspension was combined together and grown at 28° C. for 16 hr. A streak from this plate was then grown on a plate containing 50 µg/mL rifampicin, 50 µg/mL kanamycin for 48 hr at 28° C. A single colony from this plate was then selected and grown on a plate containing the same selection, at 28° C. for 48 hr. The integrity of the transgene in the *A. tumefaciens* was confirmed with a diagnostic PCR test.

Preparation of *Agrobacterium* for *Arabidopsis* Transformation

A single transformed colony was used to inoculate a 5 mL LB pre-culture containing 50 µg/mL rifampicin and 50 µg/mL kanamycin. After 48 hr at 28° C., the pre-culture was used to inoculate a 250 mL LB solution containing 50 µg/mL kanamycin. This culture was grown for 18–24 hr at 28° C. and spun down at 5000 rpm for 10 min.

Transformation of *Arabidopsis*

The transformed *Agrobacterium* pellet was resuspended in a 600 mL, 5% w/v sucrose solution and supplemented with 300 µL of the surfactant Silwet L-77 (0.05%). Plants which had their primary bolts clipped and had numerous secondary bolts with floral buds were used in the transformation. The above ground parts of the plant were submerged and mildly agitated for 3–5 seconds. The plants were then covered to maintain high humidity for 24 hr. The transformed plants were then grown normally and had seed catchers (modified plastic soft drink bottles) attached until the time of seed harvesting.

Selection of T1 Transgenics

Selection was carried out under phosphinothricin (PPT) selection (15 µg/mL) on 1×MS media supplemented with 1% w/v sucrose (Merck, Australia) and 1% w/v agar (Becton Dickenson, USA).

In the following Examples, single and double nucleotide substitutions are made to GLI1 leader sequences to introduce AUG or GUG pseudo-initiation sites. The $N_V$ is also provided.

EXAMPLE 15

Mα-UTR aguuuccagcccuggaccacgcaucccgagcaccgcgccccgacggaggucucuuugucc [SEQ ID NO:41]
gcgccucucccacauacuagaaaucucucccuuucuugagguugggaugaagaagcaguu
gggacggccagcuggaggucugcgugguagagggaacuccagagacuguggaucgccaag
acugaacggcugcuucugcccacucuuugggauguuucuucuuaaggaagcugaaaaacg
uuauugauuccaugaccaguuucugagaugaggguuagagguccccuccauccuucccug
agacgcc.

$N_V$=4.6

EXAMPLE 16

Mα-UTR+1 AUG aguuucAUgcccuggaccacgcaucccgagcaccgcgccccgacggaggucucuuugucc [SEQ ID NO:42]
gcgccucucccacauacuagaaaucucucccuuucuugagguugggaugaagaagcaguu
gggacggccagcuggaggucugcgugguagagggaacuccagagacuguggaucgccaag
acugaacggcugcuucugcccacucuuugggauguuucuucuuaaggaagcugaaaaacg
uuauugauuccaugaccaguuucugagaugaggguuagagguccccucauccuucccug
agacgcc.

$N_V$=5.6

EXAMPLE 17

Mα-UTR+2 AUG aguuucAUgcccAUgaccacgcaucccgagcaccgcgccccgacggaggucucuuugucc [SEQ ID NO:43]
gcgccucucccacauacuagaaaucucucccuuucuugagguugggaugaagaagcaguu
gggacggccagcuggaggucugcgugguagagggaacuccagagacuguggaucgccaag
acugaacggcugcuucugcccacucuuugggauguuucuucuuaaggaagcugaaaaacg
uuauugauuccaugaccaguuucugagaugaggguuagagguccccucauccuucccug
agacgcc.

$N_V$=6.6

EXAMPLE 18

Mα-UTR+3 AUG aguuucAUgcccAUgaccaUgcaucccgagcaccgcgccccgacggaggucucuuugucc [SEQ ID NO:44]
gcgccucucccacauacuagaaaucucucccuuucuugagguugggaugaagaagcaguu -continued

```
gggacggccagcuggaggucugcgugguagagggaacuccagagacuguggaucccaag
acugaacggcugcuucugcccacucuuugggauguuucuucuuaaggaagcugaaaaacg
uuauugauuuccaugaccaguuucugagaugaggguuagagguccccucauccuucccug
agacgcc.
```

$N_V$=7.6

EXAMPLE 19

Mα-UTR+4 AUG

```
aguuucAUgcccAUgaccaUgcaucccgagcaccgcgccccgacggaUgucucuuugucc   [SEQ ID NO:45]
gcgccucucccacauacuagaaaucucucccuuucuugagguugggaugaagaagcaguu
gggacggccagcuggaggucugcgugguagagggaacuccagagacuguggaucccaag
acugaacggcugcuucugcccacucuuugggauguuucuucuuaaggaagcugaaaaacg
uuauugauuuccaugaccaguuucugagaugaggguuagagguccccucauccuucccug
agacgcc.
```

$N_V$=8.6

EXAMPLE 20

Mα-UTR+5 AUG

```
aguuucAUgcccAUgaccaUgcaucccgagcaccgcgccccgacggaUgucucuAugucc   [SEQ ID NO:46]
gcgccucucccacauacuagaaaucucucccuuucuugagguugggaugaagaagcaguu
gggacggccagcuggaggucugcgugguagagggaacuccagagacuguggaucccaag
acugaacggcugcuucugcccacucuuugggauguuucuucuuaaggaagcugaaaaacg
uuauugauuuccaugaccaguuucugagaugaggguuagagguccccucauccuucccug
agacgcc.
```

$N_V$=9.6

EXAMPLE 21

Mβ-UTR+1 AUG

```
aguuccagccAuggaccacgcaucccgagcaccgcgccccgacggaggucucuuugucc   [SEQ ID NO:47]
gcgccucucccacauacuagaaaucucucccuuucuugagguugggaugaagaagcaguu
gggacggccagcuggaggucugcgugguagagggaacuccaggucccucauccuucccu
gagacgcc.
```

$N_V$=2.3

EXAMPLE 22

Mβ-UTR+2 AUG aguuuccagccAuggaccacgcaucccgagcaccgcgccccgaUggaggucucuuugucc    [SEQ ID NO:48]
gcgccucucccacauacuagaaaucucucccuuucuugagguugggaugaagaagcaguu
gggacggccagcuggaggucugcgugguagagggaacuccaggucccucauccuucccu
gagacgcc.

$N_V=3.3$

EXAMPLE 23

Mβ UTR+3 AUG aguuuccagccAuggaccacgcaucccgagcaccgcgccccgaUggaggucucuuugucc    [SEQ ID NO:49]
gcgccucucccacauacuagaaaucucucccuuucuugagguugggaugaagaagcaguu
gggacggccagcuggaggucugcgugguagagggaacuccaggucccucauccuuccAu
gagacgcc.

$N_V=4.3$

EXAMPLE 24

Mγ UTR+1 AUG aguuuccagccAuggaccacgcaucccgagcaccgcgccccgacggagguccccucaucc    [SEQ ID NO:50]
uucccugagacgcc.

$N_V=1$

EXAMPLE 25

Mγ UTR+2 AUG aguuuccagccAuggaccaUgcaucccgagcaccgcgccccgacggagguccccucaucc    [SEQ ID NO:51]
uucccugagacgcc.

$N_V=2$

EXAMPLE 26

Mγ UTR+3 AUG aguuuccagccAuggaccaUgcaucccgagcaccgcgccccgaUggagguccccucaucc    [SEQ ID NO:52]
uucccugagacgcc.

$N_V=3$

EXAMPLE 27

Hβ UTR+1 AUG agacuccagccAuggaccgcgcaucccgagcccagcgcccagacagagucuguguaucuc  [SEQ ID NO:53]
ugucucagggaaccgugggucuuugucuccgccucucccauauauuagaaauaucuuacu
uucaugcgguuaaguugaagaggcuggagggauggcuagcuggaugucugcguuguagag
agguaaccccagugucccacacccuccucugagacgcc.

$N_V$=4.9

EXAMPLE 28

Hβ UTR+2 AUG agacuccagccAuggaccgcgcauGccgagcccagcgcccagacagagucuguguaucuc  [SEQ ID NO:54]
ugucucagggaaccgugggucuuugucuccgccucucccauauauuagaaauaucuuacu
uucaugcgguuaaguugaagaggcuggagggauggcuagcuggaugucugcguuguagag
agguaaccccagugucccacacccuccucugagacgcc.

$N_V$=5.9

EXAMPLE 29

Hβ UTR+3 AUG agacuccagccAuggaccgcgcauGccgagcccagcgcccagacagagucuguguauGuc  [SEQ ID NO:55]
ugucucagggaaccgugggucuuugucuccgccucucccauauauuagaaauaucuuacu
uucaugcgguuaaguugaagaggcuggagggauggcuagcuggaugucugcguuguagag
agguaaccccagugucccacacccuccucugagacgcc.

$N_V$=6.9

EXAMPLE 30

Hγ UTR+1 AUG agacuccagccAuggaccgcgcaucccgagcccagcgcccagacagagugucccacacc  [SEQ ID NO:56]
cuccucugagacgcc.

$N_V$=1.3

EXAMPLE 31

Hγ UTR+2 AUG agacuccagccAuggaccgcgcauGccgagcccagcgcccagacagagugucccacacc  [SEQ ID NO:57]
cuccucugagacgcc.

$N_V=2.3$

EXAMPLE 32

Hγ UTR+3 AUG agacuccagccAuggaccgcgcauGccgagcccagcgcccagacagagugucccacacc  [SEQ ID NO:58]
cuccucugagaUgcc.

$N_V=3.3$

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Primer sequences 1

| Name | Location[a] | Nucleotide Sequence | |
|---|---|---|---|
| mGliF1 | exon 1, mouse | agtttccagccctggaccacg | [SEQ ID NO:12] |
| mGliR2 | exon 2, mouse | ggcgtctcagggaaggatgag | [SEQ ID NO:13] |
| hGliF1 | exon 1, human | agactccagccctggaccgcg | [SEQ ID NO:14] |
| hGliR2 | exon 2, human | ggcgtctcagaggagggtgtg | [SEQ ID NO:15] |
| RACE1 | exon 4, mouse | gaggtgggaatcctaag | [SEQ ID NO:16] |
| RACE2 | exon 2/3, mouse | ccagaaagtccttctgttcccatgctgg | [SEQ ID NO:17] |
| mGliF1a | exon 1a, mouse | ctctccctttcttgaggttgg | [SEQ ID NO:18] |

[a]Exons are numbered according to FIGS. 1B and 4B

TABLE 2

Primer sequences 2

| Names | Nucleotide Sequence[a][b] | |
|---|---|---|
| mGliF1$^{Nhe}$ | gctagcagtttccagccctggaccacg | [SEQ ID NO:29] |
| mGliR2$^{Age}$ | accggtggcgtctcagggaaggatgag | [SEQ ID NO:30] |
| mGliF1$^{Bam}$ | ggatccagtttccagccctggaccacg | [SEQ ID NO:27] |
| mGliR2$^{Bgl}$ | agatctggcgtctcagggaaggatgag | [SEQ ID NO:28] |
| mGliMF1 | tcttgaggttgg<u>t</u>tgaagaagcagtt | [SEQ ID NO:19] |
| mGliMR1 | aactgcttcttca<u>a</u>cccaacctcaaga | [SEQ ID NO:23] |
| mGliMF2 | cccactctttggg<u>t</u>tgtttcttcttaa | [SEQ ID NO:20] |
| mGliMR2 | ttaagaagaaaca<u>a</u>cccaaagagtggg | [SEQ ID NO:24] |
| mGliMF3 | gttattgatttcc<u>t</u>tgaccagtttctg | [SEQ ID NO:21] |
| mGliMR3 | cagaaactggtca<u>a</u>ggaaatcaataac | [SEQ ID NO:25] |
| mGliMF4 | accagtttctgag<u>t</u>tgagggttagagg | [SEQ ID NO:22] |
| mGliMR4 | cctctaaccctca<u>a</u>ctcagaaactggt | [SEQ ID NO:26] |

[a]Primers mGliF1$^{Nhe}$, mGliR2$^{Age}$ and mGliF1$^{Bam}$, mGliR2$^{Bgl}$ are identical to mGliF1 and mGliR2 (Table 1) but include restriction sites for NheI, AgeI, BamHI and BglII respectively (shown in bold).
[b]The point mutations (A→T) introduced by primers mGliMF1-4 SEQ ID NOS:19-22] and mGliMR1-4 [SEQ ID NOS:23-26 are shown underlined.

BIBLIOGRAPHY

1. Pain, V. M. (1986) *Biochem. J.* 235: 625–637.
2. Modave, K. (1985) *Ann. Rev. Biochem.* 54: 1109–1149.
3. Kozak, M. (1986) *Cell.* 44: 283–292.
4. Sonenberg, N. (1990) *Curr. Top. Micro. and Imm.* 161: 23–47.
5. Carrington, J. C. and Freed, D. D. (1990) *J. of Vir.* 64: 1590–1597.
6. Jackson et al. (1990) *TIBS* 15: 477–483.
7. Kinzler et al. (1987) *Science* 236: 70–73.
8. Roberts et al. (1989) *Cancer Res.* 49: 5407–5413.
9. Stein et al. (1999) *Cancer Res.* 59: 1890–1895.
10. Ingham, P. W. (1998) *EMBO J.* 17:3505–3511.
11. Johnson, R. L. and Scoff, M. P. (1998) *Curr. Opin. Genet. Dev.* 8: 450–456.
12. Ruiz I Altaba, A. (1999) *Nature Cell Biol.* 1: 147–148.
13. Kinzler et al. (1988) *Nature* 332: 371–374.
14. Ruppert et al. (1988) *Mol. Cell. Biol.* 8: 3104–3113.
15. Walterhouse et al. (1993) *Dev. Dyn.* 196: 91–102.
16. Hui et al. (1994) *Dev. Biol.* 162: 402–413.
17. Marigo et al. (1996) *Dev. Biol.* 180: 273–283.
18. Lee et al. (1997) *Development* 124: 2537–2552.
19. St-Jacques et al. (1998) *Curr. Biol.* 8: 1058–1068.
20. Chiang et al. (1999) *Dev. Biol.* 205: 1–9.
21. Gailani et al. (1996) *Nat. Genet.* 14: 78–81.
22. Hahn et al. (1996) *Cell* 85: 841–851.
23. Johnson et al. (1996) *Science* 272: 1668–1671.
24. Fan et al. (1997) *Nat. Med.* 3: 788–792.
25. Oro et al. (1997) *Science* 276: 817–821.
26. Xie et al. (1998) *Nature* 391 90–92.
27. Dahmane et al. (1997) *Nature* 389: 876–881.
28. Ruppert et al. (1991) *Mol. Cell. Biol,* 11: 1724–1728.
29. Reifenberger et al. (1998) *Cancer Res.* 58: 1798–1803.
30. Ghali, et al. (1999) *Invest. Dermatol* 113: 595–599.
31. Motoyama, et al. (1998) *Nat. Genet.* 20: 54–57.
32. Dai, et al. (1999) *J. Biol. Chem.* 274: 8143–8152.
33. Ruiz I Altaba, A. (1999) *Development* 126: 3205–3216.
34. Sasaki, et al. (1999) *Development* 126: 3915–3924.
35. Altschul et al. (1997) *Nucl. Acids Res.* 25:3389.
36. Ausubel et al., •Current Protocols in Molecular Biology• John Wiley & Sons Inc, 1994–1998, Chapter 15.
37. Bonner and Laskey (1974) *Eur. J. Biochem.* 46: 83.
38. Marmur and Doty (1962) *J. Mol. Biol.* 5: 109.
39. Boukamp, et al. (1988) *L. Cell. Biol.* 106: 761–771.
40. Gluzman, Y. (1981) *Cell* 23: 175–182.
41. Ferrani, M. (1962) *Virology* 16: 147–151.
42. Liu, et al. (1998) *Gene* 209: 1–11.
43. Zuker, M. (1989) *Science* 244: 48–52.
44. Heyden, et al. (1994) *Differentiation* 57: 187–193.
45. Lazo et al. (1991) *Biotechnology* 9: 963–967.
46. Janssen and Gardner, (1989) *Plant Mol. Biol.* 14: 61–72.
47. Hood et al. (1986) *J. Bacterol.* 168:1291–1301.
48. Hoekema et al. (1983) *Nature* 303: 179–180.
49. Konez and Schell, (1986) *Mol. Gen. Genet.* 204: 383–396.
50. Potrykus et al. (1985) *Mol. Gen. Genet.* 199: 183.
51. Hinchee et al. (1988) *Biotech.* 6: 915.
52. Stalker et al. (1988) *Science* 242: 419.
53. Thillet et al. (1988) *J. Biol. Chem.* 263: 12500.
54. Prasher et al. (1985) *Biochem. Biophys. Res. Comm.* 126: 1259.
55. Niedz et al. (1995) *Plant Cell Reports* 14: 403.
56. Ow et al. (1986) *Science* 234: 856.
57. Sutcliffe (1978) *Proc. Natl. Acad. Sci. USA* 75: 3737.
58. Dellaporta et al. (1988) In: *Chromosome Structure and Function* pp 263–282.
59. Ikuta et al. (1990) *Biotech* 8: 241.
60. Katz et. al. (1983) *J. Gen. Microbiol:* 129: 2703.
61. Zukowsky et al. (1983) *Proc. Natl. Acad. Sci. USA* 80: 1101.
62. Sambrook et al. (1989) Molecular Cloning: A Laboratory Manual. Cold Spring Harbor, N.Y., USA.

---

What is claimed is:

1. A method for modulating the expression of a genetic sequence wherein said sequence comprises an open reading frame (ORF) having an RTG or RUG wherein R is A or G corresponding to an authentic translation initiation site of said ORF and a nucleotide sequence 5' of said authentic translation initiation site, said method comprising
   a) introducing one or more ATG triplets in said nucleotide sequence 5' of said authentic translation initiation site; and
   b) introducing one or more termination signals in at least one of said nucleotide sequence 5' of said authentic translation initiation site or the nucleotide sequence downstream of the authentic translation initiation site to create a pseudo-ORF;

such that upon expression of said genetic sequence, there is a decrease in the level of expression.

2. A method for facilitating decreased or reduced expression of a genetic sequence wherein said sequence comprises an ORF having an RTG or RUG where R is A or G corresponding to an authentic translation initiation site of said ORF and a nucleotide sequence 5' of said authentic translation initiation site, said method comprising
   a) introducing one or more ATG triplets in said nucleotide sequence 5' of said authentic translation initiation site; and
   b) introducing one or more termination signals in at least one of said nucleotide sequence 5' of said authentic translation initiation site or the nucleotide sequence downstream of the authentic translation initiation site to create a pseudo-ORF;

such that upon expression of said genetic sequence there is a decrease in the level of expression relative to expression of the genetic sequence in the absence of introducing any ATG triplets.

3. A method for modulating the expression of a genetic sequence wherein said sequence comprises an ORF having an RTG or RUG corresponding to an authentic translation initiation site and a nucleotide sequence 5' of said authentic translation start site comprising the sequence:

$$\{n_1 n_2 \ldots n_a\}_m [x_1 x_2 x_3]_n \{n_1^I n_2^I \ldots n^{bI}\}_o [y_1^I y_2^I y_3^I]$$
$$\{x_1^I x_2^I x_3^I\}_p [n_1^{II} n_2^{II} \ldots n^{cII}]_q \{y_1^{II} y_2^{II} y_3^{II}\}$$
$$[x_1^{II} x_2^{II} x_3^{II}]_r \{n_1^{III} n_2^{III} \ldots n_d^{III}\}_s [y_1^{III} y_2^{III} y_3^{III}]$$
$$RT/UG [z_1 z_2 \ldots z_n]_t$$

wherein:

RT/UG is the authentic translation initiation site and R is A or G;

n, $n^I$, $n^{II}$ and $n^{III}$ are nucleotides selected from A, T or U, C or G or I;

$\{n_1 n_2 \ldots n_a\}_m$, $\{n_1^I n_2^I \ldots n_b^I\}_o$, $\{n_1^{II} n_2^{II} \ldots n_c^{II}\}_q$ and $\{n_1^{III} n_2^{III} \ldots n_d^{III}\}_s$ represent nucleotide sequences of a, b, c or d nucleotides in length and where each of n, $n^I$, $n^{II}$ and $n^{III}$ may be the same or different and its position is indicated by the subscript numeral $_1, _2, \ldots$;

$[z_1 z_2 \ldots z_n]$ represents a translation termination signal within an authentic ORF but not in the same reading frame as said authentic ORF;

each of m, n, o, p, q, r or s may be the same or different and each is 0 or 1 or if there is a repeat or multiple repeats, from about 2 or about 10;

t is 0,1 or >1;

each of $[x_1 x_2 x_3]_n$, $[x_1^I x_2^I x_3^I]_p$ and $[x_1^{II} x_2^{II} x_3^{II}]_r$ is selected from the triplet RTG, RUG, RYG, $RTY^I$, $RY^{II}G$, $RUY^{III}$, ATG, GTG, AUG and GUG where R is A or G, and each of Y, $Y^I$, $Y^{II}$ and $Y^{III}$ may be the same or different and each is a nucleotide with the proviso that Y is not T, $Y^I$ is not G, $Y^{II}$ is not U and $Y^{III}$ is not G;

each of $[y_1^I y_2^I y_3^I]$, $[y_1^{II} y_2^{II} y_3^{II}]$ and $[y_1^{III} y_2^{III} y_3^{III}]$ represents a translation termination signal; and said method comprising altering the nucleotide triplets $[x_1 x_2 x_3]_n$, $[x_1^I x_2^I x_3^I]_p$ and/or $[x_1^{II} x_2^{II} x_3^{II}]_r$ to introduce an ATG to thereby decrease the level of expression of said genetic sequence.

4. The method of claim 3 wherein the genetic sequence is DNA.

5. The method of claim 3 or 4 wherein the nucleotide sequence 5' of the authentic translation initiation site is:

$n_x n_{x+i} \ldots n_{x+z}$ wherein:

$n_x$ is the first nucleotide in a leader sequence;

x is 1 or >1 (e.g. 100, 1000, 10,000 or greater);

$_i$ is 1;

$_z$ is an integer from 1 to 10;

$n_{x+z}$ is the last nucleotide of the 5' leader sequence prior to the translation initiation site;

wherein each n may be the same or different and each is A, C, G, U or T and wherein a numerical value ($N_V$) is assigned to a genetic element such that if:

$n_{x+i}$=n, as defined above;
$n_{x+i+1}$=A;
$n_{x+i+2}$=T or U; and
$n_{x+i+3}$=G then the $N_V$ is 1;

when $n_{x+i}$=n, as defined above;
$n_{x+i+1}$=G;
$n_{x+i+2}$=T or U; and
$n_{x+i+3}$=G then the $N_V$ is 0.3;

and when:

$n_{x+i}$=n as defined above;
$n_{x+i+1}$=C or G;
$n_{x+i+2}$=T or C or G; and
$n_{x+i+3}$=A, T or C then the $N_V$ is 0;

such that the level of expression ($E_L$) of a nucleotide sequence operably linked at its 5' end to $n_x n_{x+1} \ldots n_{x+z}$ is inversely functionally associated (*) to the sum of $N_V$ determined from the nucleotide sequence $n_x n_{x+1} \ldots n_{x+z}$ such that $$E_L * \frac{1}{\sum N_V}.$$

6. The method of claim 5 wherein the nucleotide sequence 5' of the authentic translation initiation site is a GLI1 gene leader sequence, or fragment thereof.

7. The method of claim 6 wherein the GLI1 gene leader sequence comprises the nucleotide sequence set forth in SEQ ID NO:1 or a nucleotide sequence having at least 60% similarity thereto or a nucleotide sequence capable of hybridizing to SEQ ID NO:1 or its complementary form under stringency conditions comprising 2×SSC buffer, 0.15% w/v SDS at 42° C.

8. The method of claim 6 wherein the GLI1 gene leader sequence comprises the nucleotide sequence set forth in SEQ ID NO:1 or a nucleotide sequence having at least 60% similarity thereto or a nucleotide sequence capable of hybridizing to SEQ ID NO:2 or its complementary form under stringency conditions comprising 2×SSC buffer, 0.15% w/v SDS at 42° C.

9. The method of claim 6 wherein the GLI1 gene leader sequence comprises the nucleotide sequence set forth in SEQ ID NO:1 or a nucleotide sequence having at least 60% similarity thereto or a nucleotide sequence capable of hybridizing to SEQ ID NO:3 or its complementary form under stringency conditions comprising 2×SSC buffer, 0.15% w/v SDS at 42° C.

10. The method of claim 6 wherein the GLI1 gene leader sequence comprises the nucleotide sequence set forth in SEQ ID NO:1 or a nucleotide sequence having at least 60% similarity thereto or a nucleotide sequence capable of hybridizing to SEQ ID NO:4 or its complementary form under stringency conditions comprising 2×SSC buffer, 0.15% w/v SDS at 42° C.

11. The method of claim 6 wherein the GLI1 gene leader sequence comprises the nucleotide sequence set forth in SEQ ID NO:1 or a nucleotide sequence having at least 60% similarity thereto or a nucleotide sequence capable of hybridizing to SEQ ID NO:5 or its complementary form under stringency conditions comprising 2×SSC buffer, 0.15% w/v SDS at 42° C.

12. A method for modulating the expression of a genetic sequence in a plant cell wherein said sequence comprises an ORF having an RTG or RUG wherein R is A or G corresponding to an authentic translation initiation site of said ORF and a nucleotide sequence 5' of said authentic translation initiation site, said method comprising
   a) introducing one or more ATG triplets in said nucleotide sequence 5' of said authentic translation initiation site; and
   b) introducing one or more termination signals in at least one of said nucleotide sequence 5' of said authentic translation initiation site or the nucleotide sequence downstream of the authentic translation initiation site to create a pseudo-ORF;
such that upon expression of said genetic sequence, there is a decrease in the level of expression.

13. The method of claim 12 wherein the plant cell is from a cereal crop, a vegetable plant, a fruiting plant, a flowering plant or cotton or tobacco.

14. The method of claim 13 wherein the plant cell is from cotton.

15. The method of claim 13 wherein the plant cell is from a cereal crop.

16. The method of claim 13 wherein the target sequence whose expression is modulated confers resistance to a herbicide.

17. The method of claim 13 wherein the target sequence whose expression is modulated confers resistance to a pesticide.

18. A method for modulating the expression of a genetic sequence in an animal cell wherein said sequence comprises an ORF having an RTG or RUG wherein R is A or G corresponding to an authentic translation initiation site of said ORF and a nucleotide sequence 5' of said authentic translation initiation site, said method comprising
   a) introducing one or more ATG triplets in said nucleotide sequence 5' of said authentic translation initiation site; and
   b) introducing one or more termination signals in at least one of said nucleotide sequence 5' of said authentic translation initiation site or the nucleotide sequence downstream of the authentic translation initiation site to create a pseudo-ORF;
such that upon expression of said genetic sequence, there is a decrease in the level of expression.

19. The method of claim 18 wherein the animal cell is a mammalian cell.

20. The method of claim 18 wherein the animal cell is a human cell.

21. A method for modulating the expression of a genetic sequence wherein said sequence comprises an ORF having an RTG or RUG wherein R is A or G corresponding to an authentic translation initiation site of said ORF and a nucleotide sequence 5' of said authentic translation initiation site, said method comprising introducing one or more ATG triplets in said nucleotide sequence 5' of said authentic translation initiation site such that upon expression of said genetic sequence, there is a decrease in the level of expression, and wherein the nucleotide sequence 5' of the authentic translation start site comprises the sequence:

$$\{n_1 n_2 \ldots n_a\}_m [x_1 x_2 x_3]_n \{n_1^I n_2^I \ldots n_b^I\}_o [y_1^I y_2^I y_3^I]$$
$$\{x_1^I x_2^I x_3^I\}_p [n_1^{II} n_2^{II} \ldots n^{II}]_q \{y_1^{II} y_2^{II} y_3^{II}\}$$
$$[x_1^{II} x_2^{II} x_3^{II}]_r \{n_1^{III} n_2^{III} \ldots n_d^{III}\}_s [y_1^{III} y_2^{III} y_3^{III}]$$
$$RT/UG[z_1 z_2 \ldots z_n]_t$$

wherein:
   RT/UG is the authentic translation initiation site and R is A or G;
   n, $n^I$, $n^{II}$ and $n^{III}$ are nucleotides selected from A, T or U, C or G or I;
   $\{n_1 n_2 \ldots n_a\}_m$, $\{n_1^I n_2^I \ldots n_b^I\}_o$, $\{n_1^{II} n_2^{II} \ldots n_c^{II}\}_q$ and $\{n_1^{III} n_2^{III} \ldots n_d^{III}\}_s$ represent nucleotide sequences of a, b, c or d nucleotides in length and where each of n, $n^I$, $n^{II}$ and $n^{III}$ may be the same or different and its position is indicated by the subscript numeral $_1, _2, \ldots$;
   $[z_1 z_2 \ldots z_n]$ represents a translation termination signal within an authentic ORF but not in the same reading frame as said authentic ORF;
   each of m, n, o, p, q, r or s may be the same or different and each is 0 or 1 or if there is a repeat or multiple repeats, from about 2 or about 10;
   t is 0,1 or >1;
   each of $[x_1 x_2 x_3]_n$, $[x_1^I x_2^I x_3^I]_p$ and $[x_1^{II} x_2^{II} x_3^{II}]_r$ is selected from the triplet RTG, RUG, RYG, $RTY^I$, $RY^{II}G$, $RUY^{II}$, ATG, GTG, AUG and GUG where R is A or G, and each of Y, $Y^I$, $Y^{II}$ and $Y^{III}$ may be the same or different and each is a nucleotide with the proviso that Y is not T, $Y^I$ is not G, $Y^{II}$ is not U and $Y^{III}$ is not G;

each of $[y_1^I y_2^I y_3^I]$, $[y_1^{II} y_2^{II} y_3^{II}]$ and $[y_1^{III} y_2^{III} y_3^{III}]$ represents a translation termination signal; and said method comprising altering the nucleotide triplets $[x_1 x_2 x_3]_n$, $[x_1^I x_2^I x_3^I]_p$ and/or $[x_1^{II} x_2^{II} x_3^{II}]_r$ to introduce an ATG and thereby respectively decrease the level of expression of said genetic sequence.

22. A method for facilitating decreased or reduced expression of a genetic sequence wherein said sequence comprises an ORF having an RTG or RUG where R is A or G corresponding to an authentic translation initiation site of said ORF and a nucleotide sequence 5' of said authentic translation initiation site, said method comprising introducing or creating one or more ATG triplets in said nucleotide sequence 5' of said authentic translation initiation site such that upon expression of said genetic sequence there is a decrease in the level of expression relative to expression of the genetic sequence in the absence of introducing any ATG triplets, and wherein the nucleotide sequence 5' of the authentic translation initiation site comprises the sequence:

$$\{n_1 n_2 \ldots n_a\}_m [x_1 x_2 x_3]_n \{n_1^I n_2^I \ldots n_b^I\}_o [y_1^I y_2^I y_3^I]$$
$$\{x_1^I x_2^I x_3^I\}_p [n_1^{II} n_2^{II} \ldots n_c^{II}]_q \{y_1^{II} y_2^{II} y_3^{II}\}$$
$$[x_1^{II} x_2^{II} x_3^{II}]_r \{n_1^{III} n_2^{III} \ldots n_d^{III}\}_s [y_1^{III} y_2^{III} y_3^{III}]$$
$$RT/UG[z_1 z_2 \ldots z_n]_t$$

wherein:

RT/UG is the authentic translation initiation site and R is A or G;

n, $n^I$, $n^{II}$ and $n^{III}$ are nucleotides selected from A, T or U, C or G or I;

$\{n_1 n_2 \ldots n_a\}_m$, $\{n_1^I n_2^I \ldots n_b^I\}_o$, $\{n_1^{II} n_2^{II} \ldots n_c^{II}\}_q$ and $\{n_1^{III} n_2^{III} \ldots n_d^{III}\}_s$ represent nucleotide sequences of a, b, c or d nucleotides in length and where each of n, $n^I$, $n^{II}$ and $n^{III}$ may be the same or different and its position is indicated by the subscript numeral $_1, _2, \ldots$;

$[z_1 z_2 \ldots z_n]$ represents a translation termination signal within an authentic ORF but not in the same reading frame as said authentic ORF;

each of m, n, o, p, q, r or s may be the same or different and each is 0 or 1 or if there is a repeat or multiple repeats, from about 2 or about 10;

t is 0,1 or >1;

each of $[x_1 x_2 x_3]_n$, $[x_1^I x_2^I x_3^I]_p$ and $[x_1^{II} x_2^{II} x_3^{II}]_r$ is selected from the triplet RTG, RUG, RYG, $RTY^I$, $RY^{II}G$, $RUY^{III}$, ATG, GTG, AUG and GUG where R is A or G, and each of Y, $Y^I$, $Y^{II}$ and $Y^{III}$ may be the same or different and each is a nucleotide with the proviso that Y is not T, $Y^I$ is not G, $Y^{II}$ is not U and $Y^{III}$ is not G;

each of $[y_1^I y_2^I y_3^I]$, $[y_1^{II} y_2^{II} y_3^{II}]$ and $[y_1^{III} y_2^{III} y_3^{III}]$ represents a translation termination signal; and said method comprising altering the nucleotide triplets $[x_1 x_2 x_3]_n$, $[x_1^I x_2^I x_3^I]_p$ and/or $[x_1^{II} x_2^{II} x_3^{II}]_r$ to introduce an ATG to thereby decrease the level of expression of said genetic sequence.

* * * * *

SEQUENCE LISTING

```
<160> NUMBER OF SEQ ID NOS: 60

<210> SEQ ID NO 1
<211> LENGTH: 307
<212> TYPE: RNA
<213> ORGANISM: mouse

<400> SEQUENCE: 1
aguuuccagc ccuggaccac gcaucccgag caccgcgccc cgacggaggu cucuuugucc      60
      gcgccucucc cacauacuag aaaucucucc cuuucuugag guugggauga agaagcaguu     120
      gggacggcca gcuggagguc ugcgugguag agggaacucc agagacugug gauccccaag     180
      acugaacggc ugcuucugcc cacucuuugg gauguuucuu cuuaaggaag cugaaaaacg     240
      uuauugauuu ccaugaccag uuucugagau gaggguuaga ggucccucua uccuucccug     300
      agacgcc                                                              307

<210> SEQ ID NO 2
<211> LENGTH: 188
<212> TYPE: RNA
<213> ORGANISM: mouse

<400> SEQUENCE: 2
aguuuccagc ccuggaccac gcaucccgag caccgcgccc cgacggaggu cucuuugucc      60
      gcgccucucc cacauacuag aaaucucucc cuuucuugag guugggauga agaagcaguu     120
      gggacggcca gcuggagguc ugcgugguag agggaacucc aggucccuc auccuucccu     180
      gagacgcc                                                             188
```

```
<210> SEQ ID NO 3
<211> LENGTH: 74
<212> TYPE: RNA
<213> ORGANISM: mouse

<400> SEQUENCE: 3
aguuuccagc ccuggaccac gcaucccgag caccgcgccc cgacggaggu ccccucaucc    60
     uucccugaga cgcc                                                      74

<210> SEQ ID NO 4
<211> LENGTH: 219
<212> TYPE: RNA
<213> ORGANISM: human

<400> SEQUENCE: 4
agacuccagc ccuggaccgc gcaucccgag cccagcgccc agacagaguc uguguaucuc    60
     ugucucaggg aaccgugggu cuuugucucc gccucuccca uauauuagaa auaucuuacu   120
     uucaugcggu uaaguugaag aggcuggagg gauggcuagc uggaugucug cguuguagag   180
     agguaaccec agugucccca cacccuccuc ugagacgcc                          219

<210> SEQ ID NO 5
<211> LENGTH: 75
<212> TYPE: RNA
<213> ORGANISM: human

<400> SEQUENCE: 5
agacuccagc ccuggaccgc gcaucccgag cccagcgccc agacagagug uccccacacc    60
     cuccucugag acgcc                                                     75

<210> SEQ ID NO 6
<211> LENGTH: 8
<212> TYPE: DNA
<213> ORGANISM: artificial sequence
<220> FEATURE:
<223> OTHER INFORMATION: Description of Artificial Sequence:This sequence represents
      a Kozac sequence.
<221> NAME/KEY: misc_feature
<222> LOCATION: (2)..(2)
<223> OTHER INFORMATION: n = any nucleotide
<221> NAME/KEY: misc_feature
<222> LOCATION: (8)..(8)
<223> OTHER INFORMATION: n = any nucleotide

<400> SEQUENCE: 6 rnccrwgn                                                              8

<210> SEQ ID NO 7
<211> LENGTH: 10
<212> TYPE: DNA
```

```
<213> ORGANISM: artificial sequence
<220> FEATURE:
<223> OTHER INFORMATION: Description of Artificial Sequence:This sequence represents
      a strong Kozac sequence.

<400> SEQUENCE: 7 gccrccrwgg                                                              10

<210> SEQ ID NO 8
<211> LENGTH: 10
<212> TYPE: DNA
<213> ORGANISM: artificial sequence
<220> FEATURE:
<223> OTHER INFORMATION: Description of Artificial Sequence:This sequence represents
      a weak Kozac sequence.
<221> NAME/KEY: misc_feature
<222> LOCATION: (10)..(10)
<223> OTHER INFORMATION: n = any nucleotide

<400> SEQUENCE: 8 atttccrwgn                                                              10

<210> SEQ ID NO 9
<211> LENGTH: 10
<212> TYPE: DNA
<213> ORGANISM: artificial sequence
<220> FEATURE:
<223> OTHER INFORMATION: Description of Artificial Sequence:This sequence represents
      a 5' leader sequence.

<400> SEQUENCE: 9
atttccttga                                                              10

<210> SEQ ID NO 10
<211> LENGTH: 10
<212> TYPE: DNA
<213> ORGANISM: artificial sequence
<220> FEATURE:
<223> OTHER INFORMATION: Description of Artificial Sequence:This sequence represents
      a 5' leader sequence with a weak Kozac sequence.

<400> SEQUENCE: 10
atttccatga                                                              10

<210> SEQ ID NO 11
<211> LENGTH: 11
<212> TYPE: DNA
<213> ORGANISM: artificial sequence
<220> FEATURE:
<223> OTHER INFORMATION: Description of Artificial Sequence:This sequence represents
      a 5' leader sequence with a strong Kozac sequence.

<400> SEQUENCE: 11
gccagccatg a                                                            11

<210> SEQ ID NO 12
<211> LENGTH: 21
<212> TYPE: DNA
<213> ORGANISM: primer

<400> SEQUENCE: 12
agtttccagc cctggaccac g                                                 21

<210> SEQ ID NO 13
<211> LENGTH: 21
<212> TYPE: DNA
<213> ORGANISM: primer
```

```
<400> SEQUENCE: 13
ggcgtctcag ggaaggatga g                                        21

<210> SEQ ID NO 14
<211> LENGTH: 27
<212> TYPE: DNA
<213> ORGANISM: primer

<400> SEQUENCE: 14
gctagcagtt tccagccctg gaccacg                                   27

<210> SEQ ID NO 15
<211> LENGTH: 27
<212> TYPE: DNA
<213> ORGANISM: primer

<400> SEQUENCE: 15
accggtggcg tctcagggaa ggatgag                                   27

<210> SEQ ID NO 16
<211> LENGTH: 17
<212> TYPE: DNA
<213> ORGANISM: primer

<400> SEQUENCE: 16
gaggtgggaa tcctaag                                              17

<210> SEQ ID NO 17
<211> LENGTH: 28
<212> TYPE: DNA
<213> ORGANISM: primer

<400> SEQUENCE: 17
ccagaaagtc cttctgttcc catgctgg                                  28

<210> SEQ ID NO 18
<211> LENGTH: 21
<212> TYPE: DNA
<213> ORGANISM: primer

<400> SEQUENCE: 18
ctctcccttt cttgaggttg g                                         21

<210> SEQ ID NO 19
<211> LENGTH: 27
<212> TYPE: DNA
<213> ORGANISM: primer

<400> SEQUENCE: 19
tcttgaggtt gggttgaaga agcagtt                                   27

<210> SEQ ID NO 20
<211> LENGTH: 27
<212> TYPE: DNA
<213> ORGANISM: primer

<400> SEQUENCE: 20
cccactcttt gggttgtttc ttcttaa                                   27

<210> SEQ ID NO 21
<211> LENGTH: 27
<212> TYPE: DNA
```

<213> ORGANISM: primer

<400> SEQUENCE: 21
gttattgatt tccttgacca gtttctg                    27

<210> SEQ ID NO 22
<211> LENGTH: 27
<212> TYPE: DNA
<213> ORGANISM: primer

<400> SEQUENCE: 22
accagtttct gagttgaggg ttagagg                    27

<210> SEQ ID NO 23
<211> LENGTH: 27
<212> TYPE: DNA
<213> ORGANISM: primer

<400> SEQUENCE: 23
aactgcttct tcaacccaac ctcaaga                    27

<210> SEQ ID NO 24
<211> LENGTH: 27
<212> TYPE: DNA
<213> ORGANISM: primer

<400> SEQUENCE: 24
ttaagaagaa acaacccaaa gagtggg                    27

<210> SEQ ID NO 25
<211> LENGTH: 27
<212> TYPE: DNA
<213> ORGANISM: primer

<400> SEQUENCE: 25
cagaaactgg tcaaggaaat caataac                    27

<210> SEQ ID NO 26
<211> LENGTH: 27
<212> TYPE: DNA
<213> ORGANISM: primer

<400> SEQUENCE: 26
cctctaaccc tcaactcaga aactggt                    27

<210> SEQ ID NO 27
<211> LENGTH: 27
<212> TYPE: DNA
<213> ORGANISM: primer

<400> SEQUENCE: 27
ggatccagtt tccagccctg gaccacg                    27

<210> SEQ ID NO 28
<211> LENGTH: 27
<212> TYPE: DNA
<213> ORGANISM: primer

<400> SEQUENCE: 28
agatctggcg tctcagggaa ggatgag                    27

<210> SEQ ID NO 29
<211> LENGTH: 27

```
<212> TYPE: DNA
<213> ORGANISM: primer

<400> SEQUENCE: 29
gctagcagtt tccagccctg gaccacg                                        27

<210> SEQ ID NO 30
<211> LENGTH: 27
<212> TYPE: DNA
<213> ORGANISM: primer

<400> SEQUENCE: 30
accggtggcg tctcagggaa ggatgag                                        27

<210> SEQ ID NO 31
<211> LENGTH: 21
<212> TYPE: DNA
<213> ORGANISM: primer

<400> SEQUENCE: 31
agactccagc cctggaccgc g                                              21

<210> SEQ ID NO 32
<211> LENGTH: 21
<212> TYPE: DNA
<213> ORGANISM: primer

<400> SEQUENCE: 32
ggcgtctcag aggagggtgt g                                              21

<210> SEQ ID NO 33
<211> LENGTH: 877
<212> TYPE: DNA
<213> ORGANISM: mouse

<400> SEQUENCE: 33
agtttccagc cctggaccac gcatcccgag caccgcgccc cgacggaggt gagagggggg      60
    caggcgggag accacctggg agcgatgggg gagggctgag gagatgctct gacgcctagg     120
    gactcaccct ctcccagaag gagacctggg gctcagaggc aatatggggt tgggagagtt     180
    tggggagagc aattaggaag tttgggtgtt tcttgttttt gctttaattt gtgccttctt     240
    ttctctgcat ccccttcttt tttctgaca atctgtgtct gtcccaggtc tctttgtccg     300
    cgcctctccc acatactaga aatctctccc tttcttgagg ttgggatgaa gaagcagttg     360
    ggacggccag ctggaggtct gcgtggtaga gggaactcca ggtcgcgtct gagcgccgtt     420
    ggaagacgtc agtgtttcta agacgggacc caccgcaaaa gaaggagcg ctcagtgggg     480
    tgggagtagc ggtgtgccag gcaacagaac ccctgagggc cgggctggga ttggactcct     540
    gacctgtggc tgtgacagat gtgcacatgg ggtttagggg caaaggagtg ggtttggact     600
    cggaggagg ctgggtgggt ttcctaacat gtggtgtagg ccgtaaaaaa atccctagga     660
    attctggact tctgagtccc aaagactgtg gcagggccc ccgaggaaaa gtaagagctg     720
    gggaaacctt gttttgaccc tctgacctca agaccaccgg ggcaactgaa gccaggcgcc     780
    gggagacccc tactgggca gaacgggacc actggctact gccagcttgt gtatcccttg     840
    ttgggccccc cgcccaaacc gggatcttgg ggaccga                             877

<210> SEQ ID NO 34
<211> LENGTH: 427
<212> TYPE: DNA
<213> ORGANISM: mouse

<400> SEQUENCE: 34
ttccgtgtgt tccaccatca cacacctcaa agctggccca tggccagaac aagaaatggt      60
    agagggaaaa gaaaaagaa aagcaagtag agagagctca tggcattaaa aatcacctag     120
    gacttgtgtt ggatcagtta gtccctaaca ttcccttgta catacagaga ctgtggatcc     180
    ccaagactga acggctgctt ctgcccactc tttgggatgt ttcttcttaa ggaagctgaa     240
    aaacgttatt gatttccatg accagtttct gagatgaggg ttagaggtac aaggacatg     300
    ctggcgaggg ggggggggg aaatctgtgc ctgaaactgt catttatctt ctctgtttcg     360
    ctccatcttt ataactggca gatctacatt cctttccaca ggtccccctca tccttccctg     420
    agacgcc                                                             427
```

<210> SEQ ID NO 35
<211> LENGTH: 581
<212> TYPE: DNA
<213> ORGANISM: human

<400> SEQUENCE: 35

```
agactccagc cctggaccgc gcatcccgag cccagcgccc agacagaggt gagaaggggg      60
ggcaggcggg ggaccacctg ggagcagtgg gggaggggc ctgaggggat gctcagcttc     120
ttagggactc atcccagacc cggacatag aggcaaaata ggggtgggag agcctgggt      180
gagacattag aaactccaga ttttttcactt gtgtctttct ctgtatcttc ttttcttcc    240
cttttttcct tctgtcagtc tgtgtatctc tgtctcaggg aaccgtgggt ctttgtctcc   300
gcctctccca tatattagaa atatcttact ttcatgcggt taagtttaag aggctggagg   360
gatggctagc tggaggtctg cgttgtagag aggtaacccc aggtgtgtgc ctgcgcgtgg   420
ggtaggaaga tgtcagtgtt tctgaaaggt ggggactgca aaggaggag ctccaagtgg    480
ggtggggacg ggtgtgtggg aggcaacaga gccactaggg gccaccaggc ttgaacctt     540
gacctgtctt gtgacagatg tgccagtgga tgcttgtgct t                      581
```

<210> SEQ ID NO 36
<211> LENGTH: 573
<212> TYPE: DNA
<213> ORGANISM: human

<400> SEQUENCE: 36

```
acccagttcc caagaagatc cccagagtac acagactaca agactgcctc tgcctctctg    60
ggacatcatt tcccttacc cctcccctca ctcagcgagt gatgctttt ttgttttgag    120
acggagtcta gctctgtcac ccaggctgga gtgcagtggc accatctcgg ctcactgaaa   180
cctccgcctc ccaggttcaa gcgattcttc tgcctcagcc ttccgagtag ctgggattac   240
aggcacccgc catcatgact ggctaatttt tgtttttttg tagagacggg ggtttcacca   300
tgttggccag gctggtcttc aactgtcctc aggtgatcct cccgcctcag cctctcaaag   360
cgttggaatt acaggcgtga gccactgtgc ccggctcagt gatgctcttt tcaactcgaa   420
ttccgtggca gatgtcttag aggggtgggg gataccaggg atgttctgcc caggattctg   480
tgcctgagac tgctgtctga cagtctctat ttcctccacc tttatatcca ccttccctt    540
ctgcagtgtc cccacaccct cctctgagac gcc                                573
```

<210> SEQ ID NO 37
<211> LENGTH: 22
<212> TYPE: DNA
<213> ORGANISM: primer

<400> SEQUENCE: 37

```
ttgagctcag ttccagccct gg                                             22
```

<210> SEQ ID NO 38
<211> LENGTH: 20
<212> TYPE: DNA
<213> ORGANISM: primer

<400> SEQUENCE: 38

```
aaccatggcg tctcagggaa                                                20
```

<210> SEQ ID NO 39
<211> LENGTH: 18
<212> TYPE: DNA
<213> ORGANISM: primer

<400> SEQUENCE: 39

```
ggtttcccag tcaccgac                                                  18
```

<210> SEQ ID NO 40
<211> LENGTH: 21
<212> TYPE: DNA
<213> ORGANISM: primer

<400> SEQUENCE: 40

```
acacaggaaa cagctatgac c                                              21
```

<210> SEQ ID NO 41

```
<211> LENGTH: 307
<212> TYPE: RNA
<213> ORGANISM: mouse

<400> SEQUENCE: 41
aguuuccagc ccuggaccac gcaucccgag caccgcgccc cgacggaggu cucuuugucc        60
    gcgccucucc cacauacuag aaaucucucc cuuucuugag guugggauga agaagcaguu       120
    gggacggcca gcuggagguc ugcgugguag agggaacucc agagacugug gaucccaag        180
    acugaacggc ugcuucugcc cacucuuugg gauguuucuu cuuaaggaag cugaaaaacg       240
    uuauugauuu ccaugaccag uuucugagau gaggguuaga ggucccuca uccuucccug        300
    agacgcc                                                                 307

<210> SEQ ID NO 42
<211> LENGTH: 307
<212> TYPE: RNA
<213> ORGANISM: mouse

<400> SEQUENCE: 42
aguuucaugc ccuggaccac gcaucccgag caccgcgccc cgacggaggu cucuuugucc        60
    gcgccucucc cacauacuag aaaucucucc cuuucuugag guugggauga agaagcaguu       120
    gggacggcca gcuggagguc ugcgugguag agggaacucc agagacugug gaucccaag        180
    acugaacggc ugcuucugcc cacucuuugg gauguuucuu cuuaaggaag cugaaaaacg       240
    uuauugauuu ccaugaccag uuucugagau gaggguuaga ggucccuca uccuucccug        300
    agacgcc                                                                 307

<210> SEQ ID NO 43
<211> LENGTH: 307
<212> TYPE: RNA
<213> ORGANISM: mouse

<400> SEQUENCE: 43
aguuucaugc ccaugaccac gcaucccgag caccgcgccc cgacggaggu cucuuugucc        60
    gcgccucucc cacauacuag aaaucucucc cuuucuugag guugggauga agaagcaguu       120
    gggacggcca gcuggagguc ugcgugguag agggaacucc agagacugug gaucccaag        180
    acugaacggc ugcuucugcc cacucuuugg gauguuucuu cuuaaggaag cugaaaaacg       240
    uuauugauuu ccaugaccag uuucugagau gaggguuaga ggucccuca uccuucccug        300
    agacgcc                                                                 307

<210> SEQ ID NO 44
<211> LENGTH: 307
<212> TYPE: RNA
<213> ORGANISM: mouse

<400> SEQUENCE: 44
aguuucaugc ccaugaccau gcaucccgag caccgcgccc cgacggaggu cucuuugucc        60
    gcgccucucc cacauacuag aaaucucucc cuuucuugag guugggauga agaagcaguu       120
    gggacggcca gcuggagguc ugcgugguag agggaacucc agagacugug gaucccaag        180
    acugaacggc ugcuucugcc cacucuuugg gauguuucuu cuuaaggaag cugaaaaacg       240
    uuauugauuu ccaugaccag uuucugagau gaggguuaga ggucccuca uccuucccug        300
    agacgcc                                                                 307

<210> SEQ ID NO 45
<211> LENGTH: 307
<212> TYPE: RNA
<213> ORGANISM: mouse

<400> SEQUENCE: 45
aguuucaugc ccaugaccau gcaucccgag caccgcgccc cgacggaugu cucuuugucc        60
    gcgccucucc cacauacuag aaaucucucc cuuucuugag guugggauga agaagcaguu       120
    gggacggcca gcuggagguc ugcgugguag agggaacucc agagacugug gaucccaag        180
    acugaacggc ugcuucugcc cacucuuugg gauguuucuu cuuaaggaag cugaaaaacg       240
    uuauugauuu ccaugaccag uuucugagau gaggguuaga ggucccuca uccuucccug        300
    agacgcc                                                                 307

<210> SEQ ID NO 46
<211> LENGTH: 307
<212> TYPE: RNA
<213> ORGANISM: mouse
```

```
<400> SEQUENCE: 46
aguuucaugc ccaugaccau gcaucccgag caccgcgccc cgacggaugu cucuaugucc      60
    gcgccucucc cacauacuag aaaucucucc cuuucuugag guugggauga agaagcaguu     120
    gggacggcca gcuggagguc ugcguggua g agggaacucc agagacugug gauccccaag    180
    acugaacggc ugcuucugcc cacucuuugg gauguuucuu cuuaaggaag cugaaaaacg     240
    uuauugauuu ccaugaccag uuucugagau gagggujaga ggucccccuca uccuucccug    300
    agacgcc                                                                307

<210> SEQ ID NO 47
<211> LENGTH: 188
<212> TYPE: RNA
<213> ORGANISM: mouse

<400> SEQUENCE: 47 aguuccagc cauggaccac gcaucccgag caccgcgccc cgacggaggu cucuuugucc       60
    gcgccucucc cacauacuag aaaucucucc cuuucuugag guugggauga agaagcaguu     120
    gggacggcca gcuggagguc ugcguggua g agggaacucc aggucccuc auccuucccu     180
    gagacgcc                                                               188

<210> SEQ ID NO 48
<211> LENGTH: 188
<212> TYPE: RNA
<213> ORGANISM: mouse

<400> SEQUENCE: 48 aguuccagc cauggaccac gcaucccgag caccgcgccc cgauggaggu cucuuugucc       60
    gcgccucucc cacauacuag aaaucucucc cuuucuugag guugggauga agaagcaguu     120
    gggacggcca gcuggagguc ugcguggua g agggaacucc aggucccuc auccuucccu     180
    gagacgcc                                                               188

<210> SEQ ID NO 49
<211> LENGTH: 188
<212> TYPE: RNA
<213> ORGANISM: mouse

<400> SEQUENCE: 49 aguuccagc cauggaccac gcaucccgag caccgcgccc cgauggaggu cucuuugucc       60
    gcgccucucc cacauacuag aaaucucucc cuuucuugag guugggauga agaagcaguu     120
    gggacggcca gcuggagguc ugcguggua g agggaacucc aggucccuc auccuuccau     180
    gagacgcc                                                               188

<210> SEQ ID NO 50
<211> LENGTH: 74
<212> TYPE: RNA
<213> ORGANISM: mouse

<400> SEQUENCE: 50 aguuccagc cauggaccac gcaucccgag caccgcgccc cgacggaggu ccccucaucc       60
    uucccugaga cgcc                                                         74

<210> SEQ ID NO 51
<211> LENGTH: 74
<212> TYPE: RNA
<213> ORGANISM: mouse

<400> SEQUENCE: 51 aguuccagc cauggaccau gcaucccgag caccgcgccc cgacggaggu ccccucaucc       60
    uucccugaga cgcc                                                         74

<210> SEQ ID NO 52
<211> LENGTH: 74
<212> TYPE: RNA
<213> ORGANISM: mouse

<400> SEQUENCE: 52 aguuccagc cauggaccau gcaucccgag caccgcgccc cgauggaggu ccccucaucc       60
```

-continued

```
                uucccugaga cgcc                                              74
```

<210> SEQ ID NO 53
<211> LENGTH: 219
<212> TYPE: RNA
<213> ORGANISM: human

<400> SEQUENCE: 53

```
        agacuccagc cauggaccgc gcaucccgag cccagcgccc agacagaguc uguguaucuc    60
        ugucucaggg aaccgugggu cuuugucucc gccucuccca uauauuagaa auaucuuacu   120
        uucaugcggu uaaguugaag aggcuggagg gauggcuagc uggaugucug cguuguagag   180
        agguaacccc agugucccca caccuccuc ugagacgcc                           219
```

<210> SEQ ID NO 54
<211> LENGTH: 219
<212> TYPE: RNA
<213> ORGANISM: human

<400> SEQUENCE: 54

```
        agacuccagc cauggaccgc gcaugccgag cccagcgccc agacagaguc uguguaucuc    60
        ugucucaggg aaccgugggu cuuugucucc gccucuccca uauauuagaa auaucuuacu   120
        uucaugcggu uaaguugaag aggcuggagg gauggcuagc uggaugucug cguuguagag   180
        agguaacccc agugucccca caccuccuc ugagacgcc                           219
```

<210> SEQ ID NO 55
<211> LENGTH: 219
<212> TYPE: RNA
<213> ORGANISM: human

<400> SEQUENCE: 55

```
        agacuccagc cauggaccgc gcaugccgag cccagcgccc agacagaguc uguguauguc    60
        ugucucaggg aaccgugggu cuuugucucc gccucuccca uauauuagaa auaucuuacu   120
        uucaugcggu uaaguugaag aggcuggagg gauggcuagc uggaugucug cguuguagag   180
        agguaacccc agugucccca caccuccuc ugagacgcc                           219
```

<210> SEQ ID NO 56
<211> LENGTH: 75
<212> TYPE: RNA
<213> ORGANISM: human

<400> SEQUENCE: 56

```
        agacuccagc cauggaccgc gcaucccgag cccagcgccc agacagagug uccccacacc    60
        cuccucugag acgcc                                                     75
```

<210> SEQ ID NO 57
<211> LENGTH: 75
<212> TYPE: RNA
<213> ORGANISM: human

<400> SEQUENCE: 57

```
        agacuccagc cauggaccgc gcaugccgag cccagcgccc agacagagug uccccacacc    60
        cuccucugag acgcc                                                     75
```

<210> SEQ ID NO 58
<211> LENGTH: 75
<212> TYPE: RNA
<213> ORGANISM: human

<400> SEQUENCE: 58

```
        agacuccagc cauggaccgc gcaugccgag cccagcgccc agacagagug uccccacacc    60
        cuccucugag augcc                                                     75
```

<210> SEQ ID NO 59
<211> LENGTH: 3707
<212> TYPE: DNA
<213> ORGANISM: mouse

```
<220> FEATURE:
<221> NAME/KEY: misc_feature
<222> LOCATION: (1762)..(1762)
<223> OTHER INFORMATION: n = any nucleotide
<221> NAME/KEY: misc_feature
<222> LOCATION: (1767)..(1767)
<223> OTHER INFORMATION: n = any nucleotide
<221> NAME/KEY: misc_feature
<222> LOCATION: (1769)..(1769)
<223> OTHER INFORMATION: n = any nucleotide
<221> NAME/KEY: misc_feature
<222> LOCATION: (1812)..(1812)
<223> OTHER INFORMATION: n = any nucleotide
<221> NAME/KEY: misc_feature
<222> LOCATION: (2994)..(2994)
<223> OTHER INFORMATION: n = any nucleotide

<400> SEQUENCE: 59
ggatcctggg ggtcctgggg gtgccataag cccggcaccc cctctctagc ttctatccac      60
ccagctcatc ttctagaacg gtccgaagaa ggatatacga gggaagtgag cgggaagagc     120
cgtagcgtgc ggtggcaaca gcgagaaaaa gttttgcaa aggggaaaaa aaagtttgc      180
gcttctcgcg ggtggtcccg gctcgaggcc cggcgcgtgg cgggcggagg gctgggggcc     240
aggttgggag ggtggggtgg cactgaagct gcgctgcagt ggccctgtga cccccctccc     300
cgccacacac ctccccccc ccccagccca gtttccagcc ctggaccacg catcccgagc     360
accgcgcccc gacggaggtg agaggggggc aggcgggaga ccacctggga gcgatggggg     420
agggctgagg agatgctctg acgcctaggg actcaccctc tcccagaagg agacctgggg     480
ctcagaggca atatgggtt gggagagttt ggggagagca attaggaagt ttgggtgttt     540
tcttgttttg ctttaattg tgccttcttt tctctgcatc cccttctttt tttctgacaa      600
tctgtgtctg tcccaggtct ctttgtccgc gcctctccca catactagaa atctctccct     660
ttcttgaggt tgggatgaag aagcagttgg gacggccagc tggaggtctg cgtggtagag     720
ggaactccag gtctgtctct gaggcccggt tggaagacgt cagtgtttct aagacggaac     780
ccaccgcaaa agaagggagc gctcagtggg gtgggagtag cggtgtgcca ggcaacagaa     840
cccctgaggg ccgggctggg attggactcc tgacctgtgg ctgtgacaga tgtgcacatg     900
gggtttaggg gcaaaggagt gggtttggac tcgggaggag ctggggtggg tttcctaaca     960
tgtggtgtag gccgtaaaaa aatccctagg aattctggac ttctgagtcc caaagcatgt    1020
gggcagggcc cccgaggaaa agtaaggact ggggaaactt tgttttgacc ctctgacctc    1080
aagaccaccg gggcaactga agccaggcgc cgggagaccc tactggggc agagcgggac    1140
cactggctac tgccagcttg tgtatccctg ttggccccc gcccaagcgg gatctgggga    1200
ccgaggcccc tcctctggct cagaccaccc tgcctgccct tgctcccgc tctgaatcct    1260
ctttcaggcc ccatgaccct gaaacaatca acccaggaca gttagcttg ggaacagcat    1320
caaggaaagg aaactccgta gaggccgagg gtttgggca tccggagaac cagggacttt    1380
atggtatagg tctttccttc cagtacgggg agaaaagatg ggcagttttc ttctgggaag    1440
aaagttcgtg aacgcgggtg atttacccta ggggggcggg gttcagaagg acccccctcc    1500
attatctctc tgggcatccc cgccggacag acgtctcaga ctcactcttg acgtcactag    1560
ggggttcccg gggtctata ggggttaacc cttaggaaac cggcggagat accaggaat    1620
ccaaggtgtc ctctccgcgc acaccttatt tacacaggca cttctttctc ttagtttctg    1680
ggttcttctt tccactccac tatagggacc ccactttcca atagtgcctt ttcccccccc    1740
accccggc gctactggct gnttttnang atgcccttaa aaagggaag aatgttccac     1800
cccttaccc gnccccctt tatagggtt aacccttagg aaccggcgg agataccag    1860
gaatccaagg tgtcctctc gcgcacacct tatttacaca ggcacttctt tctcttagtt    1920
tctggtttct tcttcccac tccactatag gaccccact ttccaatagt gcctctcccc    1980
ccccccaccc cgggcgctac tgcctgcttt caggatgcgc tgagagaggg aagaatgttc    2040
caccccttcac cgccccccct cgctttctg ggctgcccag aagctgagcc               2100
gtctgcagcc agagcctgcg gcggcgactt gggtgggccg agaaggcacg gggcggga    2160
aggcgggacc gggaaaaggg ggtgggggccg actccaggga gttggggaga aggggtacgt    2220
acgtagagga ctctagaaaa tagactgcga agatgattcg ggtctttggt aggctaattc    2280
tcatgctccc atccagccca gaaaaccttt actgaaactg gaaaagttag tagtatgaag    2340
agggaggcgt gagtgtaggc ggtggctctc ggtgaagggg gctgtcgccc cgtttttatc    2400
ctgtctcttg gagctctcgg gcaatggaac aggaagagtg acaactttga gggaacttct    2460
agtgtctggg ggtcctttac aagtccttcc cttcccttga atgagtcaca gaggagagag    2520
gcgggagatg tgccccctca tccagctgcc agccagctgt gccccccacc cccacgttag    2580
tgccaatgtc gagctggag gtcttggatg cgggattcgg gtctcggctg gaaaaggagg    2640
agttagcaaa ggtagcccgg gctacagcac tttggctggg tcgtagggtc cgggttccgt    2700
tccccatttt accccgccct caccctaaat cccagcatcc cgggatcacc caccgcgccg    2760
gccggcccgc tcccagtggt tctccacccc accccgcccc acccacccct ccgttccccg    2820
aaggctgaaa aacctgggagt tggagtaaaaa cttgttgagg gaaagcggac ctcgcatcag    2880
ctcctctctc tctagccttg aggacttcgt tttctcattc ccattaagac tttcctgaca    2940
gccccttccc gatttcccc aaaaccaaac gggataggta acccagagt taanccgcct    3000
cagaatgact ttagctctca tccttttac tcaaaagtcg gggagacgct ctgctctgaa    3060
gtcttattcc ctcccacaca tagttcctg tctgaggaca gatcatttgt gttctcttct    3120
ggccctacca gtctatntgt actgaaacga gtctccctc tagtgnncac tggagagatt    3180
gctcatgagc tctgctcttg ggcatgagcc ggcagccctg ggcatgaagt cagaccttcc    3240
gtgtgttcca ccatcacaca cctcaaagct ggcccatggc cagaacaaga aatggtagag    3300
ggaaaagaaa aaagaaaagc aagtagagag agctcatgag gatcatttgt attaaaaatc    3360
acctaggact tgtgttggat cagttagtcc ctaacattcc cttgtacata cagagactgt    3420
ggatccccaa gactgaacgg ctgcttctgc ccactctttg ggatgtttct tcttaaggaa    3480
gctgaaaaac gttattgatt tccatgacca gtttctgaga tgaggttag aggtacaagg    3540
gacatgctgg cgaggggggg ggggggggaa atctgtgcct gaaactgtca tttatcttct    3600
ctgtttcgtc
```

-continued

```
catctttata actgtcagat ctacattcct ttccacaggt cccctcatcc ttccctgaga    3660
cgccatgttc aatccaatga ctccgccaca agtcaatagc tatagtg                  3707
```

<210> SEQ ID NO 60
<211> LENGTH: 4620
<212> TYPE: DNA
<213> ORGANISM: human

<400> SEQUENCE: 60

```
ctctccgttt ctcagagctc acatatccac ctcctgggct tttaagtggg ctttagtgag      60
gggctcctcc ttcaactggg ctcctccttc agttcccag ctcttctgct tcgactccga     120
gcgggtgtca tgtgtgagaa cggccagcag agggagcaga aagcctggaa gagcagctag    180
agcctgcagt gacgtggtgc ggaggggcgg caccctccag aacttcgaga cgtagagccg    240
gggttctagg gaaagggct tcagtcccag ggctccttgg tgacctcgtg aaccacaccc     300
tgcacccaga gcctcagccg ctgctccttg cttttatgct ccatagactc ctcaccttct    360
tccagagccc caacccaac ttgatttgcc ccaaaccgca actctgtccc ggccgctgca     420
agttccatcc aaaggtgag gcctgcagat aaaccacagg atggcagaat gctcagttag     480
caccaaccaa aggcgactac cctacctcca ctattatcgt tctcggttga acttctcccc    540
ctgccccgca atattttcct caatctggtt gtcggggcct ctttggggcc agccgatcca    600
gaaatccaag ccggattta gtactcacca acagcagcct gttcagccgg ggcggggggg    660
gggcgtaagc agtataggt ccctcaaggg agggggagga tcctgggggt cctgggggtg    720
caataagccc ggcacccctt tcttgcttc cagctacccc gcctcatcct ccagaacggc    780
aagagggagg gaaatagaag gggagtgagg ggcgagcggg aagagccgag gcgcgccagc    840
ggctgagag agaaaagtt tttgcaaaag ggaaaaaaa agtttgcgct tctcgcggt       900
ggtccgggct tgcggcccgg cgggctgggc cggcgggagg gctggggcc aggttgggg      960
ggtgggggtg gcatcgaggc tgcgctgccg tggccctctc cgcccccct ccccaccgca   1020
caccccccag cccagactcc agccctggac cgcgcatccc gagcccagcg cccagacaga   1080
ggtgagaagg gggggcaggc gggggaccac ctgggagcag tgggggaggg ggcctgaggg   1140
gatgctcagc ttcttaggga ctcatcccag acccgggaca tagaggcaaa atagggtgg    1200
gagagcctgg ggtgagacat tagaaactcc agattttca cttgtgtctt tctctgtatc   1260
ttcttttct tcccttttt tcttctgtca gtctgtgtat ctctgtctca gggaaccgtg    1320
ggtcttttgtc tccgcctctc ccatatatta gaaatatctt acttctcatgc ggttaagttt  1380
aagaggctgg agggatggct agctggaggt ctgcgttgta gagaggtaac cccaggtgtg   1440
tgtctgcgcg tgggtagga agatgtcagt gtttctgaaa ggtgggact gcaaaggagg    1500
gagctccagg tggggtggg acgggtgtgt gggaggcaac agagccacta ggggccagcc   1560
aggcttgaac ctttgacctg tcttgtgaca gatgtgccag tggatgcttg tgctttaggg   1620
gaaaggagtg tcttctggac ttggaaggg gctggggcgg ggggggctg tccaaggtct    1680
agtgaaggcc ctagaatgac cccatgcaat ttggactcct gagtcccaag ggctgtgggc   1740
aaggagctca ggaggagccg ggggagacct tgtcttgacc tctgacctca ggaccaccgg   1800
ggcagccggga gccagccgca gggagacccc taccggggct gggcgggacc actggccact   1860
gccagcctgt gtatcccccgt tggcacccg cccaaacggg agctgggat cgaggcccct   1920
cctctggctc agaccaccct gcctgccctt gctcccgct ctgaatcctc tttcaggtcc    1980
catgacccgc aaacaatcag cactgggcag ctagctttcg ggacaggatt acggaaaggg   2040
gaccccgtag agcctgggga ctgagggttt taggggtctg aggagctggg gtcttctagg   2100
ataggtcttt acgttccagt agagggagaa ggcgggcggt ttccggggg atatgtaagg    2160
gtcggaataa gtgtggtttt attaggggc gggtccaga gacctctccc cctccaccat    2220
tatctccctg gcatcccgc ccttgacgtc accaggggt tcccgggggt ctggagggt     2280
taaccctttgg gaagccggct gctataacca gcaacctaag gtgtccgggc ccctcctcct   2340
ccccatacac acctaattttt attgacccag tcactttctc tgcttttctct cccctatact   2400
ttctgatttc ttctcccttt ctaacccccac caacgggac ccccactctc cagtagtgcc    2460
ccctgggcg ccactgcctg cttttccggat gtgctgagag gaggaggga gaatgtggcc    2520
cgccccctcag cccccacccc tatggctcgc tctactgggg tcccgggcg ggtggggga    2580
gcggagccgt ctgcagccag tgcctgcggc ggcgacttgg tgtggccgag gaggcacggg   2640
ggcggggaag gcgggaccgg gagtagggg gcggagccga ctcctggag ttggggagcg    2700
ggggtgcgag ggggacgctg gaaaacaggg agacaccgaa gatggtttag ggctccggca   2760
ggggaacct agagctccct gtcccatccc gaactctcca accccagaaa aactttaccg   2820
aagctaaaaa agttggcgac atttcctttt tactagcctg aaggggagat atgggtggc   2880
tgtggaacgc gtgggcgagg aggggtgtag ccccatttcc ttggaggctc ttccggcagct   2940
aggcagtggg gcagaaagat gactgagtag gcaagtttgg gggagtctct agtgtttggg   3000
ggatcatttg caaacttccc tccttcccct gggtgagtca tagaggagg gagggcggag    3060
aattgtcccc ccatccagct gccaaccagc tgtgccccc gcccccaac attagttcca   3120
aggtcgagtt gggaggtctt ggatgcggga tccgcacctc ggttggaaaa ggaggagtta   3180
gaaaagggta cagcccaggc tgccgggccg gctgggtcg cgggtccgg gttccgctcc     3240
ccatctcacc ccgccctcac cctaaatccc agcatcccgac gatcacccac cgcgcgggcc   3300
ggcccggccc gctcccggtg gttctccacc ccatcccgcc ccacccacc ctcattcccg    3360
ggagactgga aaacccggga tggagtcaaa actggagttt gaaaagaaaa acggacagca   3420
gcaccttctt cctcgctacg cttttataag gatcacattg tttttttcat tctctcagag    3480
tctccctca tacttccttt cctgttcccc caaaacagag accaaaaaga ttaggtgggc   3540
ctgatttaaa ctaccccaga ataacaccag cttcacctt tgtgcccaac agaccagaa    3600
gactccctc aggaacctta cctcctcctc cacactgtttt tctgtctaag agggcagatg    3660
gcttgtgctc cctcctggcc ccacctggct ctgtgtcggg actgtggcta ggctccctc   3720
tgctggacac tgcagagatt gtacacgggc tgtccctggg gagggcacg agaaggaagg   3780
gggaacggc tctagcagga ccgccccagtg cttgaagtca gatccatcac acgagttctc   3840
ccatcccacc ctcaaagccg gcccagggtt acagcaagaa gaattagagg gtccatgtta   3900
ctaaaatcac ttgaagttaa tataggcaca attagtccaa acatgccttt ctacacacag   3960
accacacagg caaagctccc acccaggcaa agctcccacc cagttcccaa gaagatcccc   4020
agagtacaca gactacaaga ctgcctctgc ctctctggga catcattccc ccttaccccc   4080
```

-continued

```
ccccctcactc agcgagtgat gcttttttg ttttgagacg gagtctagct ctgtcaccca    4140
ggctggagtg cagtggcacc atctcggctc actgaaacct ccgcctccca ggttcaagcg    4200
attcttctgc ctcagccttc cgagtagctg ggattacagg cacccgccat catgactggc    4260
taatttttgt tttttgtag agacgggggt ttcaccagt tggccaggct ggtcttcaac     4320
tgacctcagg tgatcctccc gcctcagcct ctcaaagcgt tggaattaca ggcgtgagcc    4380
actgtgcccg gctcagtgat gctcttttca actcgaattc cgtggcagat gtcttagagg    4440
ggtgggggat accagggatg ttctgcccag gattctgtgc ctgagactgc tgtctgacag    4500
tctctatttc ctccacctt atacctacct tccctttctg cagtgtcccc acacctcct     4560
ctgagacgcc atgttcaact cgatgacccc accaccaatc agtagctatg gcgagccctg    4620
```